(12) United States Patent
Yocum et al.

(10) Patent No.: US 7,989,187 B2
(45) Date of Patent: *Aug. 2, 2011

(54) MICROORGANISMS AND PROCESSES FOR ENHANCED PRODUCTION OF PANTOTHENATE

(75) Inventors: Rogers R. Yocum, Lexington, MA (US); Thomas A. Patterson, North Attleboro, MA (US); Janice G. Pero, Lexington, MA (US); Theron Hermann, Kinnelon, NJ (US)

(73) Assignee: BASF SE, Ludwigshafen (DE)

( * ) Notice: Subject to any disclaimer, the term of this patent is extended or adjusted under 35 U.S.C. 154(b) by 1082 days.

This patent is subject to a terminal disclaimer.

(21) Appl. No.: 10/520,220

(22) PCT Filed: Jul. 3, 2003

(86) PCT No.: PCT/US03/21305
§ 371 (c)(1),
(2), (4) Date: Oct. 26, 2005

(87) PCT Pub. No.: WO2004/005525
PCT Pub. Date: Jan. 15, 2004

(65) Prior Publication Data
US 2006/0141585 A1 Jun. 29, 2006

Related U.S. Application Data

(60) Provisional application No. 60/393,826, filed on Jul. 3, 2002.

(51) Int. Cl.
*C12P 13/04* (2006.01)
*C12N 9/00* (2006.01)
*C12N 9/10* (2006.01)
*C12N 1/20* (2006.01)
*C12N 15/00* (2006.01)
*C07H 21/04* (2006.01)

(52) U.S. Cl. ..... 435/106; 435/183; 435/193; 435/252.3; 435/320.1; 536/23.2

(58) Field of Classification Search ................. None
See application file for complete search history.

(56) References Cited

U.S. PATENT DOCUMENTS

| | | | |
|---|---|---|---|
| 6,171,845 B1 | 1/2001 | Elischweski et al. | |
| 6,184,006 B1 | 2/2001 | Rieping et al. | |
| 6,184,007 B1 | 2/2001 | Dusch et al. | |
| 6,787,334 B1 | 9/2004 | Elischweski et al. | |
| 7,262,045 B2 | 9/2004 | Kruse et al. | |
| 7,244,593 B2* | 7/2007 | Yocum et al. | 435/106 |
| 7,291,489 B2* | 11/2007 | Yocum et al. | 435/106 |

FOREIGN PATENT DOCUMENTS

| | | |
|---|---|---|
| CN | 1254758 | 5/2000 |
| WO | WO-01/21772 A1 | 4/2000 |
| WO | WO-02/057474 A2 | 7/2002 |
| WO | WO-02/057476 A2 | 7/2002 |
| WO | WO-02/061108 A2 | 8/2002 |
| WO | WO-2004-005525 A2 | 1/2004 |
| WO | WO-2004/005527 A1 | 1/2004 |

OTHER PUBLICATIONS

Sahm et al. Appl Environ Microbiol. May 1999;65(5):1973-9.*
Jones et al. J Bacteriol. Apr. 1993;175(7):2125-30.*
Chica et al. Curr Opin Biotechnol. Aug. 2005;16(4):378-84.*
Sen et al. Appl Biochem Biotechnol. Dec. 2007;143(3):212-23.*
Seffernick et al. J Bacteriol. Apr. 2001; 183 (8): 2405-10.*
Witkowski et al. Biochemistry. Sep. 7, 1999; 38(36): 11643-50.*
Teller, Joel H. et al., "Ketopantoate Hydroxymethyltransferase, I. Purification and Role in Pantothenate Biosynthesis," *The Journal of Biological Chemistry*, vol. 251(12):3780-3785 (Jun. 1976).
Powers, Sue et al., "Ketopantoate Hydroxymethyltransferase, II. Physical, Catalytic, and Regulatory Properties," *The Journal of Biological Chemistry*, vol. 251(12):3786-3793 (Jun. 1976).
Genschel, Ulrich et al., "The final step of pantothenate biosynthesis in higher plants: cloning and characterization of pantothenate synthetase from *Lotus japonicus* and *Oryza sativum* (rice)," *Biochem, J.*, vol. 341:669-678 (1999).
Sahm, Hermann et al., "D-Pantothenate Synthesis in *Corynebacterium glutamicum* and Use of panBC and Genes Encoding L-Valine Synthesis for D-Pantothenate Overproduction," *Applied and Environmental Microbiology*, vol. 65(5):1973-1979 (1999).
Holmes, William B. et al., "Cloning and Characterization of Methenyltetrahydrofolate Synthetase from *Saccharomyces cerevisiae*," *The Journal of Biological Chemistry*, vol. 277(23):20205-20213 (2002).
Song, Woo-Joo et al., "Kinetics and Regulation of Pantothenate Kinase from *Escherichia coli*," *The Journal of Biological Chemistry*, vol. 269(43):27051-27058 (1994).
Dusch, Nicole et al., "Expression of the *Corynebacterium glutamicum* panD Gene Encoding L-Aspartate-α-Decarboxylase Leads to Pantothenate Overproduction in *Escherichia coli*," *Applied and Environmental Micobiology*, vol. 65(4):1530-1539 (1999).
Ottenhof, Harald H. et al., "Organisation of the pantothenate (vitamin $B_5$) biosynthesis pathway in higher plants," *The Plant Journal*, vol. 37:61-72 (2003).

* cited by examiner

*Primary Examiner* — Christian L Fronda
(74) *Attorney, Agent, or Firm* — Connolly Bove Lodge & Hutz, LLP

(57) ABSTRACT

The present invention features improved methods for the enhanced production of pantoate and pantothenate utilizing microorganisms having modified pantothenate biosynthetic enzyme activities and having modified methylenetetrahydrofolate (MTF) biosynthetic enzyme activities. In particular, the invention features methods for enhancing production of desired products by increasing levels of a key intermediate, ketopantoate, by increasing enzymes or substrates that contribute directly or indirectly to its synthesis. Recombinant microorganisms and conditions for culturing same are also are featured. Also featured are compositions produced by such microorganisms.

34 Claims, 12 Drawing Sheets

FIG. 3
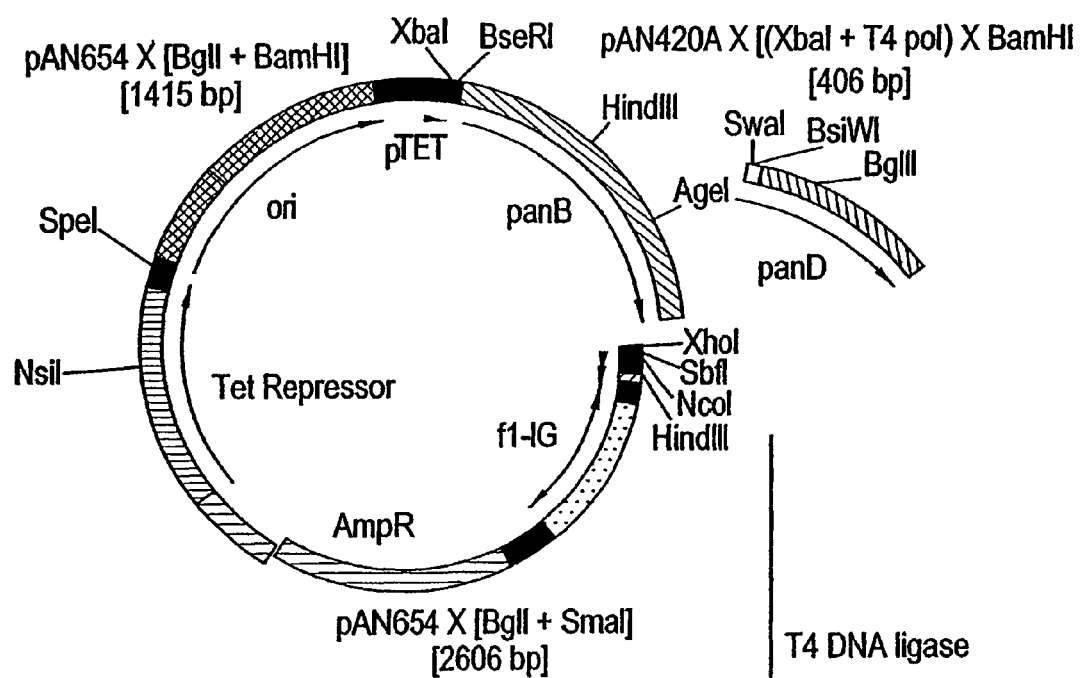
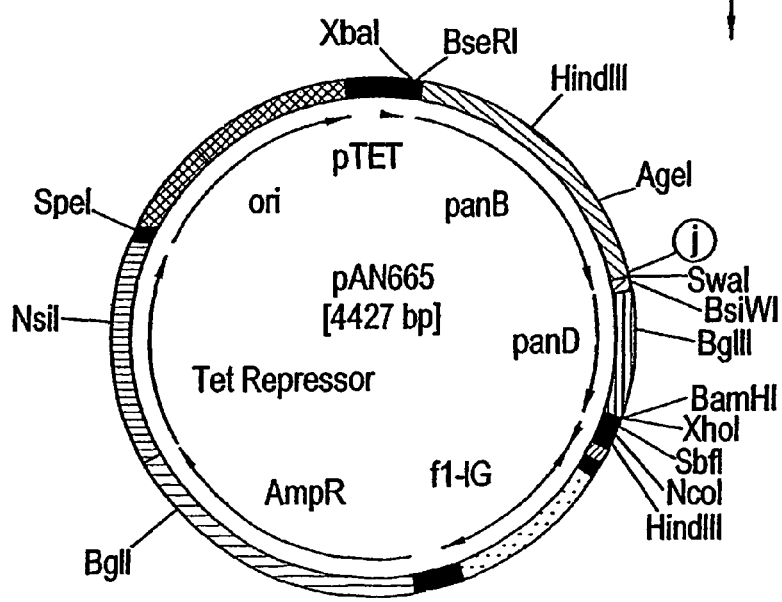

SEQUENCE LISTING

<160> NUMBER OF SEQ ID NOS: 31

<210> SEQ ID NO 1
<211> LENGTH: 194
<212> TYPE: DNA
<213> ORGANISM: Artificial Sequence
<220> FEATURE:
<223> OTHER INFORMATION: Description of Artificial Sequence:promoter
      sequence
<220> FEATURE:
<221> NAME/KEY: -35_signal
<222> LOCATION: (136)..(141)
<220> FEATURE:
<221> NAME/KEY: -10_signal
<222> LOCATION: (159)..(164)

<400> SEQUENCE: 1
gctattgacg acagctatgg ttcactgtcc accaaccaaa actgtgctca gtaccgccaa    60
tatttctccc ttgaggggta caaagaggtg tccctagaag agatccacgc tgtgtaaaaa   120
ttttacaaaa aggtattgac tttccctaca gggtgtgtaa taatttaatt acaggcgggg   180 gcaacccccgc ctgt                                                    194

<210> SEQ ID NO 2
<211> LENGTH: 163
<212> TYPE: DNA
<213> ORGANISM: Artificial Sequence
<220> FEATURE:
<223> OTHER INFORMATION: Description of Artificial Sequence:promoter
      sequence
<220> FEATURE:
<221> NAME/KEY: -35_signal
<222> LOCATION: (113)..(118)
<220> FEATURE:
<221> NAME/KEY: -10_signal
<222> LOCATION: (136)..(141)

<400> SEQUENCE: 2
gcctacctag cttccaagaa agatatccta acagcacaag agcggaaaga tgttttgttc    60
tacatccaga acaacctctg ctaaaattcc tgaaaaattt tgcaaaaagt tgttgacttt   120
atctacaagg tgtggtataa taatcttaac aacagcagga cgc                    163

<210> SEQ ID NO 3
<211> LENGTH: 127
<212> TYPE: DNA
<213> ORGANISM: Artificial Sequence
<220> FEATURE:
<223> OTHER INFORMATION: Description of Artificial Sequence:promoter
      sequence
<220> FEATURE:
<221> NAME/KEY: -35_signal
<222> LOCATION: (34)..(39)
<220> FEATURE:
<221> NAME/KEY: -10_signal
<222> LOCATION: (58)..(63)
<220> FEATURE:
<221> NAME/KEY: -35_signal
<222> LOCATION: (75)..(80)
<220> FEATURE:
<221> NAME/KEY: -10_signal
<222> LOCATION: (98)..(103)

<400> SEQUENCE: 3
gaggaatcat agaattttgt caaataatt ttattgacaa cgtcttatta acgttgatat     60
aatttaaatt ttatttgaca aaaatgggct cgtgttgtac aataaatgta gtgaggtgga   120
tgcaatg                                                             127

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 4
taaacatgag gaggagaaaa catg                                           24

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 5
attcgagaaa tggagagaat ataatatg                                       28

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 6
agaaaggagg tga                                                       13

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:ribosome
      binding site
<220> FEATURE:
<221> NAME/KEY: misc_feature
<222> LOCATION: 17, 18, 19, 20
<223> OTHER INFORMATION: n = a, t, c, or g

<400> SEQUENCE: 7
ttaagaaagg aggtgannnn atg                                            23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:ribosome
      binding site
<220> FEATURE:
<221> NAME/KEY: misc_feature
<222> LOCATION: 16, 17, 18, 19, 20
<223> OTHER INFORMATION: n = a, c, t, or g

<400> SEQUENCE: 8
ttagaaagga ggtgannnnn atg                                            23

<210> SEQ ID NO 9
<211> LENGTH: 23
<212> TYPE: DNA
<213> ORGANISM: Artificial Sequence
<220> FEATURE:

```
<223> OTHER INFORMATION: Description of Artificial Sequence:ribosome
      binding site
<220> FEATURE:
<221> NAME/KEY: misc_feature
<222> LOCATION: 14, 15, 16, 17, 18, 19, 20
<223> OTHER INFORMATION: n = a, c, t, or g

<400> SEQUENCE: 9
agaaaggagg tgannnnnnn atg                                              23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:ribosome
      binding site
<220> FEATURE:
<221> NAME/KEY: misc_feature
<222> LOCATION: 14, 15, 16, 17, 18, 19
<223> OTHER INFORMATION: n = a, c, t, or g

<400> SEQUENCE: 10
agaaaggagg tgannnnnna tg                                               22

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 11
ccctctagaa ggaggagaaa acatg                                            25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 12
ccctctagag gaggagaaaa catg                                             24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 13
ttagaaagga ggatttaaat atg                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 14
ttagaaagga ggtttaatta atg                                              23
```

```
<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 15
ttagaaagga ggtgatttaa atg                                              23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 16
ttagaaagga ggtgtttaaa atg                                              23

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 17
attcgagaaa ggaggtgaat ataatatg                                         28

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 18
attcgagaaa ggaggtgaat aataatg                                          27

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence:ribosome
      binding site

<400> SEQUENCE: 19
attcgtagaa aggaggtgaa ttaatatg                                         28

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence:5' PCR
      primer
<220> FEATURE:
<223> OTHER INFORMATION: for serA gene

<400> SEQUENCE: 20
ccctctagag gaggagaaaa catgtttcga gtattggtct cagacaaaat g               51
```

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence:3' PCR
      primer
<220> FEATURE:
<223> OTHER INFORMATION: for serA gene

<400> SEQUENCE: 21
cccggatcca attatggcag atcaatgagc ttcacagaca caa            43

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence:5' PCR
      primer
<220> FEATURE:
<223> OTHER INFORMATION: for glyA gene

<400> SEQUENCE: 22
ggatctagag gaggtgtaaa catgaaacat ttacctgcgc aagacgaa        48

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence:3' PCR
      primer
<220> FEATURE:
<223> OTHER INFORMATION: for glyA gene

<400> SEQUENCE: 23
cggggatccc ccatcaacaa ttacacactt ctattgattc tac            43

<210> SEQ ID NO 24
<211> LENGTH: 7926
<212> TYPE: DNA
<213> ORGANISM: Artificial Sequence
<220> FEATURE:
<223> OTHER INFORMATION: Description of Artificial Sequence:serA
      overexpression
<220> FEATURE:
<223> OTHER INFORMATION: plasmid

<400> SEQUENCE: 24
gaattttgcg gccgcttcga agctgtaat ataaaaacct tcttcaacta acggggcagg        60
ttagtgacat tagaaaaccg actgtaaaaa gtacagtcgg cattatctca tattataaaa      120
gccagtcatt aggcctatct gacaattcct gaatagagtt cataaacaat cctgcatgat      180
aaccatcaca aacagaatga tgtacctgta agatagcgg taaatatatt gaattacctt      240
tattaatgaa ttttcctgct gtaataatgg gtagaaggta attactatta ttattgatat      300
ttaagttaaa cccagtaaat gaagtccatg gaataataga agagaaaaa gcattttcag      360 gtataggtgt tttgggaaac aatttccccg aaccattata tttctctaca tcagaaaggt      420
ataaatcata aaactctttg aagtcattct ttacaggagt ccaaatacca gagaatgttt      480
tagatacacc atcaaaaatt gtataaagtg gctctaactt atcccaataa cctaactctc      540
cgtcgctatt gtaaccagtt ctaaaagctg tatttgagtt tatcacccct gtcactaaga      600
aaataaatgc agggtaaaat ttatatcctt cttgtttat gtttcggtat aaacactaa      660

```
tatcaatttc tgtggttata ctaaaagtcg tttgttggtt caaataatga ttaaatatct    720
cttttctctt ccaattgtct aaatcaattt tattaaagtt catttgatat gcctcctaaa    780
tttttatcta aagtgaattt aggaggctta cttgtctgct ttcttcatta gaatcaatcc    840 tttttttaaaa gtcaatatta ctgtaacata aatatatatt ttaaaaatat cccactttat    900
ccaattttcg tttgttgaac taatgggtgc tttagttgaa gaataaagac cacattaaaa    960
aatgtggtct tttgtgtttt tttaaaggat ttgagcgtag cgaaaaatcc ttttctttct   1020
tatcttgata ataagggtaa ctattgaatt cggtaccaag agtttgtaga aacgcaaaaa   1080
ggccatccgt caggatggcc ttctgcttaa tttgatgcct ggcagtttat ggcgggcgtc   1140
ctgcccgcca ccctccgggc cgttgcttcg caacgttcaa atccgctccc ggcggatttg   1200
tcctactcag gagagcgttc accgacaaac aacagataaa acgaaaggcc cagtcttcg    1260 actgagcctt tcgttttatt tgatgcctgg cagttccta ctctcgcatg gggagacccc    1320
acactaccat cggcgctacg gcgtttcact tctgagttcg gcatgggtc aggtgggacc    1380 accgcgctac tgccgccagg caaattctgt tttatcagac cgcttctgcg ttctgattta   1440
atctgtatca ggctgaaaat cttctctcat ccgccaaaac aggatccaat tatggcagat   1500
caatgagctt cacagacaca atatcaggga catttgttag ttcttttcaca attttatctt   1560 ccagatgtct gtcaaaggaa agcatcatga tggcttctcc gccttttttcc ttacggccaa   1620 cctgcatagt tgcaatgtta atatcattat ctccgagaat acgtcctact cggccgatga   1680
cacctgttgt atcttgatgc tggatataca ccaagtgacc agtcggataa aaatcaatat   1740
taaatccatt gatctcgaca attcgttctc cgaaatgagg aatatacgta gccgttacag   1800
taaaggtgct gcggtctcct gtcacttta cgctgatgca gttatcgtat ccagattcag   1860
aagaggaaat ttttttcactg aagctaatgc cgcgttcttt tgcgacaccc ccggcattga   1920
cctcattaac agtagagtct acgcgcggtt taaaaagcc tgacagaagg cttttgtaa    1980 tgaacgatgt ttcaagttta gcaattgtgc cttcatattg aatggcaaca tcctgtactg   2040
gttctttcat gcactgtgat acaaggctgc caattttttcc tgcaatttga tggtaaggct   2100
taattttagc aaaattcatct tttgtcatgg caggcaggtt gatagctgac atgacaggca   2160
ggccttttgc gaactgcaga acttcttctg acacttgggc ggcgacattg agctgtgctt   2220
ctttcgttga tgctcccaag tgaggagtgg caatgactaa tggatgatca acaagtttgt   2280
tgtcaactgg cggttcgact tcgaaaacgt caagcgctgc tcccgcaaca tgcccgtttt   2340
ccaaagcttc gagaagtgct gcttcatcga taattccgcc tcgcgcacag ttaattaagc   2400
gaacgccttt tttcgttttt gcaatcgttt ctttattcaa taagccttt gtttcttttg    2460 ttaaaggcgt gtgaacggta atgatatccg cactttcaag cacttcttca aatgtacggc   2520
tgtttacgcc gatttttttc gctctttctt ccgttaagaa aggatcaaaa acgtgcacag   2580
tcataccgaa cgctcctcga cgctgtgcaa tttcacttcc gattcggcct aatcctacaa   2640
taccaagcgt ttttccataa agctctgaac cgacataagc tgtgcggttc cactctctgg   2700
atttcactga gatattagcc tgcggaatgt gtctcattaa agaagagatc attgcaaatg   2760
tatgctcagc tgtcgaaatg gtgttgccgt tcggagcatt gatcacgatt accccgtgtt   2820
tcgtagcctc atcaatatcg atattatcga caccgacacc ggctcttccg acaattttta   2880
aagaagtcat tttgttgaaa aggtcttctg ttactttgt cgcgcttcgc accaaaagag    2940
catcaaaagt atgtaattca tcttctgcat ctgctacgtt ttttgaacg atttcaataa    3000 agtctgattc aataagtggc tgtaaaccgt cgttgctcat tttgtctgag accaatactc   3060
```

```
gaaacatgtt ttctcctcct ctagagcgtc ctgctgttgt taagattatt ataccacacc    3120
ttgtagataa agtcaacaac tttttgcaaa atttttcagg aatttttagca gaggttgttc    3180 tggatgtaga acaaaacatc tttccgctct tgtgctgtta ggatatcttt cttggaagct    3240
aggtaggcct cgagttatgg cagttggtta aaaggaaaca aaaagaccgt tttcacacaa    3300
aacggtcttt ttcgatttct ttttacagtc acagccactt ttgcaaaaac cggacagctt    3360
catgccttat aactgctgtt tcggtcgaca agcttcgcga agcggccgca aaattcactg    3420
gccgtcgttt tacaacgtcg tgactgggaa aaccctggcg ttacccaact taatcgcctt    3480
gcagcacatc cccctttcgc cagctggcgt aatagcgaag aggcccgcac cgatcgccct    3540
tcccaacagt tgcgcagcct gaatggcgaa tggcgcctga tgcggtatt t tctccttacg    3600 catctgtgcg gtatttcaca ccgcatatgg tgcactctca gtacaatctg ctctgatgcc    3660
gcatagttaa gccagccccg acacccgcca acacccgctg actatgcttg taaaccgttt    3720
tgtgaaaaaa ttttttaaaat aaaaaagggg acctctaggg tccccaatta attagtaata    3780
taatctatta aaggtcattc aaaaggtcat ccaccggatc agcttagtaa agccctcgct    3840 agatttt aat gcggatgttg cgattacttc gccaactatt gcgataacaa gaaaaagcca    3900
gcctttcatg atatatctcc caatttgtgt agggcttatt atgcacgctt aaaaataata    3960
aaagcagact tgacctgata gtttggctgt gagcaattat gtgcttagtg catctaacgc    4020
ttgagttaag ccgcgccgcg aagcggcgtc ggcttgaacg aattgttaga cattatttgc    4080
cgactacctt ggtgatctcg cctttcacgt agtggacaaa ttcttccaac tgatctgcgc    4140
gcgaggccaa gcgatcttct tcttgtccaa gataagcctg tctagcttca agtatgacgg    4200
gctgatactg ggccggcagg cgctccattg cccagtcggc agcgacatcc ttcggcgcga    4260
ttttgccggt tactgcgctg taccaaatgc gggacaacgt aagcactaca tttcgctcat    4320
cgccagccca gtcgggcggc gagttccata gcgttaaggt ttcatttagc gcctcaaata    4380
gatcctgttc aggaaccgga tcaaagagtt cctccgccgc tggacctacc aaggcaacgc    4440
tatgttctct tgcttttgtc agcaagatag ccagatcaat gtcgatcgtg ctggctcga    4500 agatacctgc aagaatgtca ttgcgctgcc attctccaaa ttgcagttcg cgcttagctg    4560
gataacgcca cggaatgatg tcgtcgtgca caacaatggt gacttctaca gcgcggagaa    4620
tctcgctctc tccaggggaa gccgaagttt ccaaaaggtc gttgatcaaa gctcgccgcg    4680
ttgtttcatc aagccttacg gtcaccgtaa ccagcaaatc aatatcactg tgtggcttca    4740
ggccgccatc cactgcggag ccgtacaaat gtacggccag caacgtcggt tcgagatggc    4800
gctcgatgac gccaactacc tctgatagtt gagtcgatac ttcggcgatc accgcttccc    4860
tcatgatgtt taactttgtt ttagggcgac tgccctgctg cgtaacatcg ttgctgctcc    4920
ataacatcaa acatcgaccc acggcgtaac gcgcttgctg cttggatgcc cgaggcatag    4980
actgtacccc aaaaaaacag tcataacaag ccatgaaaac cgccactgcg ccgttaccac    5040
cgctgcgttc ggtcaaggtt ctggaccagt tgcgtgagcg catacgctac ttgcattaca    5100
gcttacgaac cgaacaggct tatgtccact gggttcgtgc cttcatccgt ttccacggtg    5160
tgcgtcaccc ggcaaccttg ggcagcagcg aagtcgaggc atttctgtcc tggctggcga    5220
acgagcgcaa ggtttcggtc tccacgcatc gtcaggcatt gcggccttg ctgttcttct    5280 acggcaaggt gctgtgcacg gatctgccct ggcttcagga gatcggaaga cctcggccgt    5340
cgcggcgctt gccggtggtg ctgacccgg atgaagtggt tcgcatcctc ggttttctgg    5400
aaggcgagca tcgtttgttc gcccagcttc tgtatggaac gggcatgcgg atcagtgagg    5460
```

```
gtttgcaact gcgggtcaag gatctggatt tcgatcacgg cacgatcatc gtgcgggagg    5520
gcaagggctc caaggatcgg gccttgatgt tacccgagag cttggcaccc agcctgcgcg    5580
agcaggggaa ttgatccggt ggatgacctt ttgaatgacc tttaatagat tatattacta    5640
attaattggg gacccagag gtcccctttt ttattttaaa aatttttca caaaacggtt     5700 tacaagcata acgggttttg ctgcccgcaa acgggctgtt ctggtgttgc tagtttgtta    5760
tcagaatcgc agatccggct tcaggtttgc cggctgaaag cgctatttct tccagaattg    5820
ccatgatttt ttccccacgg gaggcgtcac tggctcccgt gttgtcggca gctttgattc    5880
gataagcagc atcgcctgtt tcaggctgtc tatgtgtgac tgttgagctg taacaagttg    5940
tctcaggtgt tcaatttcat gttctagttg ctttgtttta ctggtttcac ctgttctatt    6000
aggtgttaca tgctgttcat ctgttacatt gtcgatctgt tcatggtgaa cagctttaaa    6060
tgcaccaaaa actcgtaaaa gctctgatgt atctatcttt tttacaccgt tttcatctgt    6120
gcatatggac agttttccct ttgatatcta acggtgaaca gttgttctac ttttgtttgt    6180
tagtcttgat gcttcactga tagatacaag agccataaga acctcagatc cttccgtatt    6240
tagccagtat gttctctagt gtggttcgtt gttttttgcgt gagccatgag aacgaaccat    6300
tgagatcatg cttactttgc atgtcactca aaaattttgc ctcaaaactg gtgagctgaa    6360
tttttgcagt taaagcatcg tgtagtgttt tccttagtcc gttacgtagg taggaatctg    6420
atgtaatggt tgttggtatt ttgtcaccat tcatttttat ctggttgttc tcaagttcgg    6480
ttacgagatc catttgtcta tctagttcaa cttggaaaat caacgtatca gtcgggcggc    6540
ctcgcttatc aaccaccaat ttcatattgc tgtaagtgtt taaatcttta cttattggtt    6600
tcaaaaccca ttggttaagc ctttaaaact catggtagtt attttcaagc attaacatga    6660
acttaaattc atcaaggcta atctctatat ttgccttgtg agttttcttt tgtgttagtt    6720
cttttaataa ccactcataa atcctcatag agtatttgtt ttcaaaagac ttaacatgtt    6780
ccagattata ttttatgaat ttttttaact ggaaaagata aggcaatatc tcttcactaa    6840
aaactaattc taattttcg cttgagaact tggcatagtt tgtccactgg aaaatctcaa     6900
agcctttaac caaggattc ctgatttcca cagttctcgt catcagctct ctggttgctt     6960
tagctaatac accataagca ttttccctac tgatgttcat catctgagcg tattggttat    7020
aagtgaacga taccgtccgt tcttttccttg tagggttttc aatcgtgggg ttgagtagtg    7080
ccacacagca taaaattagc ttggtttcat gctccgttaa gtcatagcga ctaatcgcta    7140
gttcatttgc tttgaaaaca actaattcag acatacatct caattggtct aggtgatttt    7200
aatcactata ccaattgaga tgggctagtc aatgataatt actagtcctt ttcctttgag    7260
ttgtgggtat ctgtaaattc tgctagacct ttgctggaaa acttgtaaat tctgctagac    7320
cctctgtaaa ttccgctaga ccttttgtgtg ttttttttgt ttatattcaa gtggttataa    7380
tttatagaat aaagaaagaa taaaaaaaga taaaagaat agatcccagc cctgtgtata    7440
actcactact ttagtcagtt ccgcagtatt acaaaaggat gtcgcaaacg ctgtttgctc    7500
ctctacaaaa cagaccttaa aaccctaaag gcttaagtag caccctcgca agctcgggca    7560
aatcgctgaa tattcctttt gtctccgacc atcaggcacc tgagtcgctg tctttttcgt    7620
gacattcagt tcgctgcgct cacggctctg gcagtgaatg ggggtaaatg gcactacagg    7680 cgcctttat ggattcatgc aaggaaacta cccataatac aagaaaagcc cgtcacgggc     7740
ttctcagggc gttttatggc gggtctgcta tgtggtgcta tctgactttt tgctgttcag    7800
cagttcctgc cctctgattt tccagtctga ccacttcgga ttatcccgtg acaggtcatt    7860
```

```
cagactggct aatgcaccca gtaaggcagc ggtatcatca acaggcttac ccgtcttact    7920
gtcaac                                                              7926

<210> SEQ ID NO 25
<211> LENGTH: 7701
<212> TYPE: DNA
<213> ORGANISM: Artificial Sequence
<220> FEATURE:
<223> OTHER INFORMATION: Description of Artificial Sequence:glyA
      overexpression
<220> FEATURE:
<223> OTHER INFORMATION: plasmid

<400> SEQUENCE: 25
gaattttgcg gccgcttcga aagctgtaat ataaaaacct tcttcaacta acggggcagg      60
ttagtgacat tagaaaaccg actgtaaaaa gtacagtcgg cattatctca tattataaaa     120
gccagtcatt aggcctatct gacaattcct gaatagagtt cataaacaat cctgcatgat     180
aaccatcaca aacagaatga tgtacctgta agatagcgg taaatatatt gaattacctt     240
tattaatgaa ttttcctgct gtaataatgg gtagaaggta attactatta ttattgatat     300
ttaagttaaa cccagtaaat gaagtccatg gaataataga aagagaaaaa gcattttcag     360
gtataggtgt tttgggaaac aatttccccg aaccattata tttctctaca tcagaaaggt     420
ataaatcata aaactctttg aagtcattct ttacaggagt ccaaatacca gagaatgttt     480
tagatacacc atcaaaaatt gtataaagtg gctctaactt atcccaataa cctaactctc     540
cgtcgctatt gtaaccagtt ctaaaagctg tatttgagtt tatcacccett gtcactaaga     600 aaataaatgc agggtaaaat ttatatcctt cttgttttat gtttcggtat aaaacactaa     660
tatcaatttc tgtggttata ctaaaagtcg tttgttggtt caaataatga ttaaatatct     720
cttttctctt ccaattgtct aaatcaattt tattaaagtt catttgatat gcctcctaaa     780
tttttatcta aagtgaattt aggaggctta cttgtctgct ttcttcatta gaatcaatcc     840 tttttttaaaa gtcaatatta ctgtaacata aatatatatt ttaaaaatat cccactttat     900 ccaatttteg tttgttgaac taatgggtgc tttagttgaa gaataaagac cacattaaaa     960
aatgtggtct tttgtgtttt tttaaaggat ttgagcgtag cgaaaaatcc ttttctttct    1020
tatcttgata ataagggtaa ctattgaatt cggtaccaag agtttgtaga aacgcaaaaa    1080
ggccatccgt caggatggcc ttctgcttaa tttgatgcct ggcagtttat ggcgggcgtc    1140
ctgcccgcca ccctccgggc cgttgcttcg caacgttcaa atccgctccc ggcggatttg    1200
tcctactcag gagagcgttc accgacaaac aacagataaa acgaaaggcc cagtctttcg    1260
actgagcctt tcgttttatt tgatgcctgg cagttcccta ctctcgcatg gggagacccc    1320
acactaccat cggcgctacg gcgtttcact tctgagttcg gcatggggtc aggtgggacc    1380
accgcgctac tgccgccagg caaattctgt tttatcagac cgcttctgcg ttctgattta    1440
atctgtatca ggctgaaaat cttctctcat ccgccaaaac aggatccccc atcaacaatt    1500
acacacttct attgattcta caaaaaaga cattgagttt caagaacatc gtcaaaaaac    1560
ccgccgggca taagcccaag cgggttttag gatcttaata atctaattct ttatataaag    1620
gaaatttatc agtcagagca gctacacgct gtcttgcttc ttcaagtttt ccttcatctt    1680
cgtggttttt caatgcaagc gcaatgatag caccgacttc ttctaatgcg tctccgtcaa    1740
aaccgcggct ggttacagca gctgtaccaa gacggatgcc gcttgttacg aaaggttttt    1800
caggatcata tggaatcgcg ttttttgttag acgtaatacc aatttcatca agtacatgct    1860
ccgcaacctt accagtcagt ccgagcgaac gaaggtcaac aaggataagg tggttgtctg    1920
```

```
ttccgcctga acgagctgg atgccctctt tcgttaaggc ttcagccaga cgtttcgcgt    1980
ttgaaatgac gttttgtgca tatgttttga atcgtcctg caatacttca ccgaatgaaa    2040
cagcttttgc ggcaataacg tgcatcagag ggccgccttg aattccaggg aagatcgatt    2100
tatcaatttt cttgccaaac tcttcacggc aaaggatcat accgccgcga ggaccgcgaa    2160
gtgttttatg tgttgttgtt gtaacgaaat cagcgtaagg aacggggttt ggatgaaggc    2220
ctgccgcaac aagtcctgcg atatgtgcca tatccaccat gaagtaagcg ccgacttcat    2280
cagcaatttc acggaatttc ttaaagtcga ttgtacgagg atacgcactt gctcctgcta    2340
cgataagctt cggtttatga gcgagggctt tttcacgcac gtcatcgtaa tcaatatatt    2400
gagtttcttt atctacgccg tactcaacaa agttatattg aacaccgctg aagttgactg    2460
ggcttccgtg tgttaaatgg ccgccgtggg agaggttcat cccaagtaca gtatcgcctt    2520
gctccaaaat cgtgaagtac actgccatgt ttgcttgtgc gcctgaatga ggctgaacgt    2580
ttacatgctc cgctccaaag atttccttcg cgcggtcacg ggcgatatct tcaacgacat    2640
cgacgtgctc gcatccgccg tagtagcgtt tgcccggata tccttctgcg tacttatttg    2700
tcaaaacaga tccttgtgct tccataaccg cttcacttac aaagttctca gaagcaatca    2760
attcgatctt agtctgttgg cgttcacgct cattttttaat ggcgttaaac acttgttcgt    2820
cttgcgcagg taaatgtttc atgtttacac ctcctctaga gcgtcctgct gttgttaaga    2880
ttattatacc acccttgta gataaagtca acaactttttt gcaaaatttt tcaggaattt    2940
tagcagaggt tgttctggat gtagaacaaa acatctttcc gctcttgtgc tgttaggata    3000
tctttcttgg aagctaggta ggcctcgagt tatggcagtt ggttaaaagg aaacaaaaag    3060
accgttttca cacaaaacgg tcttttttcga tttcttttta cagtcacagc cacttttgca    3120
aaaaccggac agcttcatgc cttataactg ctgtttcggt cgacaagctt cgcgaagcgg    3180
ccgcaaaatt cactggccgt cgttttacaa cgtcgtgact gggaaaaccc tggcgttacc    3240
caacttaatc gccttgcagc acatcccccct ttcgccagct ggcgtaatag cgaagaggcc    3300
cgcaccgatc gcccttccca cagttgcgc agcctgaatg gcgaatggcg cctgatgcgg    3360
tattttctcc ttacgcatct gtgcggtatt tcacaccgca tatggtgcac tctcagtaca    3420
atctgctctg atgccgcata gttaagccag ccccgacacc cgccaacacc cgctgactat    3480
gcttgtaaac cgttttgtga aaaattttt aaaataaaaa aggggacctc tagggtcccc    3540
aattaattag taatataatc tattaaaggt cattcaaaag gtcatccacc ggatcagctt    3600
agtaaagccc tcgctagatt ttaatgcgga tgttgcgatt acttcgccaa ctattgcgat    3660
aacaagaaaa agccagcctt tcatgatata tctcccaatt tgtgtagggc ttattatgca    3720
cgcttaaaaa taataaaagc agacttgacc tgatagtttg gctgtgagca attatgtgct    3780
tagtgcatct aacgcttgag ttaagccgcg ccgcgaagcg cgtcggctt gaacgaattg    3840
ttagacatta tttgccgact accttggtga tctcgccttt cacgtagtgg acaaattctt    3900
ccaactgatc tgcgcgcgag gccaagcgat cttcttcttg tccaagataa gcctgtctag    3960
cttcaagtat gacgggctga tactgggccg gcaggcgctc cattgcccag tcggcagcga    4020
catccttcgg cgcgattttg ccggttactg cgctgtacca aatgcgggac aacgtaagca    4080
ctacatttcg ctcatcgcca gcccagtcgg gcggcgagtt ccatagcgtt aaggtttcat    4140
ttagcgcctc aaatagatcc tgttcaggaa ccggatcaaa gagttcctcc gccgctggac    4200
ctaccaaggc aacgctatgt tctccttgctt ttgtcagcaa gatagccaga tcaatgtcga    4260
tcgtggctgg ctcgaagata cctgcaagaa tgtcattgcg ctgccattct ccaaattgca    4320
```

```
gttcgcgctt agctggataa cgccacggaa tgatgtcgtc gtgcacaaca atggtgactt      4380
ctacagcgcg gagaatctcg ctctctccag gggaagccga agtttccaaa aggtcgttga      4440
tcaaagctcg ccgcgttgtt tcatcaagcc ttacggtcac cgtaaccagc aaatcaatat      4500
cactgtgtgg cttcaggccg ccatccactg cggagccgta caaatgtacg gccagcaacg      4560
tcggttcgag atggcgctcg atgacgccaa ctacctctga tagttgagtc gatacttcgg      4620
cgatcaccgc ttccctcatg atgtttaact ttgttttagg gcgactgccc tgctgcgtaa      4680
catcgttgct gctccataac atcaaacatc gacccacggc gtaacgcgct tgctgcttgg      4740
atgcccgagg catagactgt accccaaaaa aacagtcata acaagccatg aaaaccgcca      4800
ctgcgccgtt accaccgctg cgttcggtca aggttctgga ccagttgcgt gagcgcatac      4860
gctacttgca ttacagctta cgaaccgaac aggcttatgt ccactgggtt cgtgccttca      4920 tccgttttcca cggtgtgcgt cacccggcaa ccttgggcag cagcgaagtc gaggcatttc      4980
tgtcctggct ggcgaacgag cgcaaggttt cggtctccac gcatcgtcag gcattggcgg      5040
ccttgctgtt cttctacggc aaggtgctgt gcacggatct gccctggctt caggagatcg      5100
gaagacctcg gccgtcgcgg cgcttgccgg tggtgctgac cccggatgaa gtggttcgca      5160
tcctcggttt tctggaaggc gagcatcgtt tgttcgccca gcttctgtat ggaacgggca      5220
tgcggatcag tgagggtttg caactgcggg tcaaggatct ggatttcgat cacggcacga      5280
tcatcgtgcg ggagggcaag ggctccaagg atcgggcctt gatgttaccc gagagcttgg      5340
cacccagcct gcgcgagcag gggaattgat ccggtggatg accttttgaa tgacccttaa      5400
tagattatat tactaattaa ttggggaccc tagaggtccc cttttttatt ttaaaaattt      5460
tttcacaaaa cggtttacaa gcataacggg ttttgctgcc cgcaaacggg ctgttctggt      5520
gttgctagtt tgttatcaga atcgcagatc cggcttcagg tttgccggct gaaagcgcta      5580
tttcttccag aattgccatg atttttttccc cacgggaggc gtcactggct cccgtgttgt      5640
cggcagcttt gattcgataa gcagcatcgc ctgtttcagg ctgtctatgt gtgactgttg      5700
agctgtaaca agttgtctca ggtgttcaat ttcatgttct agttgctttg ttttactggt      5760
ttcacctgtt ctattaggtg ttacatgctg ttcatctgtt acattgtcga tctgttcatg      5820
gtgaacagct ttaaatgcac caaaaactcg taaaagctct gatgtatcta tcttttttac      5880
accgttttca tctgtgcata tggacagttt tcccttttgat atctaacggt gaacagttgt      5940
tctacttttg tttgttagtc ttgatgcttc actgatagat acaagagcca taagaacctc      6000
agatccttcc gtatttagcc agtatgttct ctagtgtggt tcgttgtttt tgcgtgagcc      6060
atgagaacga accattgaga tcatgcttac tttgcatgtc actcaaaaat tttgcctcaa      6120
aactggtgag ctgaattttt gcagttaaag catcgtgtag tgttttttctt agtccgttac      6180 gtaggtagga atctgatgta atggttgttg gtattttgtc accattcatt tttatctggt      6240
tgttctcaag ttcggttacg agatccattt gtctatctag ttcaacttgg aaaatcaacg      6300
tatcagtcgg gcggcctcgc ttatcaacca ccaatttcat attgctgtaa gtgtttaaat      6360 cttttacttat tggtttcaaa acccattggt taagcctttt aaactcatgg tagttatttt      6420
caagcattaa catgaactta aattcatcaa ggctaatctc tatatttgcc ttgtgagttt      6480
tcttttgtgt tagttctttt aataaccact cataaatcct catagagtat ttgttttcaa      6540
aagacttaac atgttccaga ttatatttta tgaattttttt taactggaaa agataaggca      6600
atatctcttc actaaaaaact aattctaatt tttcgcttga gaacttggca tagttttgtcc      6660 actggaaaat ctcaaagcct ttaaccaaag gattcctgat ttccacagtt ctcgtcatca      6720
```

```
gctctctggt tgctttagct aatacaccat aagcattttc cctactgatg ttcatcatct      6780
gagcgtattg gttataagtg aacgataccg tccgttcttt ccttgtaggg ttttcaatcg      6840
tggggttgag tagtgccaca cagcataaaa ttagcttggt ttcatgctcc gttaagtcat      6900
agcgactaat cgctagttca tttgctttga aaacaactaa ttcagacata catctcaatt      6960
ggtctaggtg attttaatca ctataccaat tgagatgggc tagtcaatga taattactag      7020
tccttttcct ttgagttgtg ggtatctgta aattctgcta gacctttgct ggaaaacttg      7080
taaattctgc tagaccctct gtaaattccg ctagaccttt gtgtgttttt tttgttttata     7140 ttcaagtggt tataatttat agaataaaga aagaataaaa aaagataaaa agaatagatc      7200
ccagccctgt gtataactca ctactttagt cagttccgca gtattacaaa aggatgtcgc      7260
aaacgctgtt tgctcctcta caaaacagac cttaaaaccc taaaggctta agtagcaccc     7320
tcgcaagctc gggcaaatcg ctgaatattc cttttgtctc cgaccatcag gcacctgagt     7380
cgctgtcttt ttcgtgacat tcagttcgct gcgctcacgg ctctggcagt gaatgggggt     7440
aaatggcact acaggcgcct tttatggatt catgcaagga aactacccat aatacaagaa     7500
aagcccgtca cgggcttctc agggcgtttt atggcgggtc tgctatgtgg tgctatctga    7560 cttttttgctg ttcagcagtt cctgccctct gattttccag tctgaccact tcggattatc     7620
ccgtgacagg tcattcagac tggctaatgc acccagtaag gcagcggtat catcaacagg     7680
cttacccgtc ttactgtcaa c                                                7701

<210> SEQ ID NO 26
<211> LENGTH: 3888
<212> TYPE: DNA
<213> ORGANISM: Artificial Sequence
<220> FEATURE:
<223> OTHER INFORMATION: plasmid

<400> SEQUENCE: 26
tgcgccgcta cagggcgcgt ccattcgcca ttcaggctgc gcaactgttg ggaagggcga       60
tcggtgcggg cctcttcgct attacgccag tttgggggtg agttcatgaa gtttcgtcgc     120
agcggcagat tggtggactt aacaaattat ttgttaaccc atccgcacga gttaataccg     180 ctaaccttttt tctctgagcg gtatgaatct gcaaaatcat cgatcagtga agatttaaca     240
attattaaac aaacctttga acagcagggg attggtactt tgcttactgt tcccggagct    300
gccggaggcg ttaaatatat tccgaaaatg aagcaggctg aagctgaaga gtttgtgcag     360
acacttggac agtcgctggc aaatcctgag cgtatccttc cgggcggtta tgtatattta     420
acggatatct taggaaagcc atctgtactc tccaaggtag ggaagctgtt tgcttccgtg     480
tttgcagagc gcgaaattga tgttgtcatg accgttgcca cgaaaggcat ccctcttgcg     540
tacgcagctg caagctattt gaatgtgcct gttgtgatcg ttcgtaaaga caataaggta     600
acagagggct ccacagtcag cattaattac gtttcaggct cctcaaaccg cattcaaaca     660
atgtcacttg cgaaaagaag catgaaaacg ggttcaaacg tactcattat tgatgacttt     720
atgaaagcag gcggcaccat taatggtatg attaacctgt tggatgagtt taacgcaaat     780
gtggcgggaa tcggcgtctt agttgaagcc gaaggagtag atgaacgtct tgttgacgaa     840
tatatgtcac ttcttactct ttcaaccatc aacatgaaag agaagtccat tgaaattcag     900
aatggcaatt ttctgcgttt ttttaaagac aatcttttaa agaatggaga gacagaatca     960
tgacaaaagc agtccacaca aaacatgccc agcggcaat cgggcctat tcacaaggga    1020 ttatcgtcaa caatatgttt tacagctcag gccaaatccc tttgactcct tcaggcgaaa    1080
```

```
tggtgaatgg cgatattaag gagcagactc atcaagtatt cagcaattta aaggcggttc    1140
tggaagaagc gggtgcttct tttgaaacag ttgtaaaagc aactgtattt atcgcggata    1200
tggaacagtt tgcggaagta acgaagtgt acggacaata ttttgacact cacaaaccgg     1260
cgagatcttg tgttgaagtc gcgagactcc cgaaggatgc gttagtcgag atcgaagtta   1320
ttgcactggt gaaataataa gaaaagtgat tctgggagag ccgggatcac ttttttattt   1380
accttatgcc cgaaatgaaa gctttatgac cctgcattaa tgaatcggcc aacgcgcggg   1440
gagaggcggt ttgcgtattg ggcgctcttc cgcttcctcg ctcactgact cgctgcgctc   1500
ggtcgttcgg ctgcggcgag cggtatcagc tcactcaaag gcggtaatac ggttatccac   1560
agaatcaggg gataacgcag gaaagaacat gtgagcaaaa ggccagcaaa aggccaggaa   1620
ccgtaaaaag gccgcgttgc tggcgttttt cgataggctc cgccccctg acgagcatca    1680 caaaatcga cgctcaagtc agaggtggcg aaacccgaca ggactataaa gataccaggc    1740
gtttccccct ggaagctccc tcgtgcgctc tcctgttccg accctgccgc ttaccggata   1800
cctgtccgcc tttctccctt cgggaagcgt ggcgctttct catagctcac gctgtaggta   1860
tctcagttcg gtgtaggtcg ttcgctccaa gctgggctgt gtgcacgaac cccccgttca   1920
gcccgaccgc tgcgccttat ccggtaacta tcgtcttgag tccaacccgg taagacacga   1980
cttatcgcca ctggcagcag ccactggtaa caggattagc agagcgaggt atgtaggcgg   2040
tgctacagag ttcttgaagt ggtggcctaa ctacggctac actagaagga cagtatttgg   2100
tatctgcgct ctgctgaagc cagttacctt cggaaaaaga gttggtagct cttgatccgg   2160
caaacaaacc accgctggta gcggtggttt ttttgtttgc aagcagcaga ttacgcgcag   2220
aaaaaaagga tctcaagaag atcctttgat cttttctacg gggtctgacg ctcagtggaa   2280
cgaaaactca cgttaaggga ttttggtcat gagattatca aaaaggatct tcacctagat   2340
ccttttaaat taaaaatgaa gttttaaatc aatctaaagt atatatgagt aaacttggtc   2400
tgacagttac caatgcttaa tcagtgaggc acctatctca gcgatctgtc tatttcgttc   2460
atccatagtt gcctgactcc ccgtcgtgta gataactacg atacgggagg gcttaccatc   2520
tggccccagt gctgcaatga taccgcgaga cccacgctca ccggctccag atttatcagc   2580
aataaaccag ccagccggaa gggccgagcg cagaagtggt cctgcaactt tatccgcctc   2640
catccagtct attaattgtt gccgggaagc tagagtaagt agttcgccag ttaatagttt   2700
gcgcaacgtt gttggcattg ctacaggcat cgtggtgtca cgctcgtcgt ttggtatggc   2760
ttcattcagc tccggttccc aacgatcaag gcgagttaca tgatccccca tgttgtgcaa   2820
aaaagcggtt agctccttcg gtcctccgat cgttgtcaga agtaagttgg ccgcagtgtt   2880
atcactcatg gttatggcag cactgcataa ttctcttact gtcatgccat ccgtaagatg   2940
cttttctgtg actggtgagt actcaaccaa gtcattctga gaataccgcg cccgcgacc    3000 gagttgctct tgcccggcgt caatacggga taatagtgta tgacatagca gaactttaaa   3060
agtgctcatc attggaaaac gttcttcggg gcgaaaactc tcaaggatct accgctgtt    3120 gagatccagt tcgatgtaac ccactcgtgc acccaactga tcttcagcat ctttacttt    3180 caccagcgtt tctgggtgag caaaaacagg aaggcaaaat gccgcaaaaa agggaataag   3240
ggcgacacgg aaatgttgaa tactcatact cttccttttt caatattatt gaagcattta   3300
tcagggttat tgtctcatga gcggatacat atttgaatgt atttagaaaa ataaacaaat   3360 agggggttccg cgcacatttc cccgaaaagt gccacctgta tgcggtgtga ataccgcac   3420 agatgcgtaa ggagaaaata ccgcatcagg cgaaattgta aacgttaata ttttgttaaa   3480
```

-continued

| | |
|---|---|
| attcgcgtta aatatttgtt aaatcagctc atttttaac caataggccg aaatcggcaa | 3540 |
| aatcccttat aaatcaaaag aatagaccga gatagggttg agtgttgttc cagtttggaa | 3600 |
| caagagtcca ctattaaaga acgtggactc caacgtcaaa gggcgaaaaa ccgtctatca | 3660 |
| gggcgatggc ccactacgtg aaccatcacc caaatcaagt tttttgcggt cgaggtgccg | 3720 |
| taaagctcta atcggaacc ctaaagggag cccccgattt agagcttgac ggggaaagcc | 3780 |
| ggcgaacgtg gcgagaaagg aagggaagaa agcgaaagga gcgggcgcta gggcgctggc | 3840 |
| aagtgtagcg gtcacgctgc gcgtaaccac cacacccgcc gcgcttaa | 3888 |

<210> SEQ ID NO 27
<211> LENGTH: 4606
<212> TYPE: DNA
<213> ORGANISM: Artificial Sequence
<220> FEATURE:
<223> OTHER INFORMATION: Description of Artificial Sequence:plasmid

<400> SEQUENCE: 27

| | |
|---|---|
| tgcgccgcta cagggcgcgt ccattcgcca ttcaggctgc gcaactgttg ggaagggcga | 60 |
| tcggtgcggg cctcttcgct attacgccag ctggcgaaag ggggatgtgc tgcaaggcga | 120 |
| ttaagttggg taacgccagg gttttcccag tcacgacgtt gtaaaacgac ggccagtgaa | 180 |
| ttgtaatacg actcactata gggcgaattg ggcccgacgt cgcatgctcc cggccgccat | 240 |
| ggccgcggga tgcggccgcg tcgacgtgaa ataccgcaca gatgcgtaag gagaaaatac | 300 |
| cgcatcaggc gataaaccca gcgaaccatt tgaggtgata ggtaagatta taccgaggta | 360 |
| tgaaaacgag aattggacct ttacagaatt actctatgaa gcgccatatt taaaaagcta | 420 |
| ccaagacgaa gaggatgaag aggatgagga gcagattgc cttgaatata ttgacaatac | 480 |
| tgataagata atatatcttt tatatagaag atatcgccgt atgtaaggat ttcaggggggc | 540 |
| aaggcatagg cagcgcgctt atcaatatat ctatagaatg gcaaagcat aaaaacttgc | 600 |
| atggactaat gcttgaaacc caggacaata accttatagc ttgtaaattc tatcataatt | 660 |
| gtggtttcaa aatcggctcc gtcgatacta tgttatacgc caactttcaa aacaactttg | 720 |
| aaaaagctgt tttctggtat ttaaggtttt agaatgcaag gaacagtgaa ttggagttcg | 780 |
| tcttgttata attagcttct gggggtatct ttaaatactg tagaaaagag gaaggaaata | 840 |
| ataaatggct aaaatgagaa tatcaccgga attgaaaaaa ctgatcgaaa aataccgctg | 900 |
| cgtaaaagat acggaaggaa tgtctcctgc taaggtatat aagctggtgg gagaaaatga | 960 |
| aaacctatat ttaaaaatga cggacagccg gtataaaggg accacctatg atgtggaacg | 1020 |
| ggaaaaggac atgatgctat ggctggaagg aaagctgcct gttccaaagg tcctgcactt | 1080 |
| tgaacggcat gatggctgga gcaatctgct catgagtgag gccgatggcg tcctttgctc | 1140 |
| ggaagagtat gaagatgaac aaagccctga aagattatc gagctgtatg cggagtgcat | 1200 |
| caggctcttt cactccatcg acatatcgga ttgtccctat acgaatagct tagacagccg | 1260 |
| cttagccgaa ttggattact tactgaataa cgatctggcc gatgtggatt gcgaaaactg | 1320 |
| ggaagaagac actccattta aagatccgcg cgagctgtat gatttttaa agacggaaaa | 1380 |
| gcccgaagag gaacttgtct tttcccacgg cgacctggga gacagcaaca tctttgtgaa | 1440 |
| agatggcaaa gtaagtggct ttattgatct gggagaagc ggcagggcgg acaagtggta | 1500 |
| tgacattgcc ttctgcgtcc ggtcgatcag ggaggatatc ggggaagaac agtatgtcga | 1560 |
| gctattttt gacttactgg ggatcaagcc tgattgggag aaaataaaat attatatttc | 1620 |
| actggatgaa ttgttttagt acctagattt agatgtctaa aaagctttaa ctacaagctt | 1680 |

```
tttagacatc taatcttttc tgaagtacat ccgcaactgt ccatactctg atgttttata   1740
tcttttctaa aagttcgcta gataggggtc ccgagcgcct acgaggaatt tgtatcgcca   1800
ttcgccattc aggctgcgca actgttggga agggcgatcg gtgcgggtac cgggatcact   1860
agtgcggccg cctgcaggtc gaccatatgg gagagctccc aacgcgttgg atgcatagct   1920
tgagtattct atagtgtcac ctaaatagct tggcgtaatc atggtcatag ctgtttcctg   1980
tgtgaaattg ttatccgctc acaattccac acaacatacg agccggaagc ataaagtgta   2040
aagcctgggg tgcctaatga gtgagctaac tcacattaat tgcgttgcgc tcactgcccg   2100
ctttccagtc gggaaacctg tcgtgccagc tgcattaatg aatcggccaa cgcgcgggga   2160
gaggcggttt gcgtattggg cgctcttccg cttcctcgct cactgactcg ctgcgctcgg   2220
tcgttcggct gcggcgagcg gtatcagctc actcaaaggc ggtaatacgg ttatccacag   2280
aatcagggga taacgcagga aagaacatgt gagcaaaagg ccagcaaaag gccaggaacc   2340
gtaaaaaggc cgcgttgctg gcgtttttcg ataggctccg ccccccctgac gagcatcaca   2400
aaaatcgacg ctcaagtcag aggtggcgaa acccgacagg actataaaga taccaggcgt   2460
ttccccctgg aagctccctc gtgcgctctc ctgttccgac cctgccgctt accggatacc   2520
tgtccgcctt tctcccttcg ggaagcgtgg cgctttctca tagctcacgc tgtaggtatc   2580
tcagttcggt gtaggtcgtt cgctccaagc tgggctgtgt gcacgaaccc cccgttcagc   2640
ccgaccgctg cgccttatcc ggtaactatc gtcttgagtc caacccggta agacacgact   2700
tatcgccact ggcagcagcc actggtaaca ggattagcag agcgaggtat gtaggcggtg   2760
ctacagagtt cttgaagtgg tggcctaact acggctacac tagaaggaca gtatttggta   2820
tctgcgctct gctgaagcca gttaccttcg gaaaaagagt tggtagctct tgatccggca   2880
aacaaaccac cgctggtagc ggtggttttt ttgtttgcaa gcagcagatt acgcgcagaa   2940
aaaaaggatc tcaagaagat cctttgatct tttctacggg gtctgacgct cagtggaacg   3000
aaaactcacg ttaagggatt ttggtcatga gattatcaaa aaggatcttc acctagatcc   3060
ttttaaatta aaaatgaagt tttaaatcaa tctaaagtat atatgagtaa acttggtctg   3120
acagttacca atgcttaatc agtgaggcac ctatctcagc gatctgtcta tttcgttcat   3180
ccatagttgc ctgactcccc gtcgtgtaga taactacgat acgggagggc ttaccatctg   3240
gccccagtgc tgcaatgata ccgcgagacc cacgctcacc ggctccagat ttatcagcaa   3300
taaaccagcc agccggaagg gccgagcgca gaagtggtcc tgcaacttta tccgcctcca   3360
tccagtctat taattgttgc cgggaagcta gagtaagtag ttcgccagtt aatagtttgc   3420
gcaacgttgt tggcattgct acaggcatcg tggtgtcacg ctcgtcgttt ggtatggctt   3480
cattcagctc cggttcccaa cgatcaaggc gagttacatg atccccatg ttgtgcaaaa   3540
aagcggttag ctccttcggt cctccgatcg ttgtcagaag taagttggcc gcagtgttat   3600
cactcatggt tatggcagca ctgcataatt ctcttactgt catgccatcc gtaagatgct   3660
tttctgtgac tggtgagtac tcaaccaagt cattctgaga ataccgcgcc cggcgaccga   3720
gttgctcttg cccggcgtca atacgggata ataccgtatg acatagcaga actttaaaag   3780
tgctcatcat tggaaaacgt tcttcggggc gaaaactctc aaggatctta ccgctgttga   3840
gatccagttc gatgtaaccc actcgtgcac ccaactgatc ttcagcatct tttactttca   3900
ccagcgtttc tgggtgagca aaaacaggaa ggcaaaatgc cgcaaaaaag ggaataaggg   3960
cgacacggaa atgttgaata ctcatactct tcctttttca atattattga agcatttatc   4020
agggttattg tctcatgagc ggatacatat ttgaatgtat ttagaaaaat aaacaaatag   4080
```

-continued

| | |
|---|---|
| gggttccgcg cacatttccc cgaaaagtgc cacctgtatg cggtgtgaaa taccgcacag | 4140 |
| atgcgtaagg agaaaatacc gcatcaggcg aaattgtaaa cgttaatatt ttgttaaaat | 4200 |
| tcgcgttaaa tatttgttaa atcagctcat tttttaacca ataggccgaa atcggcaaaa | 4260 |
| tcccttataa atcaaaagaa tagaccgaga tagggttgag tgttgttcca gtttggaaca | 4320 |
| agagtccact attaaagaac gtggactcca acgtcaaagg gcgaaaaacc gtctatcagg | 4380 |
| gcgatggccc actacgtgaa ccatcaccca aatcaagttt tttgcggtcg aggtgccgta | 4440 |
| aagctctaaa tcggaaccct aaagggagcc cccgatttag agcttgacgg ggaaagccgg | 4500 |
| cgaacgtggc gagaaaggaa gggaagaaag cgaaaggagc gggcgctagg gcgctggcaa | 4560 |
| gtgtagcggt cacgctgcgc gtaaccacca cacccgccgc gcttaa | 4606 |

<210> SEQ ID NO 28
<211> LENGTH: 5399
<212> TYPE: DNA
<213> ORGANISM: Artificial Sequence
<220> FEATURE:
<223> OTHER INFORMATION: Description of Artificial Sequence:plasmid

<400> SEQUENCE: 28

| | |
|---|---|
| tgcgccgcta cagggcgcgt ccattcgcca ttcaggctgc gcaactgttg ggaagggcga | 60 |
| tcggtgcggg cctcttcgct attacgccag tttgggggtg agttcatgaa gtttcgtcgc | 120 |
| agcggcagat tggtggactt aacaaattat ttgttaaccc atccgcacga gttaataccg | 180 |
| ctaaccttt tctctgagcg gtatgaatct gcaaaatcat cgatcagtga agatttaaca | 240 |
| attattaaac aaacctttga acagcagggg attggtactt tgcttactgt tcccggagct | 300 |
| gccggaggcg ttaaatatat tccgaaaatg aagcaggctg aagctgaaga gtttgtgcag | 360 |
| acacttggac agtcgctggc aaatcctgag cgtatccttc cggcggtta tgtatattta | 420 |
| acggatatct taggaaagcc atctgtactc tccaaggtag ggaagctgtt tgcttccgtg | 480 |
| tttgcagagc gcgaaattga tgttgtcatg accgttgcca cgaaaggcat ccctcttgcg | 540 |
| tacgcagctg cggccgcgtc gacaaaccca gtgaaccatt tgaggtgata ggtaagatta | 600 |
| taccgaggta tgaaaacgag aattggacct ttacagaatt actctatgaa gcgccatatt | 660 |
| taaaaagcta ccaagacgaa gaggatgaag aggatgagga ggcagattgc cttgaatata | 720 |
| ttgacaatac tgataagata atatatcttt tatatagaag atatcgccgt atgtaaggat | 780 |
| ttcaggggc aaggcatagg cagcgcgctt atcaatatat ctatagaatg ggcaaagcat | 840 |
| aaaaacttgc atggactaat gcttgaaacc caggacaata accttatagc ttgtaaattc | 900 |
| tatcataatt gtggtttcaa aatcggctcc gtcgatacta tgttatacgc caactttcaa | 960 |
| aacaactttg aaaaagctgt tttctggtat ttaaggtttt agaatgcaag gaacagtgaa | 1020 |
| ttggagttcg tcttgttata attagcttct tggggtatct ttaaatactg tagaaaagag | 1080 |
| gaaggaaata ataaatggct aaaatgagaa tatcaccgga attgaaaaaa ctgatcgaaa | 1140 |
| aataccgctg cgtaaaagat acggaaggaa tgtctcctgc taaggtatat aagctggtgg | 1200 |
| gagaaaatga aacctatat ttaaaaatga cggacagccg gtataaaggg accacctatg | 1260 |
| atgtggaacg ggaaaaggac atgatgctat ggctggaagg aaagctgcct gttccaaagg | 1320 |
| tcctgcactt tgaacggcat gatggctgga gcaatctgct catgagtgag gccgatggcg | 1380 |
| tcctttgctc ggaagagtat gaagatgaac aaagccctga aaagattatc gagctgtatg | 1440 |
| cggagtgcat caggctcttt cactccatcg acatatcgga ttgtccctat acgaatagct | 1500 |
| tagacagccg cttagccgaa ttggattact tactgaataa cgatctggcc gatgtggatt | 1560 |

```
gcgaaaactg ggaagaagac actccattta aagatccgcg cgagctgtat gattttttaa    1620
agacggaaaa gcccgaagag gaacttgtct tttcccacgg cgacctggga gacagcaaca    1680
tctttgtgaa agatggcaaa gtaagtggct ttattgatct tgggagaagc ggcagggcgg    1740
acaagtggta tgacattgcc ttctgcgtcc ggtcgatcag ggaggatatc ggggaagaac    1800
agtatgtcga gctatttttt gacttactgg ggatcaagcc tgattgggag aaaataaaat    1860
attatatttt actggatgaa ttgttttagt acctagattt agatgtctaa aaagctttaa    1920
ctacaagctt tttagacatc taatcttttc tgaagtacat ccgcaactgt ccatactctg    1980
atgttttata tcttttctaa aagttcgcta gatagggtc ccgagcgcct acgaggaatt    2040
tgtatcacca ggtaccagct gcaagctatt gaatgtgcc tgttgtgatc gttcgtaaag    2100
acaataaggt aacagagggc tccacagtca gcattaatta cgtttcaggc tcctcaaacc    2160
gcattcaaac aatgtcactt gcgaaaagaa gcatgaaaac gggttcaaac gtactcatta    2220
ttgatgactt tatgaaagca ggcggcacca ttaatggtat gattaacctg ttggatgagt    2280
ttaacgcaaa tgtggcggga atcggcgtct tagttgaagc cgaaggagta gatgaacgtc    2340
ttgttgacga atatatgtca cttcttactc tttcaaccat caacatgaaa gagaagtcca    2400
ttgaaattca gaatggcaat tttctgcgtt tttttaaaga caatcttttta aagaatggag    2460 agacagaatc atgacaaaag cagtccacac aaaacatgcc ccagcggcaa tcgggcctta    2520
ttcacaaggg attatcgtca acaatatgtt ttacagctca ggccaaatcc ctttgactcc    2580
ttcaggcgaa atggtgaatg gcgatattaa ggagcagact catcaagtat tcagcaattt    2640
aaaggcggtt ctggaagaag cgggtgcttc ttttgaaaca gttgtaaaag caactgtatt    2700
tatcgcggat atgaacagt ttgcggaagt aaacgaagtg tacggacaat attttgacac    2760
tcacaaaccg gcgagatctt gtgttgaagt cgcgagactc ccgaaggatg cgttagtcga    2820
gatcgaagtt attgcactgg tgaaataata agaaaagtga ttctgggaga gccgggatca    2880
cttttttatt taccttatgc ccgaaatgaa agctttatga ccctgcatta atgaatcggc    2940
caacgcgcgg ggagaggcgg tttgcgtatt ggcgctctt ccgcttcctc gctcactgac    3000
tcgctgcgct cggtcgttcg gctgcggcga gcggtatcag ctcactcaaa ggcggtaata    3060
cggttatcca cagaatcagg ggataacgca ggaaagaaca tgtgagcaaa aggccagcaa    3120
aaggccagga accgtaaaaa ggccgcgttg ctggcgtttt tcgataggct ccgcccccct    3180
gacgagcatc acaaaaatcg acgctcaagt cagaggtggc gaaacccgac aggactataa    3240
agataccagg cgtttccccc tggaagctcc ctcgtgcgct ctcctgttcc gaccctgccg    3300
cttaccggat acctgtccgc ctttctccct tcgggaagcg tggcgctttc tcatagctca    3360
cgctgtaggt atctcagttc ggtgtaggtc gttcgctcca agctgggctg tgtgcacgaa    3420
ccccccgttc agcccgaccg ctgcgcctta tccggtaact atcgtcttga gtccaacccg    3480
gtaagacacg acttatcgcc actggcagca gccactggta acaggattag cagagcgagg    3540
tatgtaggcg gtgctacaga gttcttgaag tggtggccta actacggcta cactagaagg    3600
acagtatttg gtatctgcgc tctgctgaag ccagttacct tcggaaaaag agttggtagc    3660
tcttgatccg gcaaacaaac caccgctggt agcggtggtt ttttgtttg caagcagcag    3720 attacgcgca gaaaaaaagg atctcaagaa gatcctttga tcttttctac ggggtctgac    3780
gctcagtgga acgaaaactc acgttaaggg attttggtca tgagattatc aaaaaggatc    3840
ttcacctaga tccttttaaa ttaaaaatga agttttaaat caatctaaag tatatatgag    3900
taaacttggt ctgacagtta ccaatgctta atcagtgagg cacctatctc agcgatctgt    3960
```

```
ctatttcgtt catccatagt tgcctgactc cccgtcgtgt agataactac gatacgggag    4020
ggcttaccat ctggccccag tgctgcaatg ataccgcgag acccacgctc accggctcca    4080
gatttatcag caataaacca gccagccgga agggccgagc gcagaagtgg tcctgcaact    4140
ttatccgcct ccatccagtc tattaattgt tgccgggaag ctagagtaag tagttcgcca    4200
gttaatagtt tgcgcaacgt tgttggcatt gctacaggca tcgtggtgtc acgctcgtcg    4260
tttggtatgg cttcattcag ctccggttcc caacgatcaa ggcgagttac atgatccccc    4320
atgttgtgca aaaaagcggt tagctccttc ggtcctccga tcgttgtcag aagtaagttg    4380
gccgcagtgt tatcactcat ggttatggca gcactgcata attctcttac tgtcatgcca    4440
tccgtaagat gcttttctgt gactggtgag tactcaacca agtcattctg agaataccgc    4500
gcccggcgac cgagttgctc ttgcccggcg tcaatacggg ataatagtgt atgacatagc    4560
agaactttaa aagtgctcat cattggaaaa cgttcttcgg ggcgaaaact ctcaaggatc    4620
ttaccgctgt tgagatccag ttcgatgtaa cccactcgtg cacccaactg atcttcagca    4680
tcttttactt tcaccagcgt ttctgggtga gcaaaaacag gaaggcaaaa tgccgcaaaa    4740
aagggaataa gggcgacacg gaaatgttga atactcatac tcttcctttt tcaatattat    4800
tgaagcattt atcagggtta ttgtctcatg agcggataca tatttgaatg tatttagaaa    4860
aataaacaaa taggggttcc gcgcacattt ccccgaaaag tgccacctgt atgcggtgtg    4920
aaataccgca cagatgcgta aggagaaaat accgcatcag gcgaaattgt aaacgttaat    4980
attttgttaa aattcgcgtt aaatatttgt taaatcagct cattttttaa ccaataggcc    5040
gaaatcggca aaatccctta taaatcaaaa gaatagaccg agatagggtt gagtgttgtt    5100
ccagtttgga acaagagtcc actattaaag aacgtggact ccaacgtcaa agggcgaaaa    5160
accgtctatc agggcgatgg cccactacgt gaaccatcac ccaaatcaag ttttttgcgg    5220
tcgaggtgcc gtaaagctct aaatcggaac cctaaaggga gcccccgatt tagagcttga    5280
cggggaaagc cggcgaacgt ggcgagaaag gaagggaaga agcgaaagg agcgggcgct    5340 agggcgctgg caagtgtagc ggtcacgctg cgcgtaacca ccacacccgc cgcgcttaa    5399
```

<210> SEQ ID NO 29
<211> LENGTH: 6805
<212> TYPE: DNA
<213> ORGANISM: Artificial Sequence
<220> FEATURE:
<223> OTHER INFORMATION: Description of Artificial Sequence:plasmid

<400> SEQUENCE: 29

```
ttgcggccgc ttcgaaagct gtaatataaa aaccttcttc aactaacggg gcaggttagt     60
gacattagaa aaccgactgt aaaaagtaca gtcggcatta tctcatatta taaaagccag    120
tcattaggcc tatctgacaa ttcctgaata gagttcataa acaatcctgc atgtaaacca    180
tcacaaacag aatgatgtac ctgtaaagat agcggtaaat atattgaatt acctttatta    240
atgaattttc ctgctgtaat aatgggtaga aggtaattac tattattatt gatatttaag    300
ttaaacccag taaatgaagt ccatggaata atagaaagag aaaaagcatt ttcaggtata    360
ggtgttttgg gaaacaattt ccccgaacca ttatatttct ctacatcaga aaggtataaa    420
tcataaaact ctttgaagtc attctttaca ggagtccaaa taccagagaa tgttttagat    480
acaccatcaa aaattgtata agtggctctc aacttatccc aataacctaa ctctccgtcg    540
ctattgtaac cagttctaaa agctgtattt gagtttatca cccttgtcac taagaaaata    600
aatgcagggt aaaatttata tccttcttgt tttatgtttc ggtataaaac actaatatca    660
```

```
atttctgtgg ttatactaaa agtcgtttgt tggttcaaat aatgattaaa tatctctttt    720
ctcttccaat tgtctaaatc aattttatta aagttcattt gatatgcctc ctaaattttt    780
atctaaagtg aatttaggag gcttacttgt ctgctttctt cattagaatc aatcctttt    840
taaaagtcaa tattactgta acataaatat atattttaaa aatatcccac tttatccaat    900
tttcgtttgt tgaactaatg ggtgcttag ttgaagaata aagaccacat taaaaaatgt     960
ggtcttttgt gttttttaa aggatttgag cgtagcgaaa aatccttttc tttcttatct     1020
tgataataag ggtaactatt gaattcggta ccaagagttt gtagaaacgc aaaaaggcca   1080
tccgtcagga tggccttctg cttaatttga tgcctggcag tttatggcgg gcgtcctgcc   1140
cgccaccctc cgggccgttg cttcgcaacg ttcaaatccg ctcccggcgg atttgtccta   1200
ctcaggagag cgttcaccga caaacaacag ataaaacgaa aggcccagtc tttcgactga   1260
gcctttcgtt ttatttgatg cctggcagtt ccctactctc gcatgggag accccacact    1320
accatcggcg ctacggcgtt tcacttctga gttcggcatg gggtcaggtg ggaccaccgc   1380
gctactgccg ccaggcaaat tctgttttat cagaccgctt ctgcgttctg atttaatctg   1440
tatcaggctg aaaatcttct ctcatccgcc aaaacaggat ccaattatgg cagatcaatg   1500
agcttcacag acacaatatc agggacattt gttagttctt tcacaattt atcttccaga    1560
tgtctgtcaa aggaaagcat catgatggct tctccgcctt tttccttacg gccaacctgc   1620
atagttgcaa tgttaatatc attatctccg agaatacgtc ctactcggcc gatgacacct   1680
gttgtatctt gatgctggat atacaccaag tgaccagtcg gataaaaatc aatattaaat   1740
ccattgatct cgacaattcg ttctccgaaa tgaggaatat acgtagccgt tacagtaaag   1800
gtgctgcggt ctcctgtcac ttttacgctg atgcagttat cgtatccaga ttcagaagag   1860
gaaatttttt cactgaagct aatgccgcgt tcttttgcga caccccggc attgacctca    1920
ttaacagtag agtctacgcg cggttttaaa aagcctgaca gaagggcttt tgtaatgaac   1980
gatgtttcaa gtttagcaat tgtgccttca tattgaatgg caacatcctg tactggttct   2040
ttcatgcact gtgatacaag gctgccaatt tttcctgcaa tttgatggta aggcttaatt   2100
ttagcaaatt catcttttgt catggcaggc aggttgatag ctgacatgac aggcaggcct   2160
tttgcgaact gcagaacttc ttctgacact tgggcggcga cattgagctg tgcttctttc   2220
gttgatgctc ccaagtgagg agtggcaatg actaatggat gatcaacaag tttgttgtca   2280
actggcggtt cgacttcgaa aacgtcaagc gctgctcccg caacatgccc gttttccaaa   2340
gcttcgagaa gtgctgcttc atcgataatt ccgcctcgcg cacagttaat taagcgaacg   2400
ccttttttcg ttttgcaat cgtttctta ttcaataagc ttttgtttc ttttgttaaa      2460
ggcgtgtgaa cggtaatgat atccgcactt tcaagcactt cttcaaatgt acggctgttt   2520
acgccgattt ttttcgctct tcttccgtt aagaaaggat caaaaacgtg cacagtcata    2580
ccgaacgctc ctcgacgctg tgcaatttca cttccgattc ggcctaatcc tacaatacca   2640
agcgttttc cataaagctc tgaaccgaca taagctgtgc ggttccactc tctggatttc    2700
actgagatat tagcctgcgg aatgtgtctc attaaagaag agatcattgc aaatgtatgc   2760
tcagctgtcg aaatggtgtt gccgttcgga gcattgatca cgattacccc gtgtttcgta   2820
gcctcatcaa tatcgatatt atcgacaccg acaccggctc ttccgacaat ttttaaagaa   2880
gtcattttgt tgaaaggtc ttctgttact tttgtcgcgc ttcgcaccaa aagagcatca    2940
aaagtatgta attcatcttc tgcatctgct acgtttttt gaacgatttc aataaagtct    3000
gattcaataa gtggctgtaa accgtcgttg ctcattttgt ctgagaccaa tactcgaaac   3060
```

```
atgttttctc ctcctctaga gcgtcctgct gttgttaaga ttattatacc acaccttgta    3120
gataaagtca acaacttttt gcaaaatttt tcaggaattt tagcagaggt tgttctggat    3180
gtagaacaaa acatctttcc gctcttgtgc tgttaggata tctttcttgg aagctaggta    3240
ggcctcgagt tatggcagtt ggttaaaagg aaacaaaaag accgttttca cacaaaacgg    3300 tcttttcga tttcttttta cagtcacagc cacttttgca aaaccggac agcttcatgc     3360 cttataactg ctgtttcggt cgacctgcag gcatgcaagc ttcgcgaagc ggccgccgac    3420
gcgaggctgg atggccttcc ccattatgat tcttctcgct tccggcggca tcgggatgcc    3480
cgcgttgcag gccatgctgt ccaggcaggt agatgacgac catcagggac agcttcaagg    3540
atcgctcgcg gctcttacca gcctaacttc gatcactgga ccgctgatcg tcacggcgat    3600
ttatgccgcc tcggcgagca catggaacgg gttggcatgg attgtaggcg ccgccctata    3660
ccttgtctgc ctccccgcgt tgcgtcgcgg tgcatggagc cgggccacct cgacctgaat    3720
ggaagccggc ggcacctcgc taacggattc accactccaa gaattggagc caatcaattc    3780
ttgcggagaa ctgtgaatgc gcaaaccaac ccttggcaga acatatccat cgcgtccgcc    3840
atctccagca gccgcacgcg gcgcatctcg ggcagcgttg ggtcctggcc acgggtgcgc    3900
atgatcgtgc tcctgtcgtt gaggacccgg ctaggctggc ggggttgcct tactggttag    3960
cagaatgaat caccgatacg cgagcgaacg tgaagcgact gctgctgcaa acgtctgcg     4020 acctgagcaa caacatgaat ggtcttcggt ttccgtgttt cgtaaagtct ggaaacgcgg    4080
aagtcagcgc cctgcaccat tatgttccgg atctgcatcg caggatgctg ctggctaccc    4140
tgtggaacac ctacatctgt attaacgaag cgctggcatt gaccctgagt gattttctc    4200 tggtcccgcc gcatccatac cgccagttgt ttaccctcac aacgttccag taaccgggca    4260
tgttcatcat cagtaacccg tatcgtgagc atcctctctc gtttcatcgg tatcattacc    4320
cccatgaaca gaaattcccc cttacacgga ggcatcaagt gaccaaacag gaaaaaaccg    4380
cccttaacat ggcccgcttt atcagaagcc agacattaac gcttctggag aaactcaacg    4440
agctggacgc ggatgaacag gcagacatct gtgaatcgct tcacgaccac gctgatgagc    4500
tttaccgcag ctgcctcgcg cgtttcggtg atgacggtga aaacctctga cacatgcagc    4560
tcccggagac ggtcacagct tgtctgtaag cggatgccgg gagcagacaa gcccgtcagg    4620
gcgcgtcagc gggtgttggc gggtgtcggg gcgcagccat gacccagtca cgtagcgata    4680
gcggagtgta tactggctta actatgcggc atcagagcag attgtactga gagtgcacca    4740
tatgcggtgt gaaataccgc acagatgcgt aaggagaaaa taccgcatca ggcgctcttc    4800
cgcttcctcg ctcactgact cgctgcgctc ggtcgttcgg ctgcggcgag cggtatcagc    4860
tcactcaaag gcggtaatac ggttatccac agaatcaggg gataacgcag aaagaacat     4920 gtgagcaaaa ggccagcaaa aggccaggaa ccgtaaaaag gccgcgttgc tggcgttttt    4980
ccataggctc cgcccccctg acgagcatca caaaaatcga cgctcaagtc agaggtggcg    5040
aaacccgaca ggactataaa gataccaggc gtttccccct ggaagctccc tcgtgcgctc    5100
tcctgttccg accctgccgc ttaccggata cctgtccgcc tttctccctt cgggaagcgt    5160
ggcgctttct catagctcac gctgtaggta tctcagttcg gtgtaggtcg ttcgctccaa    5220
gctgggctgt gtgcacgaac cccccgttca gcccgaccgc tgcgccttat ccggtaacta    5280
tcgtcttgag tccaacccgg taagacacga cttatcgcca ctggcagcag ccactggtaa    5340
caggattagc agagcgaggt atgtaggcgg tgctacagag ttcttgaagt ggtggcctaa    5400
ctacggctac actagaagga cagtatttgg tatctgcgct ctgctgaagc cagttacctt    5460
```

```
cggaaaaaga gttggtagct cttgatccgg caaacaaacc accgctggta gcggtggttt      5520
ttttgtttgc aagcagcaga ttacgcgcag aaaaaaagga tctcaagaag atcctttgat      5580
cttttctacg gggtctgacg ctcagtggaa cgaaaactca cgttaaggga ttttggtcat      5640
gagattatca aaaaggatct tcacctagat ccttttaaat taaaaatgaa gttttaaatc      5700
aatctaaagt atatatgagt aaacttggtc tgacagttac caatgcttaa tcagtgaggc      5760
acctatctca gcgatctgtc tatttcgttc atccatagtt gcctgactcc ccgtcgtgta      5820
gataactacg atacgggagg gcttaccatc tggccccagt gctgcaatga taccgcgaga      5880
cccacgctca ccggctccag atttatcagc aataaaccag ccagccggaa gggccgagcg      5940
cagaagtggt cctgcaactt tatccgcctc catccagtct attaattgtt gccgggaagc      6000
tagagtaagt agttcgccag ttaatagttt gcgcaacgtt gttgccattg ctgcaggcat      6060
cgtggtgtca cgctcgtcgt ttggtatggc ttcattcagc tccggttccc aacgatcaag      6120
gcgagttaca tgatccccca tgttgtgcaa aaaagcggtt agctccttcg gtcctccgat      6180
cgttgtcaga agtaagttgg ccgcagtgtt atcactcatg gttatggcag cactgcataa      6240
ttctcttact gtcatgccat ccgtaagatg cttttctgtg actggtgagt actcaaccaa      6300
gtcattctga gaatagtgta tgcggcgacc gagttgctct tgcccggcgt caatacggga      6360
taataccgcg ccacatagca gaactttaaa agtgctcatc attggaaaac gttcttcggg      6420
gcgaaaactc tcaaggatct taccgctgtt gagatccagt tcgatgtaac ccactcgtgc      6480
acccaactga tcttcagcat cttttacttt caccagcgtt tctgggtgag caaaaacagg      6540
aaggcaaaat gccgcaaaaa agggaataag ggcgacacgg aaatgttgaa tactcatact      6600 cttcctttt caatattatt gaagcattta tcagggttat tgtctcatga gcggatacat      6660
atttgaatgt atttagaaaa ataaacaaat aggggttccg cgcacatttc cccgaaaagt      6720
gccacctgac gtctaagaaa ccattattat catgacatta acctataaaa ataggcgtat      6780
cacgaggccc tttcgtcttc aagaa                                            6805
```

<210> SEQ ID NO 30
<211> LENGTH: 5983
<212> TYPE: DNA
<213> ORGANISM: Artificial Sequence
<220> FEATURE:
<223> OTHER INFORMATION: Description of Artificial Sequence:plasmid

<400> SEQUENCE: 30

```
tgcgccgcta cagggcgcgt ccattcgcca ttcaggctgc gcaactgttg ggaagggcga       60
tcggtgcggg cctcttcgct attacgccag ctggcgaaag ggggatgtgc tgcaaggcga      120
ttaagttggg taacgccagg gttttcccag tcacgacgtt gtaaaacgac ggccagtgaa      180
ttgtaatacg actcactata gggcgaattg ggcccgacgt cgcatgctcc cggccgccat      240
ggccgcggga tatcactagt gcggccgcct gcaggtcgac catatgggag agcccggatc      300
caattatggc agatcaatga gcttcacaga cacaatatca gggacatttg ttagttcttt      360
cacaatttta tcttccagat gtctgtcaaa ggaaagcatc atgatggctt ctccgccttt      420
ttccttacgg ccaacctgca tagttgcaat gttaatatca ttatctccga gaatacgtcc      480
tactcggccg atgacacctg ttgtatcttg atgctggata tacaccaagt gaccagtcgg      540
ataaaaatca atattaaatc cattgatctc gacaattcgt tctccgaaat gaggaatata      600
cgtagccgtt acagtaaagg tgctgcggtc tcctgtcact tttacgctga tgcagttatc      660
gtatccagat tcagaagagg aaatttttc actgaagcta atgccgcgtt cttttgcgac      720
```

```
accccccggca ttgacctcat taacagtaga gtctacgcgc ggttttaaaa agcctgacag    780
aagggctttt gtaatgaacg atgtttcaag tttagcaatt gtgccttcat attgaatggc    840
aacatcctgt actggttctt tcatgcactg tgatacaagg ctgccaattt ttcctgcaat    900
ttgatggtaa ggcttaattt tagcaaattc atcttttgtc atggcaggca ggttgatagc    960
tgacatgaca ggcaggcctt ttgcgaactg cagaacttct tctgacactt gggcggcgac   1020
attgagctgt gcttctttcg ttgatgctcc caagtgagga gtggcaatga ctaatggatg   1080
atcaacaagt ttgttgtcaa ctggcggttc gacttcgaaa acgtcaagcg ctgctcccgc   1140
aacatgcccg ttttccaaag cttttttagac atctaaatct aggtactaaa acaattcatc   1200
cagtaaaata taatatttta ttttctccca atcaggcttg atccccagta agtcaaaaaa   1260
tagctcgaca tactgttctt ccccgatatc ctccctgatc gaccggacgc agaaggcaat   1320
gtcataccac ttgtccgccc tgccgcttct cccaagatca ataaagccac ttactttgcc   1380
atctttcaca aagatgttgc tgtctcccag gtcgccgtgg gaaaagacaa gttcctcttc   1440
gggcttttcc gtctttaaaa aatcatacag ctcgcgcgga tctttaaatg gagtgtcttc   1500
ttcccagttt tcgcaatcca catcggccag atcgttattc agtaagtaat ccaattcggc   1560
taagcggctg tctaagctat tcgtataggg acaatccgat atgtcgatgg agtgaaagag   1620
cctgatgcac tccgcataca gctcgataat cttttcaggg cttttgttcat cttcatactc   1680 ttccgagcaa aggacgccat cggcctcact catgagcaga ttgctccagc catcatgccg   1740
ttcaaagtgc aggacctttg aacaggcag cttttccttcc agccatagca tcatgtcctt   1800
ttcccgttcc acatcatagg tggtcccttt ataccggctg tccgtcattt ttaaatatag   1860
gttttcattt tctcccacca gcttatatac cttagcagga gacattcctt ccgtatcttt   1920
tacgcagcgg tattttttcga tcagtttttt caattccggt gatattctca ttttagccat   1980
ttattatttc cttcctcttt tctacagtat ttaaagatac cccaagaagc taattataac   2040
aagacgaact ccaattcact gttccttgca ttctaaaacc ttaaatacca gaaaacagct   2100
ttttcaaagt tgttttgaaa gttggcgtat aacatagtat cgacggagcc gattttgaaa   2160
ccacaattat gatagaattt acaagctata aggttattgt cctgggtttc aagcattagt   2220
ccatgcaagt ttttatgctt tgcccattct atagatatat tgataagcgc gctgcctatg   2280
ccttgccccc tgaaatcctt acatacggcg atatcttcta tataaaagat atattatctt   2340
atcagtattg tcaatatatt caaggcaatc tgcctcctca tcctcttcat cctcttcgtc   2400
ttggtagctt tttaaatatg gcgcttcata gagtaattct gtaaaggtcc aattctcgtt   2460
ttcatacctc ggtataatct tacctatcac ctcaaatggt tcgctgggtt tatcgcctga   2520
tgcggtattt tctccttacg catctgtgcg gtatttcacg tcgacgcggc cgccatggcc   2580
gcgggatccc ggtaccgaaa catcgttaga tttcctccta aattgacaaa ctaaatatct   2640
gataatttaa catattctca aaagagtgtc aacgtgtatt gacgcagtaa aggataaaag   2700
taaagcctaa taaatcaatg atctgacagc ttgcaggtaa tatatttaat ttgaagcaat   2760
tctctataca gccaaccagt tatcgtttat aatgtaatta aatttcatat gatcaatctt   2820
cggggcaggg tgaaattccc taccggcggt gatgagccaa tggctctaag cccgcgagct   2880
gtctttacag caggattcgg tgagattccg gagccgacag tacagtctgg atgggagaag   2940
atggaggttc ataagcgttt tgaaattgaa ttttttcaaac gtttctttgc ctagcctaat   3000
tttcgaaacc ccgcttttat atatgaagcg gttttttttat tggctggaaa agaaccttcc   3060
cgttttcgag taagatgtga tcgaaaagga gagaatgaag tgaaagtaaa aaaattagtt   3120
```

```
gtggtcagca tgctgagcag cattgcattt gttttgatgc tgttaaattt cccgtttccg    3180
ggtcttccgg attatttaaa aatcgatttt agcgacgttc ccgcaattat tgccattctg    3240
atttacggac ctttggcggg atcactagag ggctcccaac gcgttggatg catagcttga    3300
gtattctata gtgtcaccta aatagcttgg cgtaatcatg gtcatagctg tttcctgtgt    3360
gaaattgtta tccgctcaca attccacaca acatacgagc cggaagcata aagtgtaaag    3420
cctggggtgc ctaatgagtg agctaactca cattaattgc gttgcgctca ctgcccgctt    3480
tccagtcggg aaacctgtcg tgccagctgc attaatgaat cggccaacgc gcggggagag    3540
gcggtttgcg tattgggcgc tcttccgctt cctcgctcac tgactcgctg cgctcggtcg    3600
ttcggctgcg gcgagcggta tcagctcact caaaggcggt aatacggtta tccacagaat    3660
caggggataa cgcaggaaag aacatgtgag caaaaggcca gcaaaaggcc aggaaccgta    3720
aaaaggccgc gttgctggcg tttttcgata ggctccgccc ccctgacgag catcacaaaa    3780
atcgacgctc aagtcagagg tggcgaaacc cgacaggact ataaagatac caggcgtttc    3840
cccctggaag ctccctcgtg cgctctcctg ttccgaccct gccgcttacc ggatacctgt    3900
ccgcctttct cccttcggga agcgtggcgc tttctcatag ctcacgctgt aggtatctca    3960
gttcggtgta ggtcgttcgc tccaagctgg gctgtgtgca cgaaccccc gttcagcccg    4020 accgctgcgc cttatccggt aactatcgtc ttgagtccaa cccggtaaga cacgacttat    4080
cgccactggc agcagccact ggtaacagga ttagcagagc gaggtatgta ggcggtgcta    4140
cagagttctt gaagtggtgg cctaactacg gctacactag aaggacagta tttggtatct    4200
gcgctctgct gaagccagtt accttcggaa aaagagttgg tagctcttga tccggcaaac    4260
aaaccaccgc tggtagcggt ggtttttttg tttgcaagca gcagattacg cgcagaaaaa    4320
aaggatctca agaagatcct ttgatctttt ctacggggtc tgacgctcag tggaacgaaa    4380
actcacgtta agggattttg gtcatgagat tatcaaaaag gatcttcacc tagatccttt    4440
taaattaaaa atgaagtttt aaatcaatct aaagtatata tgagtaaact tggtctgaca    4500
gttaccaatg cttaatcagt gaggcaccta tctcagcgat ctgtctattt cgttcatcca    4560
tagttgcctg actccccgtc gtgtagataa ctacgatacg ggagggctta ccatctggcc    4620
ccagtgctgc aatgataccg cgagacccac gctcaccggc tccagattta tcagcaataa    4680
accagccagc cggaagggcc gagcgcagaa gtggtcctgc aactttatcc gcctccatcc    4740
agtctattaa ttgttgccgg gaagctagag taagtagttc gccagttaat agtttgcgca    4800
acgttgttgg cattgctaca ggcatcgtgg tgtcacgctc gtcgtttggt atggcttcat    4860
tcagctccgg ttcccaacga tcaaggcgag ttacatgatc ccccatgttg tgcaaaaaag    4920
cggttagctc cttcggtcct ccgatcgttg tcagaagtaa gttggccgca gtgttatcac    4980
tcatggttat ggcagcactg cataattctc ttactgtcat gccatccgta agatgctttt    5040
ctgtgactgg tgagtactca accaagtcat tctgagaata ccgcgccgg cgaccgagtt    5100 gctcttgccc ggcgtcaata cgggataata gtgtatgaca tagcagaact ttaaaagtgc    5160
tcatcattgg aaaacgttct cggggcgaa aactctcaag gatcttaccg ctgttgagat    5220
ccagttcgat gtaacccact cgtgcaccca actgatcttc agcatctttt actttcacca    5280
gcgtttctgg gtgagcaaaa acaggaaggc aaaatgccgc aaaaaaggga ataagggcga    5340
cacggaaatg ttgaatactc atactcttcc ttttcaata ttattgaagc atttatcagg    5400
gttattgtct catgagcgga tacatatttg aatgtatttta gaaaaataaa caatagggg    5460 ttccgcgcac atttccccga aaagtgccac ctgtatgcgg tgtgaaatac cgcacagatg    5520
```

```
cgtaaggaga aaataccgca tcaggcgaaa ttgtaaacgt taatattttg ttaaaattcg      5580
cgttaaatat ttgttaaatc agctcatttt ttaaccaata ggccgaaatc ggcaaaatcc      5640
cttataaatc aaaagaatag accgagatag ggttgagtgt tgttccagtt tggaacaaga      5700
gtccactatt aaagaacgtg gactccaacg tcaaagggcg aaaaaccgtc tatcagggcg      5760
atggcccact acgtgaacca tcacccaaat caagtttttt gcggtcgagg tgccgtaaag      5820
ctctaaatcg aaccctaaa  gggagccccc gatttagagc ttgacgggga aagccggcga      5880
acgtggcgag aaaggaaggg aagaaagcga aaggagcggg cgctagggcg ctggcaagtg      5940
tagcggtcac gctgcgcgta accaccacac ccgccgcgct taa                        5983

<210> SEQ ID NO 31
<211> LENGTH: 7330
<212> TYPE: DNA
<213> ORGANISM: Artificial Sequence
<220> FEATURE:
<223> OTHER INFORMATION: Description of Artificial Sequence:plasmid

<400> SEQUENCE: 31
ttgcggccgc ttcgaaagct gtaatataaa aaccttcttc aactaacggg gcaggttagt        60
gacattagaa aaccgactgt aaaaagtaca gtcggcatta tctcatatta taaaagccag       120
tcattaggcc tatctgacaa ttcctgaata gagttcataa acaatcctgc atgataacca       180
tcacaaacag aatgatgtac ctgtaaagat agcggtaaat atattgaatt acctttatta       240
atgaattttc ctgctgtaat aatgggtaga aggtaattac tattattatt gatatttaag       300
ttaaacccag taaatgaagt ccatggaata atagaaagag aaaaagcatt ttcaggtata       360
ggtgttttgg gaaacaattt ccccgaacca ttatatttct ctacatcaga aaggtataaa       420
tcataaaact ctttgaagtc attctttaca ggagtccaaa taccagagaa tgttttagat       480
acaccatcaa aaattgtata aagtggctct aacttatccc aataacctaa ctctccgtcg       540
ctattgtaac cagttctaaa agctgtattt gagtttatca cccttgtcac taagaaaata       600
aatgcagggt aaaatttata tccttcttgt tttatgtttc ggtataaaac actaatatca       660
atttctgtgg ttatactaaa agtcgtttgt tggttcaaat aatgattaaa tatctctttt       720
ctcttccaat tgtctaaatc aatttttatta aagttcattt gatatgcctc ctaaattttt      780
atctaaagtg aatttaggag gcttacttgt ctgctttctt cattagaatc aatccttttt       840
taaaagtcaa tattactgta acataaatat atattttaaa aatatcccac tttatccaat       900
tttcgtttgt tgaactaatg ggtgctttag ttgaagaata aagaccacat taaaaaatgt       960
ggtcttttgt gtttttttaa aggatttgag cgtagcgaaa aatcctttc  tttcttatct      1020 tgataataag ggtaactatt gaattcggta ccaagagttt gtagaaacgc aaaaaggcca      1080
tccgtcagga tggccttctg cttaatttga tgcctggcag tttatggcgg gcgtcctgcc      1140
cgccaccctc cgggccgttg cttcgcaacg ttcaaatccg ctcccggcgg atttgtccta      1200
ctcaggagag cgttcaccga caaacaacag ataaaacgaa aggcccagtc tttcgactga      1260
gcctttcgtt ttatttgatg cctggcagtt ccctactctc gcatgggag  accccacact      1320 accatcggcg ctacggcgtt tcacttctga gttcggcatg gggtcaggtg gaccaccgc       1380 gctactgccg ccaggcaaat tctgttttat cagaccgctt ctgcgttctg atttaatctg      1440
tatcaggctg aaaatcttct ctcatccgcc aaaacaggat ccaattatgg cagatcaatg      1500
agcttcacag acacaatatc agggacattt gttagttctt tcacaatttt atcttccaga      1560
tgtctgtcaa aggaaagcat catgatggct tctccgcctt tttccttacg gccaacctgc      1620
```

```
atagttgcaa tgttaatatc attatctccg agaatacgtc ctactcggcc gatgacacct    1680
gttgtatctt gatgctggat atacaccaag tgaccagtcg gataaaaatc aatattaaat    1740
ccattgatct cgacaattcg ttctccgaaa tgaggaatat acgtagccgt tacagtaaag    1800
gtgctgcggt ctcctgtcac ttttacgctg atgcagttat cgtatccaga ttcagaagag    1860 gaaattttt cactgaagct aatgccgcgt tcttttgcga caccccggc attgacctca     1920 ttaacagtag agtctacgcg cggttttaaa aagcctgaca gaagggcttt tgtaatgaac    1980
gatgtttcaa gtttagcaat tgtgccttca tattgaatgg caacatcctg tactggttct    2040
ttcatgcact gtgatacaag gctgccaatt tttcctgcaa tttgatggta aggcttaatt    2100
ttagcaaatt catcttttgt catggcaggc aggttgatag ctgacatgac aggcaggcct    2160
tttgcgaact gcagaacttc ttctgacact tgggcggcga cattgagctg tgcttctttc    2220
gttgatgctc ccaagtgagg agtggcaatg actaatggat gatcaacaag tttgttgtca    2280
actggcggtt cgacttcgaa aacgtcaagc gctgctcccg caacatgccc gttttccaaa    2340
gcttcgagaa gtgctgcttc atcgataatt ccgcctcgcg cacagttaat taagcgaacg    2400
ccttttttcg ttttttgcaat cgtttcttta ttcaataagc cttttgtttc ttttgttaaa    2460
ggcgtgtgaa cggtaatgat atccgcactt tcaagcactt cttcaaatgt acggctgttt    2520
acgccgattt ttttcgctct ttcttccgtt aagaaaggat caaaaacgtg cacagtcata    2580
ccgaacgctc ctcgacgctg tgcaatttca cttccgattc ggcctaatcc tacaatacca    2640 agcgttttc cataaagctc tgaaccgaca taagctgtgc ggttccactc tctggatttc     2700
actgagatat tagcctgcgg aatgtgtctc attaaagaag agatcattgc aaatgtatgc    2760
tcagctgtcg aaatggtgtt gccgttcgga gcattgatca cgattacccc gtgtttcgta    2820
gcctcatcaa tatcgatatt atcgacaccg acaccggctc ttccgacaat ttttaaagaa    2880
gtcattttgt tgaaaaggtc ttctgttact tttgtcgcgc ttcgcaccaa agagcatca     2940 aaagtatgta attcatcttc tgcatctgct acgttttttt gaacgatttc aataaagtct    3000
gattcaataa gtggctgtaa accgtcgttc tcattttgt ctgagaccaa tactcgaaac     3060
atgttttctc ctcctctaga gcgtcctgct gttgttaaga ttattatacc acaccttgta    3120
gataaagtca acaactttt gcaaaatttt tcaggaattt tagcagaggt tgttctggat     3180
gtagaacaaa acatctttcc gctcttgtgc tgttaggata tctttcttgg aagctaggta    3240
ggcctcgagt tatggcagtt ggttaaaagg aaacaaaaag accgttttca cacaaaacgg    3300 tcttttttcga tttcttttta cagtcacagc cacttttgca aaaaccggac agcttcatgc    3360
cttataactg ctgtttcggt cgacgaaaca tcgttagatt tcctcctaaa ttgacaaact    3420
aaatatctga taatttaaca tattctcaaa agagtgtcaa cgtgtattga cgcagtaaag    3480 gataaagta agcctaata aatcaatgat ctgacagctt gcaggtaata tatttaattt      3540
gaagcaattc tctatacagc caaccagtta tcgtttataa tgtaattaaa tttcatatga    3600
tcaatcttcg gggcagggtg aaattcccta ccggcggtga tgagccaatg gctctaagcc    3660
cgcgagctgt ctttacagca ggattcggtg agattccgga gccgacagta cagtctggat    3720
gggagaagat ggaggttcat aagcgttttg aaattgaatt tttcaaacgt ttctttgcct    3780
agcctaattt tcgaaacccc gcttttatat atgaagcggt ttttttattg gctggaaaag    3840
aacctttccg ttttcgagta agatgtgatc gaaaaggaga gaatgaagtg aaagtaaaaa    3900
aattagttgg ggtcagcatg caagcttcgc gaagcggccg ccgacgcgag gctggatggc    3960
cttccccatt atgattcttc tcgcttccgg cggcatcggg atgcccgcgt tgcaggccat    4020
```

```
gctgtccagg caggtagatg acgaccatca gggacagctt caaggatcgc tcgcggctct    4080
taccagccta acttcgatca ctggaccgct gatcgtcacg gcgatttatg ccgcctcggc    4140
gagcacatgg aacgggttgg catggattgt aggcgccgcc ctataccttg tctgcctccc    4200
cgcgttgcgt cgcggtgcat ggagccgggc cacctcgacc tgaatggaag ccggcggcac    4260
ctcgctaacg gattcaccac tccaagaatt ggagccaatc aattcttgcg agaactgtg    4320 aatgcgcaaa ccaacccttg gcagaacata tccatcgcgt ccgccatctc cagcagccgc    4380
acgcggcgca tctcgggcag cgttgggtcc tggccacggg tgcgcatgat cgtgctcctg    4440
tcgttgagga cccggctagg ctggcggggt tgccttactg gttagcagaa tgaatcaccg    4500
atacgcgagc gaacgtgaag cgactgctgc tgcaaaacgt ctgcgacctg agcaacaaca    4560
tgaatggtct tcggtttccg tgtttcgtaa agtctggaaa cgcggaagtc agcgccctgc    4620
accattatgt tccggatctg catcgcagga tgctgctggc taccctgtgg aacacctaca    4680
tctgtattaa cgaagcgctg gcattgaccc tgagtgattt ttctctggtc ccgccgcatc    4740
cataccgcca gttgtttacc ctcacaacgt tccagtaacc gggcatgttc atcatcagta    4800
acccgtatcg tgagcatcct ctctcgtttc atcggtatca ttaccccat gaacagaaat    4860 tcccccttac acggaggcat caagtgacca acaggaaaa accgcccctt aacatggccc    4920
gctttatcag aagccagaca ttaacgcttc tggagaaact caacgagctg gacgcggatg    4980
aacaggcaga catctgtgaa tcgcttcacg accacgctga tgagctttac cgcagctgcc    5040
tcgcgcgttt cggtgatgac ggtgaaaacc tctgacacat gcagctcccg gagacggtca    5100
cagcttgtct gtaagcggat gccggagca gacaagcccg tcagggcgcg tcagcgggtg    5160
ttggcgggtg tcggggcgca gccatgaccc agtcacgtag cgatagcgga gtgtatactg    5220
gcttaactat gcggcatcag agcagattgt actgagagtg caccatatgc ggtgtgaaat    5280
accgcacaga tgcgtaagga gaaaataccg catcaggcgc tcttccgctt cctcgctcac    5340
tgactcgctg cgctcggtcg ttcggctgcg gcgagcggta tcagctcact caaaggcggt    5400
aatacggtta tccacagaat caggggataa cgcaggaaag aacatgtgag caaaaggcca    5460
gcaaaaggcc aggaaccgta aaaaggccgc gttgctggcg ttttttccata ggctccgccc    5520 ccctgacgag catcacaaaa atcgacgctc aagtcagagg tggcgaaacc cgacaggact    5580
ataaagatac caggcgtttc ccctggaag ctccctcgtg cgctctcctg ttccgaccct    5640
gccgcttacc ggatacctgt ccgcctttct cccttcggga agcgtggcgc tttctcatag    5700
ctcacgctgt aggtatctca gttcggtgta ggtcgttcgc tccaagctgg gctgtgtgca    5760 cgaaccccc gttcagcccg accgctgcgc cttatccggt aactatcgtc ttgagtccaa    5820
cccggtaaga cacgacttat cgccactggc agcagccact ggtaacagga ttagcagagc    5880
gaggtatgta ggcggtgcta cagagttctt gaagtggtgg cctaactacg gctacactag    5940
aaggacagta tttggtatct gcgctctgct gaagccagtt accttcggaa aaagagttgg    6000
tagctcttga tccggcaaac aaaccaccgc tggtagcggt ggtttttttg tttgcaagca    6060
gcagattacg cgcagaaaaa aaggatctca agaagatcct ttgatctttt ctacggggtc    6120
tgacgctcag tggaacgaaa actcacgtta agggattttg gtcatgagat tatcaaaaag    6180
gatcttcacc tagatccttt taaattaaaa atgaagtttt aaatcaatct aaagtatata    6240
tgagtaaact tggtctgaca gttaccaatg cttaatcagt gaggcaccta tctcagcgat    6300
ctgtctattt cgttcatcca tagttgcctg actccccgtc gtgtagataa ctacgatacg    6360
ggagggctta ccatctggcc ccagtgctgc aatgataccg cgagacccac gctcaccggc    6420
```

```
tccagattta tcagcaataa accagccagc cggaagggcc gagcgcagaa gtggtcctgc    6480
aactttatcc gcctccatcc agtctattaa ttgttgccgg gaagctagag taagtagttc    6540
gccagttaat agtttgcgca acgttgttgc cattgctgca ggcatcgtgg tgtcacgctc    6600
gtcgtttggt atggcttcat tcagctccgg ttcccaacga tcaaggcgag ttacatgatc    6660
ccccatgttg tgcaaaaaag cggttagctc cttcggtcct ccgatcgttg tcagaagtaa    6720
gttggccgca gtgttatcac tcatggttat ggcagcactg cataattctc ttactgtcat    6780
gccatccgta agatgctttt ctgtgactgg tgagtactca accaagtcat tctgagaata    6840
gtgtatgcgg cgaccgagtt gctcttgccc ggcgtcaata cgggataata ccgcgccaca    6900
tagcagaact ttaaaagtgc tcatcattgg aaaacgttct tcggggcgaa aactctcaag    6960
gatcttaccg ctgttgagat ccagttcgat gtaacccact cgtgcaccca actgatcttc    7020
agcatctttt actttcacca gcgtttctgg gtgagcaaaa acaggaaggc aaaatgccgc    7080
aaaaaaggga ataagggcga cacggaaatg ttgaatactc atactcttcc tttttcaata    7140
ttattgaagc atttatcagg gttattgtct catgagcgga tacatatttg aatgtattta    7200
gaaaaataaa caaatagggg ttccgcgcac atttccccga aaagtgccac ctgacgtcta    7260
agaaaccatt attatcatga cattaaccta taaaaatagg cgtatcacga ggccctttcg    7320
tcttcaagaa                                                           7330
```

MICROORGANISMS AND PROCESSES FOR ENHANCED PRODUCTION OF PANTOTHENATE

RELATED APPLICATIONS

This application claims priority to U.S. Provisional Patent Application No. 60/393,826, filed on Jul. 3, 2002, entitled "Microorganisms and Processes for Enhanced Production of Pantothenate". This application is related to International Patent Application No. PCT/US02/00925, entitled "Microorganisms and Processes for Enhanced Production of Pantothenate", filed Jan. 18, 2002 (pending), which, in turn, claims the benefit of prior-filed provisional Patent Application Ser. No. 60/347,638, entitled "Microorganisms and Processes for Enhanced Production of Pantothenate", filed Jan. 11, 2002, to prior-filed provisional Patent Application Ser. No. 60/263,053, filed Jan. 19, 2001 (expired), and to prior-filed provisional Patent Application Ser. No. 60/262,995, filed Jan. 19, 2001 (expired). The present invention is also related to U.S. patent application Ser. No. 09/667,569, filed Sep. 21, 2000 (pending), which is a continuation-in-part of U.S. patent application Ser. No. 09/400,494, filed Sep. 21, 1999 (abandoned). U.S. patent application Ser. No. 09/667,569 also claims the benefit of prior-filed provisional Patent Application Ser. No. 60/210,072, filed Jun. 7, 2000 (expired), provisional Patent Application Ser. No. 60/221,836, filed Jul. 28, 2000 (expired), and provisional Patent Application Ser. No. 60/227,860, filed Aug. 24, 2000 (expired). The entire content of each of the above-referenced applications is incorporated herein by this reference.

BACKGROUND OF THE INVENTION

Pantothenate also known as pantothenic acid or vitamin B5, is a member of the B complex of vitamins and is a nutritional requirement for mammals, including livestock and humans (e.g., from food sources, as a water soluble vitamin supplement or as a feed additive). In cells, pantothenate is used primarily for the biosynthesis of coenzyme A (CoA) and acyl carrier protein (ACP). These coenzymes function in the metabolism of acyl moieties which form thioesters with the sulfhydryl group of the 4'-phosphopantetheine portion of these molecules. These coenzymes are essential in all cells, participating in over 100 different intermediary reactions in cellular metabolism.

The conventional means of synthesizing pantothenate (in particular, the bioactive D isomer) is via chemical synthesis from bulk chemicals, a process which is hampered by excessive substrate cost as well as the requirement for optical resolution of racemic intermediates. Accordingly, researchers have recently looked to bacterial or microbial systems that produce enzymes useful in pantothenate biosynthesis processes (as bacteria are themselves capable of synthesizing pantothenate). In particular, bioconversion processes have been evaluated as a means of favoring production of the preferred isomer of pantothenic acid. Moreover, methods of direct microbial synthesis have recently been examined as a means of facilitating D-pantothenate production.

There is still, however, significant need for improved pantothenate production processes, in particular, for microbial processes optimized to produce higher yields of desired product.

SUMMARY OF THE INVENTION

The present invention relates to improved processes (e.g., microbial syntheses) for the production of pantothenate. Pantothenate production processes have been described in related applications which feature, for example, microbes engineered to overexpress key enzymes of the pantothenate biosynthetic pathway and the isoleucine-valine biosynthetic pathway (see e.g., FIG. 1). Strains have been engineered that are capable of producing >50 g/l of pantothenate in standard fermentation processes (see e.g., International Public. No. WO 01/21772 and U.S. Patent Application Ser. No. 60/262,995). In particular, increasing the expression of the panB, panC, panD and panE1 genes and increasing the expression of the ilvBNC and ilvD genes results in strains that convert glucose (pyruvate) to commercially attractive quantities of pantothenate.

In order to enhance production levels of for example, pantothenate, various improvements on the above-described methods have now been developed. For example, U.S. patent application Ser. No. 09/667,569 describes production strains having modified (e.g., deleted or decreased-activity) pantothenate kinase enzymes. In such strains the pantothenate levels are effectively increased by decreasing utilization of pantothenate for coenzymeA ("CoA") synthesis. U.S. Patent Application Ser. No. 60/262,995 further describes improved pantothenate-production strains that have been engineered to minimize utilization of various pantothenate biosynthetic enzymes and/or isoleucine-valine biosynthetic enzymes and/or their respective substrates from being used to produce an alternative product identified as [R]-3-(2-hydroxy-3-methylbutyrylamino)-propionic acid ("HMPA").

The present invention features methods to further enhance pantothenate production by modulating a biosynthetic pathway that supplies a substrate for the pantothenate biosynthetic pathway, namely the methylenetetrahydrofolate ("MTF") biosynthetic pathway. In particular, it has been discovered that increasing levels of MTF by modification of the MTF biosynthetic pathway results in enhanced levels of the key pantothenate biosynthetic pathway intermediate, ketopantoate. Enhanced ketopantoate levels, in turn, result in significantly enhanced pantothenate production levels in appropriately engineered stains. In essence, the present inventors have identified a limiting step in the production of panto-compounds (e.g., pantothenate) by strains engineered to overexpress, for example, the panB, panC, panD, panE1, ilvBNC and ilvD genes, and describe herein a means for overcoming this limitation by modification of the MTF biosynthetic pathway.

At least three effective means of modifying the MTF biosynthetic pathway are described herein. In one aspect, it has been demonstrated that increasing serine levels in the culture medium of pantothenate-producing microorganisms results in enhanced panto-compound production. It has also been demonstrated that increasing the synthesis or activity of 3-phosphoglycerate dehydrogenase (the serA gene product), or the synthesis or activity of serine hydroxymethyl transferase (the glyA gene product), thereby enhancing serine and methylenetetrahydrofolate biosynthesis in appropriately engineered microorganisms, increases panto-compound production. Increased synthesis of 3-phosphoglycerate dehydrogenase (the sera gene product) is achieved, for example, by overexpressing sera from an appropriately-engineered expression cassette. Increased synthesis of serine hydroxymethyl transferase (the glyA gene product) is achieved, for example, by overexpressing glyA from an appropriately-engineered expression cassette. Alternatively, levels of serine hydroxymethyl transferase (the glyA gene product) are increased by altering the regulation of the glyA gene. For example, mutation or deletion of the gene encoding a negative regulator (i.e., repressor) of glyA expression, the purR gene, effectively increases glyA expression. Additional methods suitable for increasing MTF levels in panto-compound producing microorganisms involve deregulating enzymes responsible for converting glycine to MTF (e.g., glycine cleavage enzymes).

Accordingly, in one aspect the invention features processes for the enhanced production of pantoate and pantothenate that involve culturing microorganisms having modified pantothenate biosynthetic enzyme activities and having modified methylenetetrahydrofolate (MTF) biosynthetic enzyme activities under conditions such that pantothenate production is enhanced. In another aspect the invention features processes for the enhanced production of pantoate and pantothenate that involve culturing microorganisms having modified pantothenate biosynthetic enzyme activities, having modified isoleucine-valine (ilv) biosynthetic enzymes, and having modified methylenetetrahydrofolate (MTF) biosynthetic enzyme activities under conditions such that pantothenate production is enhanced. In particular, the invention features methods for enhancing production of desired products (e.g., pantoate and/or pantothenate) by increasing the levels of a key intermediate, ketopantoate, by enzymes that contribute to its synthesis. Preferred methods result in production of pantothenate at levels greater than 50, 60, 70 or more g/L after 36 hours of culturing the microorganisms, or such that at least 60, 70, 80, 90, 100, 110, 120 or more g/L pantothenate is produced after 36 hours of culturing the microorganisms. Recombinant microorganisms and conditions for culturing same are also are featured. Also featured are compositions produced by such microorganisms.

Other features and advantages of the invention will be apparent from the following detailed description and claims.

BRIEF DESCRIPTION OF THE DRAWINGS

FIG. 3 is a schematic representation of the construction of the plasmid pAN665.

DETAILED DESCRIPTION OF THE INVENTION

The present invention is directed to improved methods for producing panto-compounds (e.g., ketopantoate, pantoate and/or pantothenate) and strains engineered for use in said improved methods. Strains capable of producing >50 g/l of pantothenate can be constructed as taught in International Patent Application Serial No. WO 01/21772 and in U.S. Patent Application Ser. No. 60/262,995. By increasing the expression of the panB, panC, panD and panE1 genes and by increasing the expression of the ilvBNC and ilvD genes, one can design strains (e.g., *Bacillus* strains) that convert glucose (pyruvate) to commercially attractive quantities of pantothenate.

However, it has now been discovered that in strains engineered to express high levels of the panB gene product, ketopantoate hydroxymethyltransferase (e.g., PAS824, described in U.S. patent application Ser. No. 09/667,569 and PA668-24, described in U.S. Patent Application Ser. No. 60/262,995), a limiting step for further increases in the production of pantothenate is still the conversion of α-ketoisovalerate (α-KIV) to ketopantoate. Methods to increase the synthesis of α-KIV were described previously in International Patent Application Serial No. WO 01/21772 and U.S. Patent Application Ser. No. 60/262,995. Here we disclose that even further increases in pantothenate production can be achieved by engineering panto-compound producing microorganisms such that the level of MTF, or the rate of MTF synthesis is enhanced or increased.

Accordingly, the present invention features methods for improving panto-compound production that involve modulating the methylenetetrahydrofolate ("MTF") biosynthetic pathway. In particular, increasing of levels in panto-compound producing microbe is an effective means of enhancing ketopantoate production, and in turn results in enhanced pantoate and/or pantothenate production in appropriately-engineered recombinant microorganisms.

Figure 1:
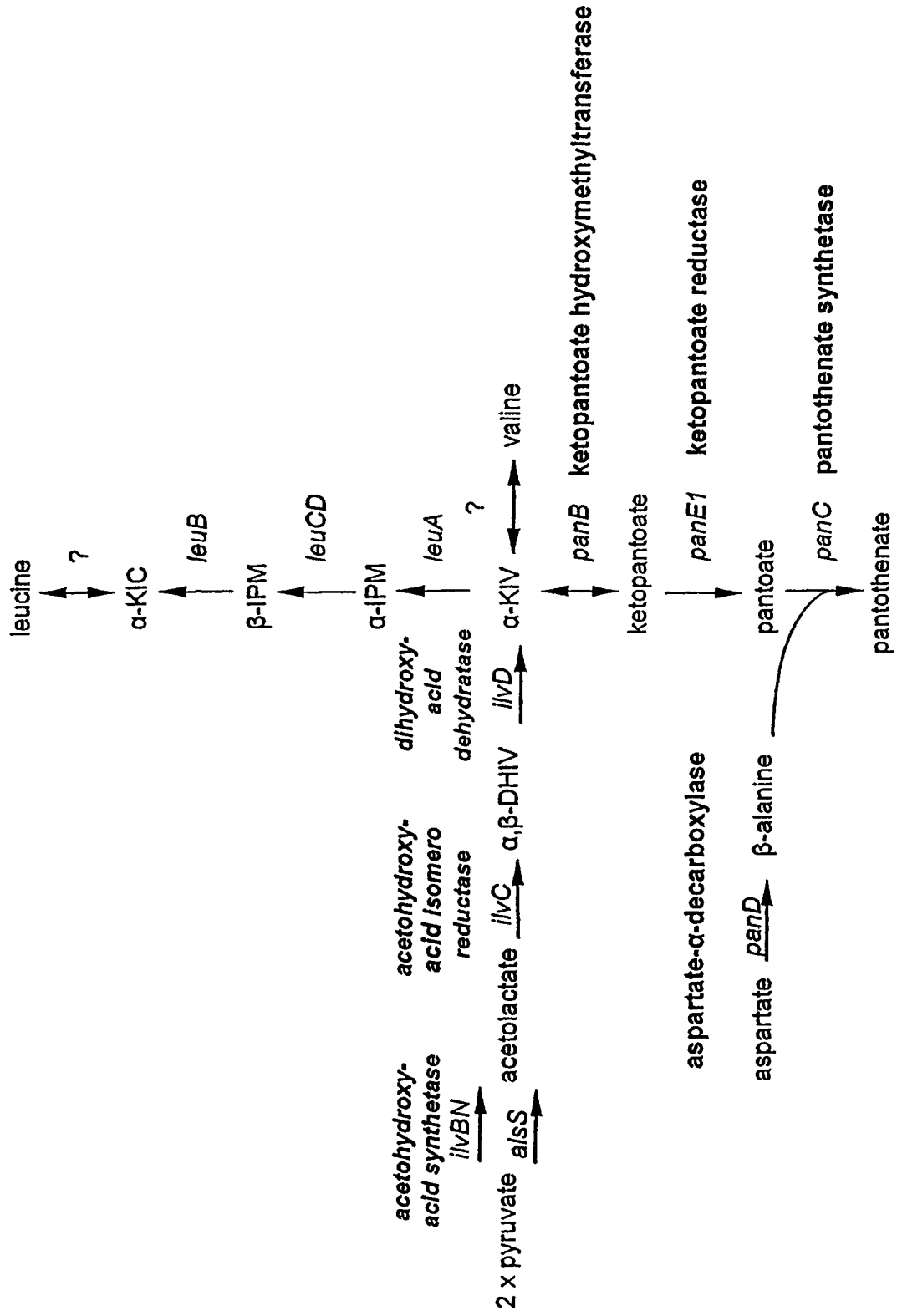
FIG. 1 is a schematic representation of the pantothenate and isoleucine-valine (ilv) biosynthetic pathways. Pantothenate biosynthetic enzymes are depicted in bold and their corresponding genes indicated in italics. Isoleucine-valine (ilv) biosynthetic enzymes are depicted in bold italics and their corresponding genes indicated in italics.

Ketopantoate hydroxymethlylenetransferase catalyzes the production of ketopantoate from α-ketoisovalerate ("α-KIV") and MTF (see e.g., FIG. 1). In particular, the enzyme catalyzes the transfer of a hydroxymethyl group from MTF to α-KIV to yield ketopantoate. Both α-KIV and MTF are substrates for this reaction, and their syntheses can be increased in order to improve production of ketopantoate. The pathway for MTF biosynthesis in *E. coli* (and also in *Bacillus subtilis*) is outlined in FIG. 2. MTF is synthesized from tetrahydrofolate and serine in a reaction catalyzed by the glyA gene that encodes serine hydroxymethyl transferase. For improved MTF synthesis the cells need increased quantities of both substrates and the product of the glyA gene.

In one embodiment the invention features processes for the enhanced production of pantothenate that involve culturing a microorganism having (i) a deregulated pantothenate biosynthetic pathway (e.g., having one, two, three or four pantothenate biosynthetic enzymes deregulated) and (ii) a deregulated methylenetethrhydrofolate (MTF) biosynthetic pathway (e.g., having at least one or two MTF biosynthetic enzymes deregulated), under conditions such that pantothenate production is enhanced. Exemplary pantothenate biosynthetic enzymes include ketopantoate hydroxymethyltransferase, ketopantoate reductase, pantothenate synthetase and aspartate-α-decarboxylase. Exemplary MTF biosynthetic enzymes include the serA gene product and the glyA gene product.

In another embodiment, the invention features processes for the enhanced production of pantothenate that involve culturing a microorganism having (i) a deregulated pantothenate biosynthetic pathway (e.g., having one, two, three or four pantothenate biosynthetic enzymes deregulated), (ii) a deregulated isoleucine-valine (ilv) biosynthetic pathway (e.g., having one, two or three ilv biosynthetic enzymes deregulated), and (iii) a deregulated MTF biosynthetic pathway (e.g., having at least one or two MTF biosynthetic enzymes deregulated), under conditions such that pantothenate production is enhanced. Exemplary ilv biosynthetic enzymes include acetohydroxyacid acid synthetase, acetohydroxyacid isomeroreductase, and dihydroxyacid dehydratase.

In another embodiment, the invention features processes for the production of pantothenate that involve culturing a microorganism having a deregulated pantothenate biosynthetic pathway, a deregulated ilv biosynthetic pathway, and a deregulated MTF biosynthetic pathway, such that at least 50 g/L pantothenate is produced after 36 hours of culturing the microorganism, preferably such that at least 60 g/L pantothenate is produced after 36 hours of culturing the microorganism, more preferably such that at least 70 g/L pantothenate is produced after 36 hours of culturing the microorganism, and most preferably such that at least 80 g/L pantothenate, at least 90 g/L pantothenate at least 100 g/L pantothenate, at least 110 g/L pantothenate, or at least 120 g/L pantothenate (or more) is produced after 36 hours of culturing the microorganism.

In another embodiment, the invention features processes for the production of pantothenate that involve culturing a microorganism having a deregulated pantothenate biosynthetic pathway, a deregulated ilv biosynthetic pathway, and a deregulated MTF biosynthetic pathway, deregulated such that at least 70 g/L pantothenate is produced after 48 hours of culturing the microorganism, preferably such that at least 80 g/L pantothenate is produced after 48 hours of culturing the microorganism, and more preferably such that at least 90 g/L pantothenate is produced after 48 hours of culturing the microorganism.

In one exemplary embodiment, deregulation of the MTF biosynthetic pathway is achieved by deregulating the serA gene product in a panto-compound producing strain, for example, by expressing the serA gene constitutively or by introducing a feedback resistant allele of serA. In another exemplary embodiment, deregulation of the MTF biosynthetic pathway is achieved by deregulating the glyA gene product in a panto-compound producing strain, for example, by overexpressing the glyA gene or modulating repression of the glyA gene by mutating or disrupting the purR gene product. In other exemplary embodiments, MTF biosynthesis is modulated by increasing serine in the culture medium or deregualting glycine cleavage enzymes.

The invention further features methods as described above, wherein pantothenate production is further enhanced by regulating pantothenate kinase activity (e.g., wherein pantothenate kinase activity is decreased). In one embodiment, CoaA is deleted and CoaX is downregulated. In another embodiment, CoaX is deleted and CoaA is downregulated. In yet another embodiment, CoaX and CoaA are downregulated. The invention further features methods as described above, wherein the microorganisms are cultured under conditions of excess serine. The invention further features methods as described above, wherein the microorganisms have the pantothenate biosynthetic pathway deregulated such that pantothenate production is independent of β-alanine feed.

Products synthesized according to the processes of the invention are also featured, as are compositions that include pantothenate produced according to said processes. Recombinant microorganisms for use in the processes of the invention are also featured. In one embodiment, the invention features a recombinant microorganism for the enhanced production of pantothenate having a deregulated pantothenate biosynthetic pathway and a deregulated MTF biosynthetic pathway. In another embodiment, the invention features a recombinant microorganism for the enhanced production of pantothenate having a deregulated pantothenate biosynthetic pathway, a deregulated MTF biosynthetic pathway and a deregulated ilv pathway. Microorganisms can flier have reduced pantothenate kinase activity. Preferred microorganisms belong to the genus *Bacillus*, for example *Bacillus subtilis*.

As described above, certain aspects of the invention, feature processes for the enhanced production of panto-compounds (e.g., pantoate and/or pantothenate) that involve culturing microorganisms having at least a deregulated pantothenate biosynthetic pathway. The term "pantothenate biosynthetic pathway" includes the biosynthetic pathway involving pantothenate biosynthetic enzymes (e.g., polypeptides encoded by biosynthetic enzyme-encoding genes), compounds (e.g., substrates, intermediates or products), cofactors and the like utilized in the formation or synthesis of pantothenate. The term "pantothenate biosynthetic pathway" includes the biosynthetic pathway leading to the synthesis of pantothenate in microorganisms (e.g., in vivo) as well as the biosynthetic pathway leading to the synthesis of pantothenate in vitro.

As used herein, a microorganism "having a deregulated pantothenate biosynthetic pathway" includes a microorganism having at least one pantothenate biosynthetic enzyme deregulated (e.g., overexpressed) (both terms as defined herein) such that pantothenate production is enhanced (e.g., as compared to pantothenate production in said microorganism prior to deregulation of said biosynthetic enzyme or as compared to a wild-type microorganism). The term "pantothenate" includes the free acid form of pantothenate, also referred to as "pantothenic acid" as well as any salt thereof (e.g., derived by replacing the acidic hydrogen of pantothenate or pantothenic acid with a cation, for example, calcium, sodium, potassium, ammonium, magnesium), also referred to as a "pantothenate salt." The term "pantothenate" also includes alcohol derivatives of pantothenate. Preferred pantothenate salts are calcium pantothenate or sodium pantothenate. A preferred alcohol derivative is pantothenol. Pantothenate salts and/or alcohols of the present invention include salts and/or alcohols prepared via conventional methods from the free acids described herein. In another embodiment, a pantothenate salt is synthesized directly by a microorganism of the present invention. A pantothenate salt of the present invention can likewise be converted to a free acid form of pantothenate or pantothenic acid by conventional methodology. The term "pantothenate" is also abbreviated as "pan" herein.

Preferably, a microorganism shaving a deregulated pantothenate biosynthetic pathway includes a microorganism having at least one pantothenate biosynthetic enzyme deregulated (e.g., overexpressed) such that pantothenate production is 1 g/L or greater. More preferably, a microorganism "having a deregulated pantothenate biosynthetic pathway" includes a microorganism having at least one pantothenate biosynthetic enzyme deregulated (e.g., overexpressed) such that pantothenate production is 2 g/L or greater. Even more preferably, a microorganism "having a deregulated pantothenate biosynthetic pathway" includes a microorganism having at least one pantothenate biosynthetic enzyme deregulated (e.g., overexpressed) such that pantothenate production is 10 g/L, 20 g/L, 30 g/L, 40 g/L, 50 g 60 g/L, 70 g/L, 80 g/L, 90 g/L, or greater.

The term "pantothenate biosynthetic enzyme" includes any enzyme utilized in the formation of a compound (e.g., intermediate or product) of the pantothenate biosynthetic pathway. For example, synthesis of pantoate from α-ketoisovalerate (α-KIV) proceeds via the intermediate, ketopantoate. Formation of ketopantoate is catalyzed by the pantothenate biosynthetic enzyme PanB or ketopantoate hydroxymethyltransferase (the panB gene product). Formation of pantoate is catalyzed by the pantothenate biosynthetic enzyme PanE1 or ketopantoate reductase (the panE1 gene product). Synthesis of β-alanine from aspartate is catalyzed by the pantothenate biosynthetic enzyme PanD or aspartate-α-decarboxylase (the panD gene product). Formation of pantothenate from pantoate and β-alanine (e.g., condensation) is catalyzed by the pantothenate biosynthetic enzyme PanC or pantothenate synthetase (the panC gene product). Pantothenate biosynthetic enzymes may also perform an alternative function as enzymes in the HMBPA biosynthetic pathway described herein.

Accordingly, in one embodiment, the invention features a process for the enhanced production of pantothenate that includes culturing a microorganism having at least one pantothenate biosynthetic enzyme deregulated (e.g., deregulated such that pantothenate production is enhanced), said enzyme being selected, for example, from the group consisting of PanB (or ketopantoate hydroxymethyltransferase), PanC (or pantothenate synthetase), PanD (or aspartate-α-decarboxylase), PanE1 (or ketopantoate reductase). In another embodiment, the invention features a process for the enhanced production of pantothenate that includes culturing a microorganism having at least two pantothenate biosynthetic enzymes deregulated, said enzymes being selected, for example, from the group consisting of PanB (or ketopantoate hydroymethyltransferase), PanC (or pantothenate synthetase), PanD (or aspartate-α-decarboxylase), and PanE1 (or ketopantoate reductase). In another embodiment, the invention features a process for the enhanced production of pantothenate that includes culturing a microorganism having at least three pantothenate biosynthetic enzymes deregulated, said enzymes being selected, for example, from the group consisting of PanB (or ketopantoate hydroxymethyltransferase), PanC (or pantothenate synthetase) PanD (or aspartate-α-decarboxylase), and PanE1 (or ketopantoate reductase). In another embodiment, the invention features a process for the enhanced production of pantothenate that includes culturing a microorganism having at least four pantothenate biosynthetic enzymes deregulated, for example, a microorganism having PanB (or ketopantoate-α-hydroxymethyltransferase), PanC (or pantothenate synthetase), PanD (or aspartate decarboxylase), and PanE1 (or ketopantoate reductase) deregulated.

In another aspect, the invention features processes for the enhanced production of pantothenate that involve culturing microorganisms having a deregulated isoleucine-valine biosynthetic pathway. The term "isoleucine-valine biosynthetic pathway" includes the biosynthetic pathway involving isoleucine-valine biosynthetic enzymes (e.g., polypeptides encoded by biosynthetic enzyme-encoding genes), compounds (e.g., substrates, intermediates or products), cofactors and the like utilized in the formation or synthesis of conversion of pyruvate to valine or isoleucine. The term "isoleucine-valine biosynthetic pathway" includes the biosynthetic pathway leading to the synthesis of valine or isoleucine in microorganisms (e.g., in vivo) as well as the biosynthetic pathway leading to the synthesis of valine or isoleucine in vitro.

As used herein, a microorganism "having a deregulated isoleucine-valine (ilv) pathway" includes a microorganism having at least one isoleucine-valine (ilv) biosynthetic enzyme deregulated (e.g., overexpressed) (both terms as defined herein) such that isoleucine and/or valine and/or the valine precursor, α-ketoisovaerate (α-KIV) production is enhanced (e.g., as compared to isoleucine and/or valine and/or α-KIV production in said microorganism prior to deregulation of said biosynthetic enzyme or as compared to a wild-type microorganism). FIG. 1 includes a schematic representation of the isoleucine-valine biosynthetic pathway. Isoleucine-valine biosynthetic enzymes are depicted in bold italics and their corresponding genes indicated in italics. The term "isoleucine-valine biosynthetic enzyme" includes any enzyme utilized in the formation of a compound (e.g., intermediate or product) of the isoleucine-valine biosynthetic pathway. According to FIG. 1, synthesis of valine from pyruvate proceeds via the intermediates, acetolactate, α,βdihydroxyisovalerate (α,β-DHIV and α-ketoisovalerate (α-KIV). Formation of acetolactate from pyruvate is catalyzed by the isoleucine-valine biosynthetic enzyme acetohydroxyacid synthetase (the ilvBN gene products, or alternatively, the alsS gene product). Formation of α,β-DHIV from acetolactate is catalyzed by the isoleucine-valine biosynthetic enzyme acetohydroxyacid isomeroreductase (the ilvC gene product). Synthesis of α-KIV from α,β-DHIV is catalyzed by the isoleucine-valine biosynthetic enzyme dihydroxyacid dehydratase (the ilvD gene product). Moreover, valine and isoleucine can be interconverted with their respective α-keto compounds by branched chain amino acid transaminases. Isoleucine-valine biosynthetic enzymes may also perform an alternative function as enzymes in the HMBPA biosynthetic pathway described herein.

Accordingly, in one embodiment, the invention features a process for the enhanced production of pantothenate that includes culturing a microorganism having at least one isoleucine-valine (ilv) biosynthetic enzyme deregulated (e.g., deregulated such that valine and/or isoleucine and/or α-KIV production, is enhanced) said enzyme being selected, for example, from the group consisting of IlvBN, AlsS (or acetohydroxyacid synthetase), IlvC; (or acetohydroxyacid isomeroreductase) and IlvD (or dihydroxyacid dehydratase). In another embodiment, the invention features a process for the enhanced production of pantothenate that includes culturing a microorganism having at least two isoleucine-valine (ilv) biosynthetic enzymes deregulated, said enzyme being selected, for example, from the group consisting of IlvBN, AlsS (or acetohydroxyacid synthetase), IlvC (or acetohydroxyacid isomeroreductase) and IlvD (or dihydroxyacid dehydratase). In another embodiment, the invention features a process for the enhanced production of pantothenate that includes culturing a microorganism having at least three isoleucine-valine (ilv) biosynthetic enzymes deregulated, for example, said microorganism having IlvBN or AlsS (or acetohydroxyacid synthetase), IlvC (or acetohydroxyacid isomeroreductase) and IlvD (or dihydroxyacid dehydratase) deregulated.

As mentioned herein, enzymes of the pantothenate biosynthetic pathway and/or the isoleucine-valine (ilv) pathway have been discovered to have an alternative activity in the synthesis of [R]-3-(2-hydroxy-3-methyl-butyrylamino)-propionic acid ("HMBPA") or the [R]-3-(2-hydroxy-3-methylbutyrylamino)-propionic acid ("HMBPA") biosynthetic pathway. The term "[R]-3-(2-hydroxy-3-methyl-butyrylamino)-propionic acid ("HMBPA") biosynthetic pathway" includes the alternative biosynthetic pathway involving biosynthetic enzymes and compounds (e.g., substrates and the like) traditionally associated with the pantothenate biosynthetic pathway and/or isoleucine-valine (ilv) biosynthetic pathway utilized in the formation or synthesis of HMBPA. The term "HMBPA biosynthetic pathway" includes the biosynthetic pathway leading to the synthesis of HMBPA in microorganisms (e.g., in vivo) as well as the biosynthetic pathway leading to the synthesis of HMBPA in vitro.

The term "HMBPA" biosynthetic enzyme includes any enzyme utilized in the formation of a compound (e.g., intermediate or product) of the HMBPA biosynthetic pathway. For example, synthesis of 2-hydroxyisovaleric acid (α-HIV) from α-ketoisovalerate (α-KIV) is catalyzed by the panE1 or panE2 gene product (PanE1 is alternatively referred to herein as ketopantoate-reductase) and/or is catalyzed by the ilvC gene product (alternatively referred to herein as acetohydroxyacid isomeroreductase). Formation of HMBPA from β-alanine and α-HIV is catalyzed by the panC gene product (alternatively referred to herein as pantothenate synthetase).

The term "[R]-3-(2-hydroxy-3-methyl-butyrylamino)-propionic acid ("HMBPA")" includes the free acid form of HMBPA, also referred to as "[R]-3-(2-hydroxy-3-methyl-butyrylamino)-propionate" as well as any salt thereof (e.g., derived by replacing the acidic hydrogen of 3-(2-hydroxy-3-methyl-butyrylamino)-propionic acid or 3-(2-hydroxy-3-methyl-butyrylamino)-propionate with a cation, for example, calcium, sodium, potassium, ammonium, magnesium), also referred to as a "3-(2-hydroxy-3-methyl-butyrylamino)-propionic acid salt" or "HMBPA salt." Preferred HMBPA salts are calcium HMBPA or sodium HMBPA. HMBPA salts of the present invention include salts prepared via conventional methods from the free acids described herein. An HMBPA salt of the present invention can likewise be converted to a free acid form of 3-(2-hydroxy-3-methyl-butyrylamino)-propionic acid or 3-(2-hydroxy-3-methyl-butyrylamino)-propionate by conventional methodology.

Figure 2:
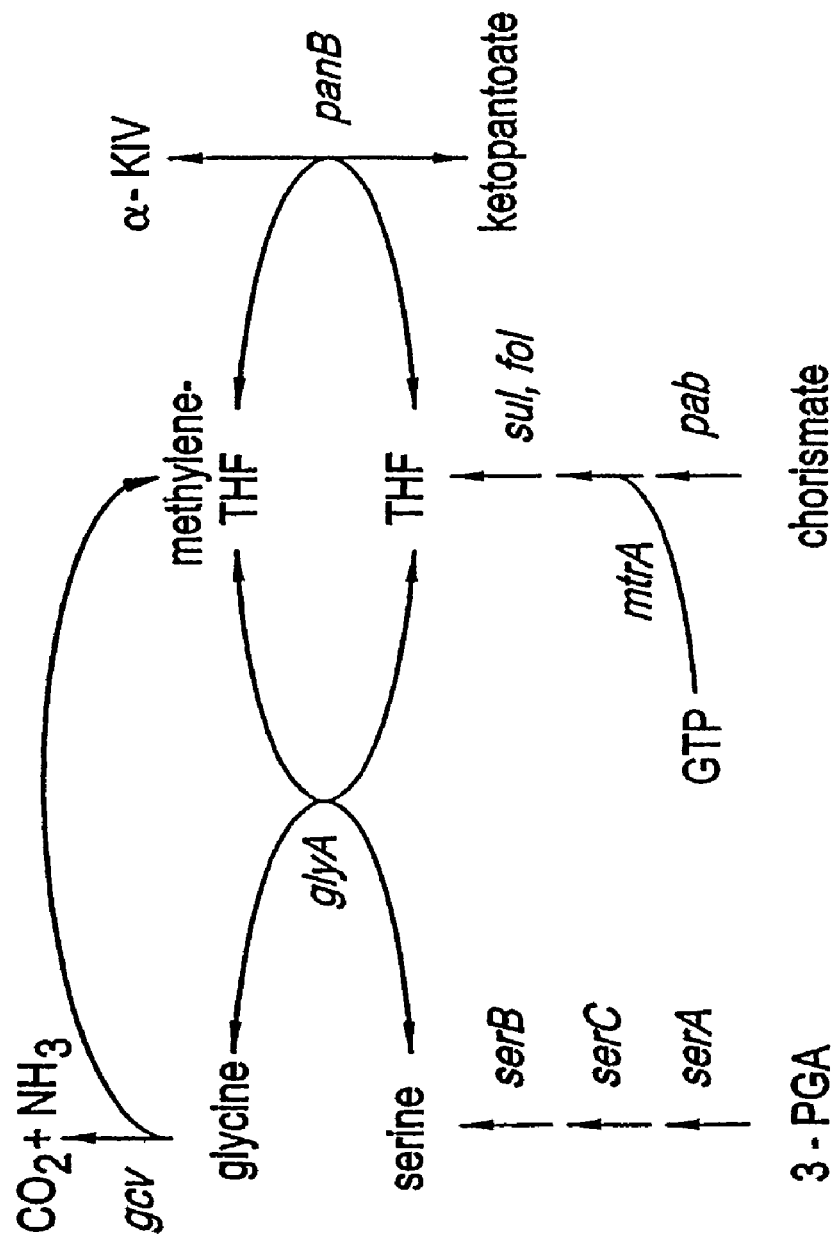
FIG. 2 is a schematic representation of the methylenetetrahydrofolate ("MTF") biosynthetic pathway in *E. coli* (and presumably in *B. subtilis*).

In preferred embodiments, the invention features processes for the enhanced production of panto-compounds (e.g., pantoate and/or pantothenate) that involve culturing a microorganism having a deregulated methylenetetrahydrofolate (MTF) biosynthetic pathway. The term "methylenetetrahydrofolate (MTF) biosynthetic pathway" refers to the biosynthetic pathway involving MTF biosynthetic enzymes (e.g., polypeptides encoded by biosynthetic enzyme-encoding genes), compounds (e.g., substrates, intermediates or products), cofactors and the like utilized in the formation or synthesis of the PanB substrate, MTF. The term "methylenetetrahydrofolate MTF) biosynthetic pathway" refers to the biosynthetic pathway leading to the synthesis of MTF in vivo (e.g., the pathway in E. coli, as depicted in FIG. 2) as well as the biosynthetic pathway leading to the synthesis of MTF in vitro. The term "methylenetetrahydrofolate (MTF) biosynthetic enzyme" includes any enzyme utilized in the formation of a compound (e.g., intermediate or product) of the methylenetetrahydrofolate (MTF) biosynthetic pathway.

The present invention is based, at least in part, on the discovery that deregulation of certain MTF biosynthetic enzymes results in enhanced production of MTF. A MTF biosynthetic enzyme, the deregulation of which results in enhanced MTF production, is termed a "MTF biosynthesis-enhancing enzyme". Exemplary "MTF biosynthesis-enhancing enzymes" are the serA gene product (3-phosphoglycerate dehydrogenase) and the glyA gene product (serine hydroxymethyl transferase). A microorganism "having a deregulated methylenetetrahydrofolate (MTF) biosynthetic pathway", is a microorganism having at least one MTF biosynthesis-enhancing enzyme deregulated (e.g., overexpressed) such that MTF production or biosynthesis is enhanced (e.g., as compared to MTF production in said microorganism prior to deregulation of said biosynthetic enzyme or as compared to a wild type microorganism).

In one embodiment, the invention features a process for the enhanced production of panto-compounds (e.g., pantoate and/or pantothenate) that includes culturing a microorganism having a deregulated "methylenetetrahydrofolate (MTF) biosynthetic pathway", as defined herein. In another embodiment, the invention features a process for the enhanced production of panto-compounds (e.g., pantoate and/or pantothenate) that includes culturing a microorganism having a deregulated MTF biosynthesis-enhancing enzyme. In preferred embodiments, the invention features processes for the enhanced production of panto-compounds (e.g. pantoate and/or pantothenate) that includes culturing a microorganism having a deregulated glyA gene product (serine hydroxymethyl transferase) and/or a deregulated serA gene product (3-phosphoglycerate dehydrogenase).

Yet another aspect of the present invention features processes for the enhanced production of pantothenate that include culturing microorganisms under culture conditions selected to favor pantothenate production, for example, by culturing microorganisms with excess serine (a glyA substrate) in the medium. The term "excess serine" includes serine levels increased or higher that those routinely utilized for culturing the microorganism in question. For example, culturing the Bacillus microorganisms described in the instant Examples is routinely done in the presence of about 0-2.5 g/L serine. Accordingly, excess serine levels can include levels of greater than 2.5 g/L serine, for example, between about 2.5 and 10 g/L serine. Excess serine levels can include levels of greater than 5 g/L serine, for example, between about 5 and 10 g/L serine.

Yet another aspect of the present invention features culturing the microorganisms described herein under conditions such that pantothenate production is further increased, for example, by increasing pantothenate and/or isoleucine-valine (ilv) biosynthetic pathway precursors and/or intermediates as defined herein (e.g., culturing microorganisms in the presence of excess β-alanine, valine and/or α-KIV) or, alternatively, further modifying said microorganisms such that they are capable of producing significant levels of β-alanine in the absence of a β-alanine feed (i.e., β-alanine independent microorganisms, as described in U.S. patent application Ser. No. 09/667,569).

Yet another aspect of the invention features further regulating pantothenate kinase activity in pantothenate-producing strains such that pantothenate production is enhanced. Pantothenate kinase is a key enzyme catalyzing the formation of Coenzyme A (CoA) from pantothenate (see e.g., U.S. patent application Ser. No. 09/09/667,569). Regulation of pantothenate kinase (e.g., decreasing the activity or level of pantothenate kinase) reduces the production of CoA, favoring pantothenate accumulation. In one embodiment, pantotheante kinase activity is decreased by deleting CoaA and downregulating CoaX activity (CoaA and CoaX are both capable of catalyzing the first step in CoA biosynthesis in certain microorganisms). In another embodiment, pantothenate kinase activity is decreased by deleting CoaX and downregulating CoaA. In yet another embodiment, pantotheante kinase activity is decreased by downregulating CoaA and CoaX activities.

Various aspects of the invention are described in further detail in the following subsections.

I. Targeting Genes Encoding Various Pantothenate and/or Isoleucine-Valine (ilv) and/or Methylenetetrahydrofolate (MTF) Biosynthetic Enzymes In one embodiment, the present invention features modifying or increasing the level of various biosynthetic enzymes of the pantothenate and/or isoleucine-valine (ilv) and/or methylenetetrahydrofolate (MTF) biosynthetic pathways. In particular, the invention features modifying various enzymatic activities associated with said pathways by modifying or altering the genes encoding said biosynthetic enzymes.

The term "gene", as used herein, includes a nucleic acid molecule (e.g., a DNA molecule or segment thereof) that, in an organism, can be separated from another gene or other genes, by intergenic DNA (i.e., intervening or spacer DNA which naturally flanks the gene and/or separates genes in the chromosomal DNA of the organism). Alternatively, a gene may slightly overlap another gene (e.g., the 3' end of a first gene overlapping the 5' end of a second gene), the overlapping genes separated from other genes by intergenic DNA. A gene may direct synthesis of an enzyme or other protein molecule (e.g., may comprise coding seqeunces, for example, a contiguous open reading frame (ORF) which encodes a protein) or may itself be functional in the organism. A gene in an organism, may be clustered in an operon, as defined herein, said operon being separated from other genes and/or operons by the intergenic DNA. An "isolated gene", as used herein, includes a gene which is essentially free of sequences which naturally flank the gene in the chromosomal DNA of the organism from which the gene is derived (i.e., is free of adjacent coding sequences that encode a second or distinct protein, adjacent structural sequences or the like) and optionally includes 5' and 3' regulatory sequences, for example promoter sequences and/or terminator, sequences. In one embodiment, an isolated gene includes predominantly ceding sequences for a protein (e.g., sequences which encode *Bacillus* proteins). In another embodiment, an isolated gene includes coding sequences for a protein (e.g., for a *Bacillus* protein)- and adjacent 5' and/or 3' regulatory sequences from the chromosomal DNA of the organism from which the gene is derived (e.g., adjacent 5' and/or 3' *Bacillus* regulatory sequences). Preferably, an isolated gene contains less than about 10 kb, 5 kb, 2 kb, 1 kb, 0.5 kb, 0.2 kb, 0.1 kb, 50 bp, 25 bp or 10 bp of nucleotide sequences which naturally flank the gene in the chromosomal DNA of the organism from which the gene is derived.

The term "operon" includes at least two adjacent genes or ORFs, optionally overlapping in sequence at either the 5' or 3' end of at least one gene or ORF. The term "operon" includes a coordinated unit of gene expression that contains a promoter and possibly a regulatory element associated with one or more adjacent genes or ORFs (e.g., structural genes encoding enzymes, for example, biosynthetic enzymes). Expression of the genes (e.g., structural genes) can be coordinately regulated, for example, by regulatory proteins binding to the regulatory element or by anti-termination of transcription. The genes of an operon (e.g., structural genes) can be transcribed to give a single mRNA that encodes all of the proteins.

A "gene having a mutation" or "mutant gene" as used herein, includes a gene having a nucleotide sequence which includes at least one alteration (e.g., substitution, insertion, deletion) such that the polypeptide or protein encoded by said mutant exhibits an activity that differs from the polypeptide or protein encoded by the wild-type nucleic acid molecule or gene. In one embodiment, a gene having a mutation or mutant gene encodes a polypeptide or protein having an increased activity as compared to the polypeptide or protein encoded by the wild-type gene, for example, when assayed under similar conditions (e.g., assayed in microorganisms, cultured at the same temperature). As used herein, an "increased activity" or "increased-enzymatic activity" is one that is at least 5% greater than that of the polypeptide or protein encoded by the wild-type nucleic acid molecule or gene, preferably at least 5-10% greater, more preferably at least 10-25% greater and even more preferably at least 25-50%, 50-75% or 75-100% greater than that of the polypeptide or protein encoded by the wild-type nucleic acid molecule or gene. Ranges intermediate to the above-recited values, e.g., 75-85%, 85-90%, 90-95%, are also intended to be encompassed by the present invention. As used herein, an "increased activity" or "increased enzymatic activity" can also include an activity that is at least 1.25-fold greater than the activity of the polypeptide or protein encoded by the wild-type gene, preferably at least 1.5-fold greater, more preferably at least 2-fold greater and even more preferably at least 3-fold, 4-fold, 5-fold, 10-fold, 20-fold, 50-fold, 100-fold greater than the activity of the polypeptide or protein encoded by the wild type gene.

In another embodiment, a gene having a mutation, or mutant gene encodes a polypeptide or protein having a reduced activity as compared to the polypeptide or protein encoded by the wild-type gene, for example, when assayed under similar conditions (e.g., assayed in microorganisms cultured at the same temperature). A mutant gene also can encode no polypeptide or have a reduced level of production of the wild-type polypeptide. As used herein, a "reduced activity" or "reduced enzymatic activity" is one that is at least 5% less than that of the polypeptide or protein encoded by the wild-type nucleic acid molecule or gene, preferably at least 5-10% less, more preferably at least 10-25% less and even more preferably at least 25-50%, 50-75% or 75-100% less than that of the polypeptide or protein encoded by the wild-type nucleic acid molecule or gene. Ranges intermediate to the above-recited values, e.g., 75-85%, 85-90%, 90-95%, are also intended to be encompassed by the present invention. As used herein, a "reduced activity" or "reduced enzymatic activity" can also include an activity that has been deleted or "knocked out" (e.g., approximately 100% less activity than that of the polypeptide or protein encoded by the wild-type nucleic acid molecule or gene).

Activity can be determined according to any well accepted assay for measuring activity of a particular protein of interest. Activity can be measured or assayed directly, for example, measuring an activity of a protein in a crude cell extract or isolated or purified from a cell or microorganism. Alternatively, an activity can be measured or assayed within a cell or microorganism or in an extracellular medium. For example, assaying for a mutant gene (i.e., said mutant encoding a reduced enzymatic activity) can be accomplished by expressing the mutated gene in a microorganism, for example, a mutant microorganism in which the enzyme is a temperature sensitive, and assaying the mutant gene for the ability to complement a temperature sensitive (Ts) mutant for enzymatic activity. A mutant gene that encodes an "increased enzymatic activity" can be one that complements the Ts mutant more effectively than, for example, a corresponding wild-type-gene. A mutant gene that encodes a "reduced enzymatic activity" is one that complements the Ts mutant less-effectively than, for example, a corresponding wild-type gene.

It will be appreciated by the skilled artisan that even a single substitution in a nucleic acid or gene sequence (e.g., a base substitution that encodes an amino acid change in the corresponding amino acid sequence) can dramatically affect the activity of an encoded polypeptide or protein as compared to the corresponding wild-type polypeptide or protein. A mutant gene (e.g., encoding a mutant polypeptide or protein), as defined herein, is readily distinguishable from a nucleic acid or gene encoding a protein homologue in that a mutant gene encodes a protein or polypeptide having an altered activity, optionally observable as a different or distinct phenotype in a microorganism expressing said mutant gene or producing said mutant protein or polypeptide (i.e., a mutant microorganism) as compared to a corresponding microorganism expressing the wild-type gene. By contrast, a protein homologue can have an identical or substantially similar activity, optionally phenotypically indiscernable when produced in a microorganism, as compared to a corresponding microorganism expressing the wild-type gene. Accordingly it is not, for example, the degree of sequence identity between nucleic acid molecules, genes, protein or polypeptides that serves to distinguish between homologues and mutants, rather it is the activity of the encoded protein or polypeptide that distinguishes between homologues and mutants: homologues having, for example, low (e.g., 30-50% sequence identity) sequence identity yet having substantially equivalent functional activities, and mutants, for example sharing 99% sequence identity yet having dramatically different or altered functional activities.

It will also be appreciated by the skilled artisan that nucleic acid molecules, genes, protein or polypeptides for use in the instant invention can be derived from any microorganisms having a MTF biosynthetic pathway, an ilv biosynthetic pathway or a pantothenate biosynthetic pathway. Such nucleic acid molecules, genes, protein or polypeptides can be identified by the skilled artisan using known techniques such as homology screening, sequence comparison and the like, and can be modified by the skilled artisan in such a way that expression or production of these nucleic acid molecules, genes, protein or polypeptides occurs in a recombinant microorganism (e.g., by using appropriate promotors, ribosomal binding sites, expression or integration vectors, modifying the sequence of the genes such that the transcription is increased (taking into account the preferable codon usage), etc., according to techniques described herein and those known in the art).

In one embodiment, the genes of the present invention are derived from a Gram positive microorganism organism (e.g., a microorganism which retains basic dye, for example, crystal violet, due to the presence of a Gram-positive wall surrounding the microorganism). The term "derived from" (e.g., "derived from" a Gram positive microorganism) refers to a gene which is naturally found in the microorganism (e.g., is naturally found in a Gram positive microorganism). In a preferred embodiment, the genes of the present invention are derived from a microorganism belonging to a genus selected from the group consisting of *Bacillus, Cornyebacterium* (e.g., *Cornyebacterium glutamicum*), *Lactobacillus, Lactococci* and *Streptomyces*. In a more preferred embodiment, the genes of the present invention are derived from a microorganism is of the genus *Bacillus*. In another preferred embodiment, the genes of the present invention are derived from a microorganism selected from the group consisting of *Bacillus subtilis, Bacillus lentimorbus, Bacillus lentus, Bacillus firmus, Bacillus pantothenticus, Bacillus amyloliquefaciens, Bacillus cereus, Bacillus circulans, Bacillus coagulans, Bacillus licheniformis, Bacillus megaterium, Bacillus pumilus, Bacillus thuringieisis, Bacillus halodurans,* and other Group 1 *Bacillus* species, for example, as characterized by 16S rRNA type. In another preferred embodiment, the gene is derived from *Bacillus brevis* or *Bacillus stearothermophilus*. In another preferred embodiment, the genes of the present invention are derived from a microorganism selected from the group consisting of *Bacillus licheniformis, Bacillus amyloliquefaciens, Bacillus subtilis,* and *Bacillus pumilus*. In a particularly preferred embodiment, the gene is derived from *Bacillus subtilis*(e.g., is *Bacillus subtilis*-derived). The term "derived from *Bacillus subtilis*" or "*Bacillus subtilis*-derived" includes a gene which is naturally found in the microorganism *Bacillus subtilis*. Included within the scope of the present invention are *Bacillus*-derived genes (e.g., *B. subtilis*-derived genes), for example, *Bacillus* or *B. subtilis* purR genes, serA genes, glyA genes, coax genes, coaA genes, pan genes and/or ilv genes.

In another embodiment, the genes of the present invention are derived from a Gram negative (excludes basic dye) microorganism. In a preferred embodiment, the genes of the present invention are derived from a microorganism belonging to a genus selected from the group consisting of *Salmonella* (e.g., *Salmonella typhimurium*), *Escherichia, Klebsiella, Serratia,* and *Proteus*. In a more preferred embodiment, the genes of the present invention are derived from a microorganism of the genus *Escherichia*. In an even more preferred embodiment, the genes of the present invention are derived from *Escherichia coli*. In another embodiment, the genes of the present invention are derived from *Saccharomyces*(e.g., *Saccharomyces cerevisiae*).

II. Recombinant Nucleic Acid Molecules and Vectors

The present invention further features recombinant nucleic acid molecules (e.g., recombinant DNA molecules) that include genes described herein (e.g., isolated genes), preferably *Bacillus* genes, more preferably *Bacillus subtilis*, genes even more preferably *Bacillus subtilis* pantothenate biosynthetic genes and/or isoleucine-valine (ilv) biosynthetic genes and/or methylenetetrahydrofolate (MIT) biosynthetic genes. The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). Preferably, a recombinant nucleic acid molecule (e.g., a recombinant DNA molecule) includes an isolated gene of the present invention operably linked to regulatory sequences. The phrase "operably linked to regulatory sequence(s)" means that the nucleotide sequence of the gene of interest is linked to the regulatory sequence(s) in a manner which allows for expression (e.g., enhanced, increased, constitutive, basal, attenuated, decreased or repressed expression) of the gene, preferably expression of a gene product encoded by the gene (e.g., when the recombinant nucleic acid molecule is included in a recombinant vector, as defined herein, and is introduced into a microorganism).

The term "regulatory sequence" includes nucleic acid sequences which affect (e.g., modulate or regulate) expression of other nucleic acid sequences (i.e., genes). In one embodiment, a regulatory sequence is included in a recombinant nucleic acid molecule in a similar or identical position and/or orientation relative to a particular gene of interest as is observed for the regulatory sequence and gene of interest as it appears in nature, e.g., in a native position and/or orientation. For example, a gene of interest can be included in a recombinant nucleic acid molecule operably linked to a regulatory sequence which accompanies or is adjacent to the gene of interest in the natural organism (e.g., operably linked to "native" regulatory sequences (e.g., to the "native" promoter). Alternatively, a gene of interest can be included in a recombinant nucleic acid molecule operably linked to a regulatory sequence which accompanies or is adjacent to another (e.g., a different) gene in the natural organism. Alternatively, a gene of interest can be included in a recombinant nucleic acid molecule operably linked to a regulatory sequence from another organism. For example, regulatory sequences from other microbes (e.g., other bacterial regulatory sequences, bacteriophage regulatory sequences and the like) can be operably linked to a particular gene of interest.

In one embodiment, a regulatory sequence is a non-native or non-naturally-occurring sequence (e.g., a sequence which has been modified, mutated, substituted, derivatized, deleted including sequences which are chemically synthesized). Preferred regulatory sequences include promoters, enhancers, termination signals, anti-termination signals and other expression control elements (e.g., sequences to which repressors or inducers bind and/or binding sites for transcriptional and/or translational regulatory proteins, for example, in the transcribed mRNA). Such regulatory sequences are described, for example, in Sambrook, J., Fritsh, E. F., and Maniatis, T. *Molecular Cloning: A Laboratory Manual 2nd, ed., Cold Spring Harbor Laboratory*, Cold Spring Harbor Laboratory Press, Cold Spring Harbor, N.Y., 1989. Regulatory sequences include those which direct constitutive expression of a nucleotide sequence in a microorganism (e.g., constitutive promoters and strong constitutive promoters), those which direct inducible expression of a nucleotide sequence in a microorganism (e.g., inducible promoters, for example, xylose inducible promoters) and those which attenuation or repress expression of a nucleotide sequence in a microorganism (e.g., attenuation signals or repressor binding sequences, for example, a PurR binding site). It is also within the scope of the present invention to regulate expression of a gene of interest by removing or deleting regulatory sequences, for example, sequences involved in the negative regulation of transcription can be removed such that expression of a gene of interest is enhanced.

In one embodiment, a recombinant nucleic acid molecule of the present invention includes a nucleic acid sequence or gene that encodes at least one-bacterial gene product (e.g., a pantothenate biosynthetic enzyme, an isoleucine-valine biosynthetic enzyme and/or a methylenetetrahydrofolate (MTF) biosynthetic enzyme) operably linked to a promoter or promoter sequence. Preferred promoters of the present invention include *Bacillus* promoters and/or bacteriophage promoters (e.g., bacteriophage which infect *Bacillus*). In one embodiment, a promoter is a *Bacillus* promoter, preferably a strong *Bacillus* promoter (e.g., a promoter associated with a biochemical housekeeping gene in *Bacillus* or a promoter associated with a glycolytic pathway gene in *Bacillus*). In another embodiment, a promoter is a bacteriophage promoter. In a preferred embodiment, the promoter is from the bacteriophage SP01. In a particularly preferred embodiment, a promoter is selected from the group consisting of $P_{15}$, $P_{26}$ or $P_{veg}$, having for example, the following respective seqeunces:
GCTATTGACGACAGCTATGGTTCACT-GTCCACCAACCAAAACTGTGCTCAGT ACCGC-CAATATTTCTCCCTGAGGGGTACAAA-GAGGTGTCCCTAGAAGAGAT CCACGCTGTGTAAAAATTTTACAAAAAG-GTATTGACTTTCCCTACAGGGTGT GTAATAATT-TAATTACAGGCGGGGGCAACCCCGCCTGT (SEQ ID NO: 1), GCCTACCTAGCTTCCAAGAAAGATATC-CTAACAGCACAAGAGCGGAAAGAT GTTGTTCTA-CATCCAGAACAACCTCTGCTAAAATTC-CTGAAAAATTTTGCA AAAAGTTGTTGACTTTATCTACAAGGT-GTGGTATAATAATCTTAACAACAGC AGGACGC (SEQ ID NO:2), and GAGGAATCATAGAATTTTGT-CAAAATAATTTTATTGACAACGTCTTAITAAC GTTGATATAATTTAAATTFATTGA-CAAAAATGGGCTCGTGTTGTACAATA AATGTAGT-GAGGTGGATGCAATG (SEQ ID NO:3). Additional preferred promoters include tef (the translational elongation factor (TEF) promoter) and pyc (the pyruvate carboxylase (PYC) promoter), which promote high level expression in *Bacillus* (e.g., *Bacillus subtilis*). Additional preferred promoters, for example, for use in Gram positive microorganisms include, but are not limited to, amy and SPO2 promoters. Additional preferred promoters, for example, for use in Gram negative microorganisms include, but are not limited to, cos, tac, trp, tet, typ-tet, lpp, lac, lpp-lac, lacIQ, T7, T5, T3, gal, trc, ara, SP6, λ-PR or λ-PL.

In another embodiment, a recombinant nucleic acid molecule of the present invention includes a terminator sequence or terminator sequences (e.g., transcription terminator sequences). The term "terminator sequences" includes regulatory sequences that serve to terminate transcription of mRNA. Terminator sequences (or tandem transcription terminators) can further serve to stabilize mRNA (e.g., by adding structure to mRNA), for example, against nucleases.

In yet another embodiment, a recombinant nucleic acid molecule of the present invention includes sequences that allow for detection of the vector containing said sequences (i.e., detectable and/or selectable markers), for example, genes that encode antibiotic resistance sequences or that overcome auxotrophic mutations, for example, trpC, drug markers, fluorescent markers, and/or colorimetric markers (e.g., lacZ/β-galactosidase). In yet another embodiment, a recombinant nucleic acid molecule of the present invention includes an artificial ribosome binding site (RBS) or a sequence that gets transcribed into an artificial RBS. The term "artificial ribosome binding site (RBS)" includes a site within an mRNA molecule (e.g., coded with in DNA) to which a ribosome binds (e.g., to initiate translation) which differs from a native RBS (e.g., a RBS found in a naturally-occurring gene) by at least one nucleotide. Preferred artificial RBSs include about 5-6, 7-8, 9-10, 11-12, 13-14, 15-16, 17-18, 19-20, 21-22, 23-24, 25-26, 27-28, 29-30 or more nucleotides of which about 1-2, 3-4, 5-6, 7-8, 9-10, 11-12, 13-15 or more differ from the native RBS (e.g., the native RBS of a gene of interest, for example, the native panB RBS. TAAACATGAG-GAGGAGAAAACATG (SEQ ID NO:4) or the native panD RBS ATTCGAGAAATGGAGAGAATATAATATG (SEQ ID NO:5)). Preferably, nucleotides that differ are substituted such that they are identical to one or more nucleotides of an ideal RBS when optimally aligned for comparisons. Ideal RBSs include, but are not limited to, AGAAAGGAGGTGA (SEQ ID NO:6), TTAAGAAAGGAGGTGANNNNATG (SEQ ID NO: 7), TTAGAAAGGAGGTGANNNNNATG (SEQ ID NO: 8), AGAAAGGAGGTGANNNNNNNATG (SEQ ID NO: 9), and AGAAAGGAGGTGANNNNNNATG (SEQ ID NO: 10). Artificial RBSs can be used to replace the naturally-occurring or native RBSs associated with a particular gene. Artificial RBSs preferably increase translation of a particular gene. Preferred artificial RBSs (e.g., RBSs for increasing the translation of panB, for example, of *B. subtilis* panB) include CCCTCTAGAAGGAGGAGAAAACATG (SEQ ID NO:11) and CCCTCTAGAGGAGGAGAAAA-CATG (SEQ ID NO:12). Preferred artificial RBSs (e.g., RBSs for increasing the translation of panD, for example, of *B. subtilis* panD) include TTAGAAAGGAGGATT-TAAATATG (SEQ ID NO:13), TTAGAAAGGAGGTT- TAATTAATG (SEQ ID NO:14), TTAGAAAGGAGGT-GATITAAATG (SEQ ID NO:15), TTAGAAAGGAGGTGTTTAAAATG (SEQ ID NO: 16), ATTCGAGAAAGGAGG TGAATATAATATG (SEQ ID NO:17), ATTCGAGAAAGGAGGTGAATAATAATG (SEQ ID NO: 18), and ATTCGTAGAAAGGAGGTGAAT-TAATATG (SEQ ID NO:19).

The present invention further features vectors (e.g., recombinant vectors) that include nucleic acid molecules (e.g., genes or recombinant nucleic acid molecules comprising said genes) as described herein. The term "recombinant vector" includes a vector (e.g., plasmid, phage, phasmid, virus, cosmid or other purified nucleic acid vector) that has been altered, modified or engineered such that it contains greater, fewer or different nucleic acid sequences than those included in the native or natural nucleic acid molecule from which the recombinant vector was derived. Preferably, the recombinant vector includes a biosynthetic enzyme-encoding gene or recombinant nucleic acid molecule including said gene, operably linked to regulatory sequences, for example, promoter sequences, terminator sequences and/or artificial ribosome binding sites (RBSs), as defined herein. In another embodiment, a recombinant vector of the present invention includes sequences that enhance replication in bacteria (e.g., replication-enhancing sequences). In one embodiment, replication-enhancing sequences function in *E. coli*. In another embodiment, replication-enhancing sequences are derived from pBR322.

In yet another embodiment, a recombinant vector of the present invention includes antibiotic resistance sequences. The term "antibiotic resistance sequences" includes sequences which promote or confer resistance to antibiotics on the host organism (e.g., *Bacillus*). In one embodiment, the antibiotic resistance sequences are selected from the group consisting of cat (chloramphenicol resistance) sequences, tet (tetracycline resistance) sequences, erm (erythromycin resistance) sequences, neo (neomycin resistance) sequences, kan (kanamycin resistence) sequences and spec (spectinomycin resistance) sequences. Recombinant-vectors of the present invention can further include homologous recombination sequences (e.g., sequences designed to allow recombination of the gene of interest into the chromosome of the host organism). For example, bpr, vpr, or amyE sequences can be used as homology targets for recombination into the host chromosome. It will further be appreciated by one of skill in the art that the design of a vector can be tailored depending on such factors as the choice of microorganism to be genetically engineered, the level of expression of gene product desired and the like.

III. Recombinant Microorganisms

The present invention further features microorganisms, i.e., recombinant microorganisms, that include vectors or genes (e.g., wild-type and/or mutated genes) as described herein. As used herein, the term "recombinant microorganism" includes a microorganism (e.g., bacteria, yeast cell fungal cell, etc.) that has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring microorganism from which it was derived.

In one embodiment, a recombinant microorganism of the present invention is a Gram positive organism (e.g., a microorganism which retains basic dye, for example, crystal violet, due to the presence of a Gram-positive wall surrounding the microorganism). In a preferred embodiment, the recombinant microorganism is a microorganism belonging to a genus selected from the group consisting of *Bacillus. Cornyebacterium* (e.g., *Cornyebacterium glutamicum*), *Lactobacillus, Lactococci* and *Streptomyces*. In a more preferred embodiment, the recombinant microorganism is of the genus *Bacillus*. In another preferred embodiment, the recombinant microorganism is selected from the group consisting of *Bacillus subtilis, Bacillus lenitimorbus, Bacillus lentus, Bacillus firmus, Bacillus pantothenticus, Bacillus amyloliquefaciens, Bacillus cereus, Bacillus circulans, Bacillus coagulans, Bacillus licheniformis, Bacillus megaterium, Bacillus pumilus, Bacillus thuringiensis, Bacillus halodurans*, and other Group 1 *Bacillus* species, for example, as characterized by 16S rRNA type. In another preferred embodiment, the recombinant microorganism is *Bacillus brevis* or *Bacillus stearothermophilus*. In another preferred embodiment, the recombinant microorganism is selected from the group consisting of *Bacillus licheniformis, Bacillus amyloliquefaciens, Bacillus subtilis*, and *Bacillus pumilus*.

In another embodiment, the recombinant microorganism is a Gram negative (excludes basic dye) organism. In a preferred embodiment, the recombinant microorganism is a microorganism belonging to a genus selected from the group consisting of *Salmonella*(e.g., *Salmonella typhimurium*), *Escherichia, Klebsiella, Serratia*, and *Proteus*. In a more preferred embodiment, the recombinant microorganism is of the genus *Escherichia*. In an even more preferred embodiment, the recombinant microorganism is *Escherichia coli*. In another embodiment, the recombinant microorganism is *Saccharomyces* (e.g., *Saccharomyces cerevisiae*).

A preferred "recombinant" microorganism of the present invention is a microorganism having a deregulated pantothenate biosynthesis pathway or enzyme, a deregulated isoleucine valine (ilv) biosynthetic pathway or enzyme and/or a modified or deregulated methylenetetrahydrofolate (MTF) biosynthetic pathway or enzyme and/or a modified or term "deregulated" or "deregulation" includes the alteration or modification of at least one gene in a microorganism that encodes an enzyme in a biosynthetic pathway, such that the level or activity of the biosynthetic enzyme in the microorganism is altered or modified. Preferably, at least one gene that encodes an enzyme in a biosynthetic pathway is altered or modified such that the gene product is enhanced or increased. The phrase "deregulated pathway" includes a biosynthetic pathway in which more than one gene that encodes an enzyme in a biosynthetic pathway is altered or modified such that the level or activity of more than one biosynthetic enzyme is altered or modified. The ability to "deregulate" a pathway (e.g., to simultaneously deregulate more than one gene in a given biosynthetic pathway) in a microorganism in some cases arises from the particular phenomenon of microorganisms in which more than, one enzyme (e.g., two or three biosynthetic enzymes) are encoded by genes occurring adjacent to one another on a contiguous piece of genetic material termed an "operon" (defined herein). Due to the coordinated regulation of genes included in an operon, alteration or modification of the single promoter and/or regulatory element can result in alteration or modification of the expression of each gene product encoded by the operon. Alteration or modification of a regulatory element can include, but is not limited to removing the endogenous promoter and/or regulatory element(s), adding strong promoters, inducible promoters or multiple promoters or removing regulatory sequences such that expression of the gene products is modified, modifying the chromosomal location of a gene or operon, altering nucleic acid sequences adjacent to a gene or operon (or within an operon) such as a ribosome binding site, increasing the copy number of a gene or operon, modifying proteins (e.g., regulatory proteins, suppressors, enhancers, transcriptional activators and the like) involved in transcription of a gene or operon and/or translation of a gene product or gene products of a gene or operon, respectively, or any other conventional means of deregulating expression of genes routine in the art (including but not limited to use of antisense nucleic acid molecules, for example, to block expression of repressor proteins). Deregulation can also involve altering the coding region of one or more genes to yield, for example, an enzyme that is feedback resistant or has a higher or lower specific activity.

In another preferred embodiment, a recombinant microorganism is designed or engineered such that at least one pantothenate biosynthetic enzyme, at least one isoleucine-valine biosynthetic enzyme, and/or at least one MTF biosynthetic enzyme is overexpressed. The term "overexpressed" or "overexpression" includes expression of a gene product (e.g., a biosynthetic enzyme) at a level greater than that expressed prior to manipulation of the microorganism or in a comparable microorganism which has not been manipulated. In one embodiment the microorganism can be genetically designed or engineered to overexpress a level of gene product greater than that expressed in a comparable microorganism which has not been engineered.

Genetic, engineering can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, for example, to block expression of repressor proteins). Genetic engineering can also include deletion of a gene, for example, to block a pathway or to remove a repressor.

In another embodiment, the microorganism can be physically or environmentally manipulated to overexpress a level of gene product greater than that expressed prior to manipulation of the microorganism or in a comparable microorganism which has not been manipulated. For example, a microorganism can be treated with or cultured in the presence of an agent known or suspected to increase transcription of a particular gene and/or translation of a particular gene product such that transcription and/or translation are enhanced or increased. Alternatively, a microorganism can be cultured at a temperature selected to increase transcription of a particular gene and/or translation of a particular gene product such that transcription and/or translation are enhanced or increased.

IV. Culturing and Fermenting Recombinant Microorganisms

The term "culturing" includes maintaining and/or growing a living microorganism of the present invention (e.g., maintaining and/or growing a culture or strain). In one embodiment, a microorganism of the invention is cultured in liquid media. In another embodiment, a microorganism of the invention is cultured in solid media or semi-solid media. In a preferred embodiment, a microorganism of the invention is cultured in media (e.g., a sterile, liquid medium) comprising nutrients essential or beneficial to the maintenance and/or growth of the microorganism (e.g., carbon sources or carbon substrate, for example carbohydrate, hydrocarbons, oils, fats, fatty acids, organic acids, and alcohols, nitrogen sources, for example, peptone, yeast extracts, meat extracts, malt extracts, soy meal, soy flour, soy grits, urea, ammonium sulfate, ammonium, chloride, ammonium nitrate and ammonium phosphate; phosphorus sources, for example, phosphoric acid, sodium and potassium salts thereof; trace elements, for example, magnesium, iron, manganese, calcium, copper, zinc, boron, molybdenum, and/or cobalt salts; as well as growth factors such as amino acids, vitamins, growth promoters and the like).

Preferably, microorganisms of the present invention are cultured under controlled pH. The term "controlled pH" includes any pH which results in production of the desired product (e.g., pantoate and/or pantothenate). In one embodiment microorganisms are cultured at a pH of about 7. In another embodiment, microorganisms are cultured at a pH of between 6.0 and 8.5. The desired pH may be maintained by any number of methods known to those skilled in the art.

Also preferably, microorganisms of the present invention are cultured under controlled aeration. The term "controlled aeration" includes sufficient aeration (e.g., oxygen) to result in production of the desired product (e.g., pantoate and/or pantothenate). In one embodiment, aeration is controlled by regulating oxygen levels in the culture, for example, by regulating the amount of oxygen dissolved in culture media. Preferably, aeration of the culture is controlled by agitating the culture. Agitation may be provided by a propeller or similar mechanical agitation equipment, by revolving or shaking the cuture vessel (e.g., tube or flask) or by various pumping equipment. Aeration may be further controlled by the passage of sterile air or oxygen through the medium (e.g., through the fermentation mixture). Also preferably, microorganisms of the present invention are cultured without excess foaming (e.g., via addition of antifoaming agents).

Moreover, microorganisms of the present invention can be cultured under controlled temperatures. The term "controlled temperature" includes any temperature which results in production of the desired product (e.g., pantoate and/or pantothenate). In one embodiment, controlled temperatures include temperatures between 15° C. and 95° C. In another embodiment, controlled temperatures include temperatures between 15° C. and 70° C. Preferred temperatures are between 20° C. and 55° C., more preferably between 30° C. and 50° C.

Microorganisms can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture or fermentation. In a preferred embodiment, the microorganisms are cultured in shake flasks. In a more preferred embodiment, the microorganisms are cultured in a fermentor (e.g., a fermentation process). Fermentation processes of the present invention include, but are not limited to, batch, fed-batch and continuous processes or methods of fermentation. The phrase "batch process" or "batch fermentation" refers to a system in which the composition of media, nutrients, supplemental additives and the like is set at the beginning of the fermentation and not subject to alteration during the fermentation, however, attempts may be made to control such factors as pH and oxygen concentration to prevent excess media acidification and/or microorganism death. The phrase "fed-batch process" or "fed-batch" fermentation refers to a batch fermentation with the exception that one or more substrates or supplements are added (e.g., added in increments or continuously) as the fermentation progresses. The phrase "continuous process" or "continuous fermentation" refers to a system in which a defined fermentation media is added continuously to a fermentor and an equal amount of used or "conditioned" media is simultaneously removed, preferably for recovery of the desired product (e.g., pantoate and/or pantothenate). A variety of such processes have been developed and are well-known in the art.

The phrase "culturing under conditions such that a desired compound is produced" includes maintaining and/or growing microorganisms under conditions (e.g., temperature, pressure, pH, duration, etc.) appropriate or sufficient to obtain production of the desired compound or to obtain desired yields of the particular compound being produced. For example, culturing is continued for a time sufficient to produce the desired amount of a compound (e.g., pantoate and/or pantothenate). Preferably, culturing is continued for a time sufficient to substantially reach suitable production of the compound (e.g., a time sufficient to reach a suitable concentration of pantoate and/or pantothenate or suitable ratio of pantoate and/or pantothenate:HMBPA). In one embodiment, culturing is continued for about 12 to 24 hours. In another embodiment, culturing is continued for about 24 to 36-hours, 36 to 48 hours, 48 to 72 hours, 72 to 96 hours, 96 to 120 hours, 120 to 144 hours, or greater than 144 hours. In yet another embodiment, microorganisms are cultured under conditions such that at least about 5 to 10 g/L of compound are produced in about 36 hours, at least about 10 to 20 g/L compound are produced in about 48 hours, or at least about 20 to 30 g/L compound in about 72 hours. In yet another embodiment, microorganisms are cultured under conditions such that at least about 5 to 20 g/L of compound are produced in about 36 hours, at least about 20 to 30 g/L compound are produced in about 48 hours, or at least about 30 to 50 or 60 g/L compound in about 72 hours. In yet another embodiment, microorganisms are cultured under conditions such that at least about 40 to 60 g/L of compound are produced in about 36 hours, or at least about 60 to 90 g/L compound are produced in about 48 hours. It will be appreciated by the skilled artisan that values above the upper limits of the ranges recited may be obtainable by the processes described herein, for example, in a particular fermentation run or with a particular engineered strain.

Preferably, a production method of the present invention results in production of a level of pantothenate that is "enhanced as compared to an appropriate control". The term "appropriate control", as defined herein, includes any control recognized by the skilled artisan as being approriate for determining enhanced, increased, or elevated levels of desired product. For example, where the process features culturing a microorganism having a deregulated pantothenate biosynthetic pathway and said microorganism further has a deregulated MTF biosynthetic pathway (e.g., has been engineered such that at least one MTF biosynthetic enzyme is deregulated, for example, overexpressed) an appropriate control includes a culture of the microorganism before or absent manipulation of the MTF enzyme or pathway (i.e., having only the pantothenate biosynthetic pathway deregulated). Likewise, where the process features culturing a microorganism having a deregulated pantothenate biosynthetic pathway and a deregulated ilv biosynthetic pathway and said microorganism further has a deregulated MTF biosynthetic pathway (i.e., has been engineered such that at least one MTF biosynthetic enzyme is deregulated, for example, overexpressed) an appropriate control includes a culture of the microorganism before or absent manipulation of the MTF enzyme or pathway (i.e., having only the pantothenate biosynthetic pathway and ilv biosynthetic pathway deregulated). Comparison need not be performed in each process practiced according to the present invention. For example, a skilled artisan can determine appropriate controls empirically from performing a series of reactions (e.g., test tube cultures; shake flask cultures, fermentations), for example, under the same or similar conditions. Having appreciated a routine production level, for example, by a particular strain, the artisan is able to recognize levels that are enhanced, increased or elevated over such levels. In other words, comparison to an appropriate control includes comparison to a predetermined values (e.g., a predetermined control).

Thus, in an embodiment wherein an appropriately engineered strain produces 40 g/L pantothenate in 36 hours (prior to manipulation such that pantothenate production is enhanced), production of 50, 60, 70 or more g/L pantothenate (after manipulation, for example, manipulation such that at least one MTF biosynthetic enzyme is overexpressed) exemplifies enhanced production. Likewise, in an embodiment wherein an appropriately engineered strain produces 50 g/L pantothenate in 48 hours (prior to manipulation such that pantothenate production is enhanced), production of 60, 70, 80, 90 or more g/L pantothenate (after manipulation, for example, manipulation such that at least one MTF biosynthetic enzyme is overexpressed) exemplifies enhanced production.

The methodology of the present invention can further include a step of recovering a desired compound (e.g., pantoate and/or pantothenate). The term "recovering" a desired compound includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), dialysis, filtration, concentration, crystallization, recrystallization, pH adjustment, lyophilization and the like. For example, a compound can be recovered from culture media by first removing the microorganisms from the culture. Media are then passed through or over a cation exchange resin to remove cations and then through or over an anion exchange resin to remove inorganic anions and organic acids having stronger acidities than the compound of interest. The resulting compound can subsequently be converted to a salt (e.g., a calcium salt) as described herein.

Preferably, a desired compound of the present invention is "extracted", "isolated" or "purified" such that the resulting preparation is substantially free of other media components (e.g., free of media components and/or fermentation byproducts). The language "substantially free of other media components" includes preparations of the desired compound in which the compound is separated from media components or fermentation byproducts of the culture from which it is produced. In one embodiment, the preparation has greater than about 80% (by dry weight) of the desired compound (e.g., less than about 20% of other media components or fermentation byproducts), more preferably greater than about 90% of the desired compound (e.g., less than about 10% of other media components or fermentation byproducts), still more preferably greater than about 95% of the desired compound (e.g., less than about 5% of other media components or fermentation byproducts), and most preferably greater than about 98-99% desired compound (e.g., less than about 1-2% other media components or fermentation byproducts). When the desired compound has been derivatized to a salt, the compound is preferably further free of chemical contaminants associated with the formation of the salt. When the desired compound has been derivatized to an alcohol, the compound is preferably further free of chemical contaminants associated with the formation of the alcohol.

In an alternative embodiment, the desired compound is not purified from the microorganism, for example, when the microorganism is biologically non-hazardous (e.g., safe). For example, the entire culture (or culture supernatant) can be used as a source of product (e.g., crude product). In one embodiment, the culture (or culture supernatant) is used without modification. In another embodiment, the culture (or culture supernatant) is concentrated. In yet another embodiment, the culture (or culture supernatant) is dried or lyophilized.

In yet another embodiment, the desired compound is partially purified. The term "partially purified" includes media preparations that have had at least some processing, for example, treatment (e.g., batch treatment) with a commercial resin. In preferred embodiments, the "partially purified" preparation has greater than about 30% (by dry weight) of the desired compound, preferably greater than about 40% of the desired compound, more preferably greater than about 50% of the desired compound, still more preferably greater than about 60% of the desired compound, and most preferably greater than about 70% desired compound. "Partially purified" preparations also preferably have 80% or less (by dry weight) of the desired compound (i.e., are less pure than "extracted", "isolated" or "purified" preparations, as defined herein).

Depending on the biosynthetic enzyme or combination of biosynthetic enzymes manipulated, it may be desirable or necessary to provide (e.g., feed) microorganisms of the present invention at least one biosynthetic precursor such that the desired compound or compounds are produced. The term "biosynthetic precursor" or "precursor" includes an agent or compound which, when provided to, brought into contact with, or included in the culture medium of a microorganism, serves to enhance or increase biosynthesis of the desired product. In one embodiment, the biosynthetic precursor or precursor is aspartate. In another embodiment, the biosynthetic precursor or precursor is β-alanine. The amount of aspartate or β-alanine added is preferably an amount that results in a concentration in the culture medium sufficient to enhance productivity of the microorganism (e.g., a concentration sufficient to enhance production of pantoate and/or pantothenate). Biosynthetic precursors of the present invention can be added in the form of a concentrated solution or suspension (e.g., in a suitable solvent such as water or buffer) or in the form of a solid (e.g., in the form of a powder). Moreover, biosynthetic precursors of the present invention can be added as a single aliquot, continuously or intermittently over a given period of time. The term "excess β-alanine" includes β-alanine levels increased or higher that those routinely utilized for culturing the microorganism in question. For example, culturing the *Bacillus* microorganisms described in the instant Examples is routinely done in the presence of about 0-0.01 g/L β-alanine. Accordingly, excess β-alanine levels can include levels of about 0.01-1, preferably about 1-20 g/L.

In yet another embodiment, the biosynthetic precursor is valine. In yet another embodiment, the biosynthetic precursor is α-ketoisovalerate. Preferably, valine or α-ketoisovalerate is added in an amount that results in a concentration in the medium sufficient for production of the desired product (e.g., pantoate and/or pantothenate) to occur. The term "excess α-KIV" includes α-KIV levels increased or higher that those routinely utilized for culturing the microorganism in question. For example, culturing the *Bacillus* microorganisms described in the instant Examples is routinely done in the presence of about 0-0.01 g/L α-KIV. Accordingly, excess α-KIV levels can include levels of about 0.01-1 preferably about 1-20 g/L α-KIV. The term "excess valine" includes valine levels increased or higher that those routinely utilized for culturing the microorganism in question. For example, culturing the *Bacillus* microorganisms described in the instant Examples is routinely done in the presence of about 0-0.5 g/L valine. Accordingly, excess valine levels can include levels of about 0.5-5 g/L, preferably about 5-20 g/L valine.

In yet another embodiment, the biosynthetic precursor is serine. Preferably, serine is added in an amount that results in a concentration in the medium sufficient for production of the desired product (e.g., pantoate and/or pantothenate) to occur. Excess serine (as defined herein) can also be added according to the production processes described herein, for example, for the enhanced production of pantothenate. The skilled artisan will appreciate that extreme excesses of biosynthetic precursors can result in microorganism toxicity. Biosynthetic precursors are also referred to herein as "supplemental biosynthetic substrates".

Another aspect of the present invention includes biotransformation processes which feature the recombinant microorganisms described herein. The term "biotransformation process", also referred to herein as "bioconversion processes", includes biological processes which results in the production (e.g., transformation or conversion) of appropriate substrates and/or intermediate compounds into a desired product.

The microorganism(s) and/or enzymes used in the biotransformation reactions are in a form allowing them to perform their intended function (e.g., producing a desired compound). The microorganisms can be whole cells, or can be only those portions of the cells necessary to obtain the desired end result. The microorganisms can be suspended (e.g., in an appropriate solution such as buffered solutions or media), rinsed (e.g., rinsed free of media from culturing the microorganism), acetone-dried, immobilized (e.g., with polyacrylamide gel or k-carrageenan or on synthetic supports, for example, beads, matrices and the like), fixed, cross-linked or permeablized (e.g., have permeablized membranes and/or walls such that compounds, for example, substrates, intermediates or products can more easily pass through said membrane or wall).

This invention is further illustrated by the following examples which should not be construed as limiting. The contents of all references, patents and published patent applications cited throughout this application are incorporated herein by reference.

EXAMPLES

Example I

Panto-Compound Production Strains

In developing *Bacillus* strains for the production of pantothenate, various genetic manipulations are made to genes and enzymes involved in the pantothenate biosynthetic pathway and the isoleucine-valine (ilv) pathway (FIG. 1) as described in U.S. patent application Ser. No. 09/400,494 and U.S. patent application Ser. No. 09/667,569. For example, strains having a deregulated panBCD operon and/or having deregulated panE1 exhibit enhanced pantothenate production (when cultured in the presence of β-alanine and α-ketoisovalerate (α-KIV)). Strains further deregulated for ilvBNC and ilvD exhibit enhanced pantothenate production in the presence of only β-alanine. Moreover, it is possible to achieve β-alanine independence by further deregulating panD.

An exemplary pantothenate production strain is PA824, a tryptophan prototroph, Spec and Tet resistant, deregulated for panBCD at the panBCD locus, deregulated for panE1 at the panE1 locus (two genes in the *B. subtilis* genome are homologous to *E. coli* panE, panE1 and panE2, the former encoding the major ketopantoate reductase involved in pantothenate production, while panE2 does not contribute to pantothenate synthesis (U.S. patent application Ser. No. 09/400,494), deregulated for ilvD at the ilvD locus, overexpressing an ilvBNC cassette at the amyE locus, and overexpressing panD at the bpr locus. PA824 routinely yields approximately 40-50 g/L pantothenate, when cultured for 48 hours in 14 L fermentor vessels according to standard fermentation procedures (see e.g., provisional Patent Application Ser. No. 60/263,053 or provisional Patent Application Ser. No. 60/262,995, incorporated by reference herein). Briefly, batch media (4.5 L) containing trace elements is inoculated with shake flask cultures of PA824. The fermentations are controlled for temperature (e.g., 43° C.), dissolved $O_2$, and pH, and are run as a glucose limited fed batch process. After the initial batched glucose is consumed, glucose concentrations are maintained between about 0 and 1 g/L by continuous feeding of fresh FEED media pH is set at 7.2, monitored, and maintained by feeding either a $NH_3$- or a $H_3PO_4$-solution. The dissolved oxygen concentration. [$pO_2$] is maintained at about 10-30% by regulation of the agitation and aeration rate. Foaming is controlled by addition of an appropriate antifoam agent. The pantothenate titer in the fermentation broth is determined (by HPLC analysis) after removal of the cells by centrifugation.

A second exemplary strain is PA668. PA668 is a derivative of PA824 that contains extra copies of $P_{26}$panB amplified at the vpr and/or panB locus. PA668 was constructed using a panB expression vector (pAN636) which allows for selection of multiple copies using chloramphenicol. Briefly, a pAN636 NotI restriction fragment (excluding vector sequences) was ligated and then used to transform PA824 with selection on plates containing 5 μg/ml chloramphenicol. Transformants resistant to 30 μg/ml chloramphenicol were isolated and screened for pantothenate production in 48 hour test tube cultures. The isolates produce about 10 percent more pantothenate than PA824. In 10-L fermentations, a first strain, PA668-24, produces pantothenate in amounts comparable to PA824 cultured under similar conditions (e.g., ~45-50 g/L at 36 hours). After 36 hours, when pantothenate production routinely begins to slow with PA824, PA668-2A continues to produce significant levels of pantothenate (e.g., ~60-65 g/l pantothenate at 48 hours). A second strain, PA668-24, produces pantothenate at an even faster rate, reaching 60-70 g/L after 48 hours.

Figure 4:
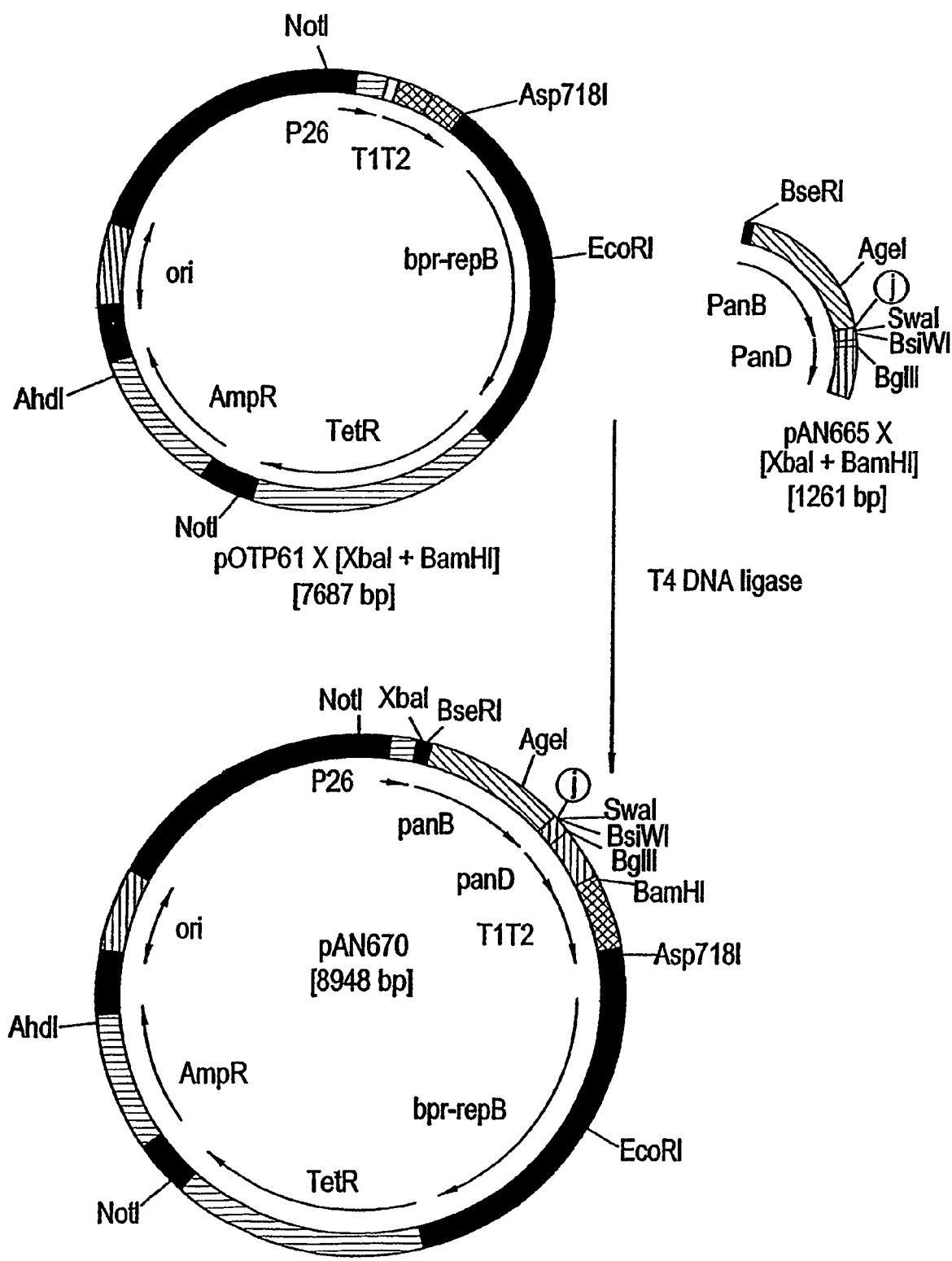
FIG. 4 is a schematic representation of the construction of the plasmid pAN670.

A third production strain, PA721B-39, was engineered to further include an amplifiable $P_{26}$panBpanD cassette as follows. First, a single expression cassette was constructed that is capable of integrating both panB and panD at the bpr locus. Combining both genes into one expression cassette simplifies the resulting strain by eliminating an antibiotic resistance marker. The $P_{26}$panBpanD expression cassette was constructed to include each of two different panD ribosome binding sites (the RBSs having previously been synthesized and tested in International Public. No. WO 01/21772 and U.S. Patent Application Ser. No. 60/262,995). The cassette further included the synthetic panB gene ribosome binding site (RBS1), but the design permits future alteration of the panB RBS by simple oligonucleotide cassette substitution. In the first step of construction, the panB gene was joined to the two panD gene cassettes as illustrated in FIG. 3 for the construction of pAN665. Next, the resulting panBpanD cassettes were transferred to *B. subtilis* expression vector pOTP61 as illustrated in FIG. 4. A summary of the essential features of each plasmid (pAN670 and pAN674) constructed is presented in Table 1.

TABLE 1

Plasmids containing various *B. subtilis* panBpanD gene expression cassettes.

| Plasmid | panD RBS | Vector | Host strain |
|---------|----------|--------|-------------|
| pAN665 | Standard | pASK-1BA3 | *E. coli* |
| pAN670 | " | pOTP61 | *B. subtilis* |
| pAN669 | ND-C2 | pASK-1BA3 | *E. coli* |
| pAN674 | " | pOTP61 | *B. subtilis* |

These new plasmids combine production of extra PanB and PanD from a single vector and were predicted to produce increased levels of PanB relative to the panB expression vector (pAN636) present in PA668. The strategy to install the P26 panBpanD vectors in pantothenate production strains took advantage of genetic linkage between bpr and panE1. A derivative of PA824 was first constructed that is cured of the resident panD expression cassette by transforming the strain with chromosomal DNA isolated from PA930 (panE1::cat) and selecting for resistance to chloramphenicol. The resulting transformants were screened for sensitivity to tetracycline, and two Tet-sensitive isolates named PA715 were saved. This strain is the host strain for testing the P26panBpanD vectors (see below). In order to restore the P26panE1 cassette in PA715, each vector was first transformed into a strain (PA328) that contains P26panE1 but does not contain a cassette integrated at the bpr locus. PA328 does contain the P26 panBCD locus although it is not engineered for overproduction of α-KIV. Transformants of PA328 resistant to tetracycline were obtained using the appropriate NotI restriction fragments from the two vectors and the resulting strains were named PA710 and PA714.

The next step was to transfer the cassettes into PA715 so they could be evaluated in the PA824 strain background. This was accomplished by isolating chromosomal DNA from strains PA710 and PA714 and using each of the two DNAs separately to transform PA715, with selection for resistance to tetracycline. Tetracycline resistant transformants were screened for sensitivity to chloramphenicol; this identifies the desired transformants that have also acquired the P26panE1 gene from the donor DNA by linkage with the P26panBpanD cassettes at the bpr locus. Chloramphenicol-sensitive isolates derived from transformations in which PA710 or PA714 chromosomal DNA was used as the donor were obtained. The isolates that produced the highest pantothenate titers in test tube culture assays were saved. These strains were named PA717 and PA721, respectively. Duplicate test tube cultures of the new strains, as well as PA824 and PA715, were grown in SVY+10 g/L aspartate at 43° C. for 48 hours and then assayed for pantothenate, HMBPA, and β-alanine. In addition, extracts from each of the strains were run on a SDS-PAGE gel. The results of the test tube culture assays are presented in Table 2.

TABLE 2

Production of pantothenate by strains PA717 and PA721 grown in SVY plus 10 g/l aspartate.

| Strain | panBD cassette | [pan] (g/L) | [HMBPA] (g/L) | [β-ala] (g/L) |
|---|---|---|---|---|
| PA824 | — | 4.9 | 0.94 | 2.5 |
| " | | 4.6 | 0.79 | 2.3 |
| PA715 | NONE | 1.7 | <0.1 | 0.5 |
| " | " | 1.7 | <0.1 | 0.4 |
| PA717-24 | pAN670 | 4.8 | 0.34 | 1.3 |
| " | " | 4.9 | 0.40 | 1.3 |
| PA721-35 | pAN674 | 5.7 | 0.50 | 1.4 |
| " | " | 5.3 | 0.40 | 1.3 |
| PA721-39 | pAN674 | 4.1 | 0.38 | 2.0 |
| " | " | 4.6 | 0.40 | 2.2 |

As expected, each of the new strains produced more pantothenate and β-alamine than PA715. Two of the strain (PA717-24 and PA721-39) produced about as much pantothenate as PA824 while PA721-35 produced more pantothenate PA824. All tree of the new strains produced less HMBPA than PA824. The protein gel analysis showed that the three new strains produce more PanB than any of the control strains.

Strains PA717-24, PA721-35, and PA721-39 were also evaluated in shake flask cultures in a soy-flour based medium. As shown Table 3, these strains with the amplifiable $P_{26}$panBpanD cassette produced pantothenate and HMBPA at levels similar to the levels seen with PA668-2 and PA668-24 which both contain separate amplifiable $P_{26}$panB and $P_{26}$panD cassettes.

TABLE 3

Shake Flask Experiment 48 Hours

| Medium | Strain | HMBPA (g/l) | PAN (g/l) |
|---|---|---|---|
| Soy flour + Glucose | PA668-2 | 1.2 | 6.8 |
| | PA668-24 | 1.6 | 5.2 |
| | PA717-24 | 2.0 | 5.9 |
| | PA721-35 | 2.6 | 7.0 |
| | PA721-39 | 2.5 | 8.6 |
| Soy flour + Maltose | PA668-2 | 0.0 | 9.0 |
| | PA668-24 | 0.4 | 10.4 |
| | PA717-24 | 0.7 | 8.6 |
| | PA721-35 | 1.0 | 9.2 |
| | PA721-39 | 0.4 | 9.1 |

Conditions: 40 ml medium/200 ml baffled shake flask, 4X Bioshield covers, 300 rpm, 2.5% inoculum (1.0 ml).
Soy Medium: 20 g/l Cargill 200/20 soy flour, 8 g/l (NH4)2SO4, 5 g/l glutamate, 1 × PSTE, 0.1M phosphate pH 7.2 and 0.3M MOPS pH 7.2. 60 g/l glucose or maltose w/10 mM Mg and 1.4 mM Ca.
Average of duplicate flasks.

In addition to producing pantothenate (as well as other panto-compounds depicted in FIG. 1 and described herein), it has been demonstrated that certain strains engineered for producing commercial quantities of desired panto-compound also produce a by-product identified as 3-(2-hydroxy-3-methyl-butyrylamino)-propionic acid (HMBPA)(also referred to herein as "β-alanine 2-(R)-hydroxyisolvalerate", "β-alanine 2-hydroxyisolvalerate", "β-alanyl-α-hydroxyisovalarate" and/or "fantothenate"). (The term "fantothenate" is also abbreviated as "fan" herein.)

HMBPA is the condensation product of [R]-α-hydroxyisovaleric acid (α-HIV) and β-alanine, catalyzed by the PanC enzyme. α-HIV is generated by reduction of α-KIV, a reaction that is catalyzed by the α-keto reductases PanE (e.g., PanE1 and/or PanE2) and/or IlvC. Thus it has been proposed that there exist at least two pathways in microorganisms that compete for α-KIV, the substrate for the biosynthetic enzyme PanB, namely the pantothenate biosynthetic pathway and the HMBPA biosynthetic pathway. (A third and fourth pathway competing for α-KIV are those resulting in the production of valine or leucine from α-KIV, see e.g., FIG. 1). At least the pantothenate biosynthetic pathway and the HMBPA biosynthetic pathway further produce competitive substrates for the enzyme PanC, namely α-HIV and pantoate. Production of HMBPA can have significant effects on pantothenate production. For example, the HMBPA pathway can compete with the pantothenate pathway for precursors (α-KIV and β-alanine) and for some of the enzymes (PanC, PanD, PanE1, and/or IlvC). In addition, because the structure of HMBPA is similar to that of pantothenate, it may have the undesirable property of negatively regulating one or more steps in the pantothenate pathway. Based on the identification of HMBPA, U.S. Provisional Patent Application Ser. No. 60/262,995 teaches that production of pantothenate can be improved or optimized by any means which favor use of substrates (α-KIV and β-alanine) and/or enzymes (PanC, PanD, PanE1, and/or IlvC) in pantothenate biosynthetic processes as compared to HMBPA biosynthetic processes.

Example II

Increasing Pantothenate Production by Increasing Serine Availability

At least one method for optimizing pantothenate production involves regulating the availability of serine in the microorganism cultures. In particular, it can be demonstrated that increasing the availability of serine leads to increased pantothenate production (e.g., relative to HMBPA production), whereas decreasing the availability of serine leads to decreased pantothenate production relative to HMBPA production. This method is based on the understanding that the compound, methylenetetrahydrofolate (MTF), which is derived from serine, donates a hydroxymethyl group to α-KIV during the pantothenate biosynthetic reaction to yield ketopantoate (see e.g., FIGS. 1 and 2). Thus, regulating serine levels is one means of effectively regulating ketopantoate levels and, in turn, regulating pantoate and/or pantothenate production in appropriately engineered microorganisms. To demonstrate this regulation, PA824 was grown in test tube cultures of SVY glucose plus 5 g/L β-alanine and ±5 g/L serine for 48 hours and 43° C.

TABLE 4

Production of pantothenate and HMBPA by PA824 with and without the addition of serine

| serine added at 5 g/L | $OD_{600}$ | [pan] g/L | [HMBPA] g/L |
|---|---|---|---|
| − | 16.3 | 4.9 | 0.84 |
| − | 14.0 | 4.5 | 0.80 |
| + | 13.1 | 6.4 | 0.56 |
| + | 12.9 | 6.0 | 0.62 |

As demonstrated by the data presented in Table 4, addition of serine increases the level of production of pantothenate (while conversely decreasing HMBPA production).

Example III

Engineering Bacterial Cells with Increased Amounts of Serine Hydroxylmethyl Transferase, the glyA Gene Product As an alternative to feeding serine, another method of increasing serine levels and/or serine utilization levels (and accordingly, methylenetetrahydrofolate levels) in order to regulate pantothenate production levels is to increase synthesis or the activity of 3-phosphoglycerate dehydrogenase or of serine hydroxymethyl transferase (the serA and glyA gene products, respectively), thereby increasing serine and methylenetetrahydrofolate biosynthesis in appropriately engineered microorganisms.

Expression of the glyA gene was increased by transforming *B. subtilis* cells with an expression cassette containing the *B. subtilis* glyA gene cloned downstream of a strong, constitutive promoter. To construct the expression cassette the primers RY417 and RY418 depicted in Table 5 were used to amplify the glyA gene by PCR from chromosomal DNA isolated from *B. subtilis* PY79.

TABLE 5

Primers used in the amplification of *B. subtilis* glyA and serA

| | | |
|---|---|---|
| RY405 | SEQ ID NO: 20 | CCCTCTAGAGGAGGAGAAAACATGTTTCGAGTATTGGTCTCAGACAAAATG |
| RY406 | SEQ ID NO: 21 | CCCGGATCCAATTATGGCAGATCAATGAGCTTCACAGACACAA |
| RY417 | SEQ ID NO: 22 | GGATCTAGAGGAGGTGTAAACATGAAACATTTACCTGCGCAAGACGAA |
| RY418 | SEQ ID NO: 23 | CGGGGATCCCCCATCAACAATTACACACTTCTATTGATTCTAC |

Figure 5:
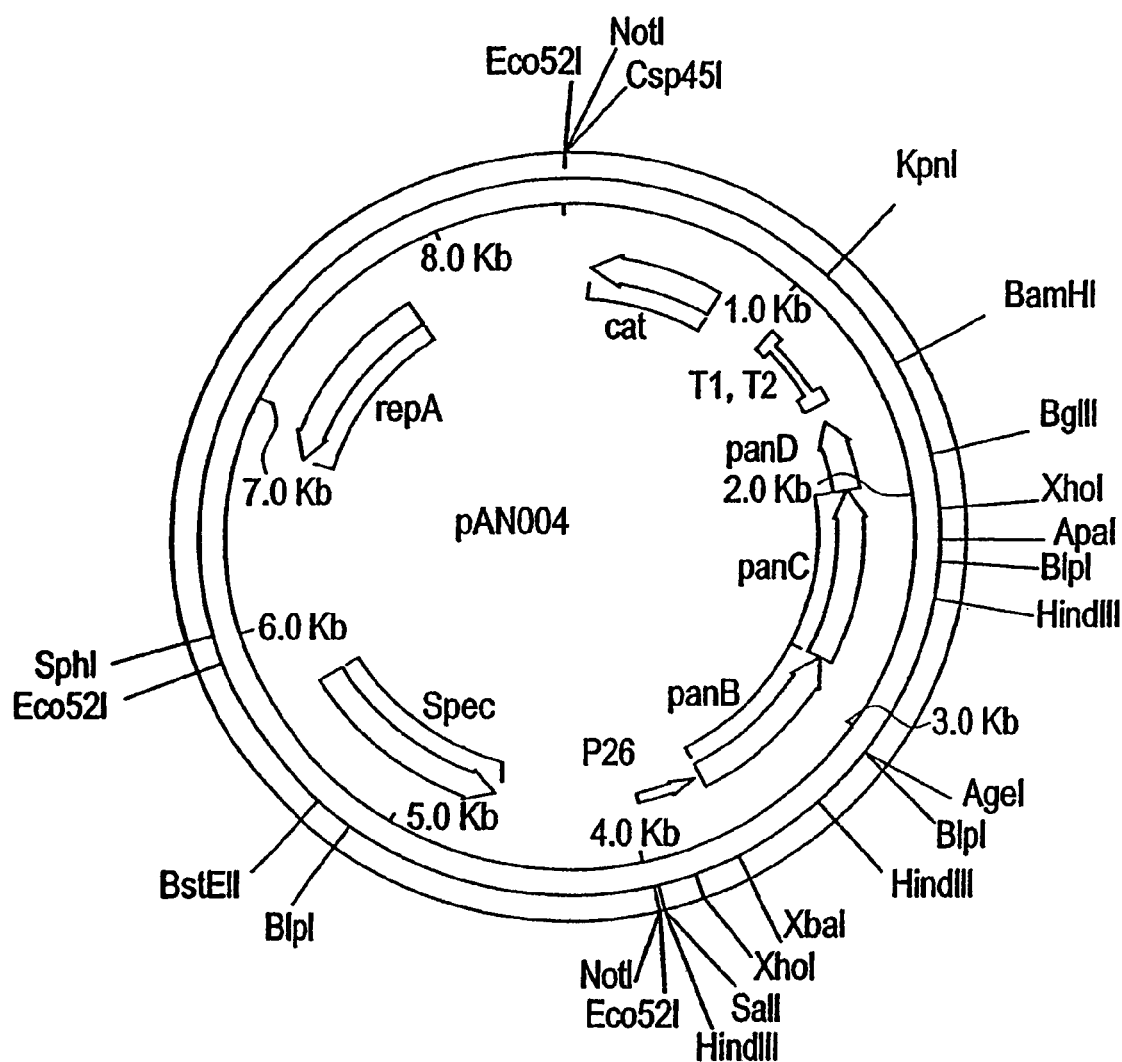
FIG. 5 is a schematic representation of the plasmid pAN004.
Figure 6:
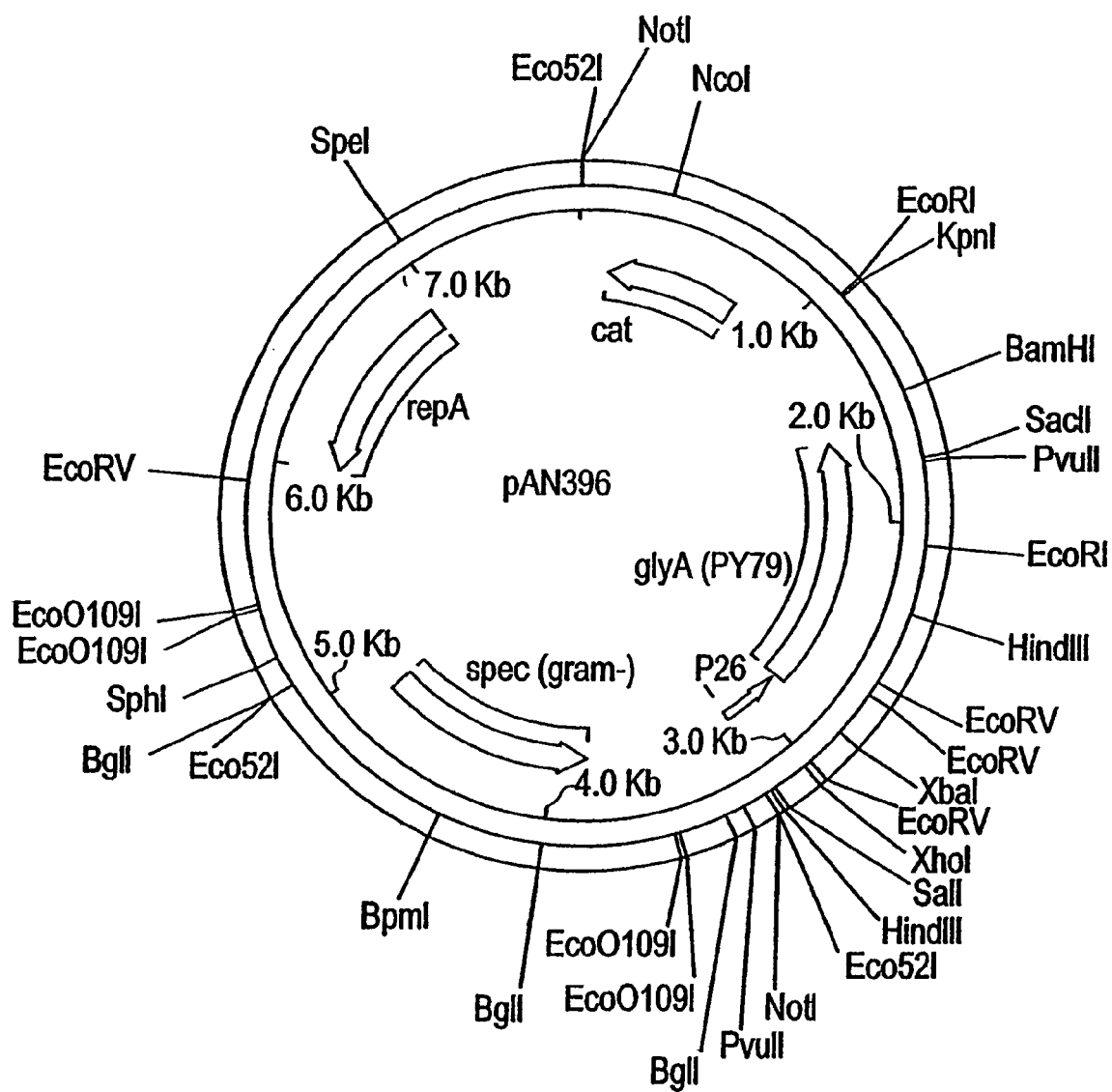
FIG. 6 is a schematic representation of the plasmid pAN396.

RY417 contains the RBS2 synthetic ribosome binding site just downstream from an XbaI site. The amplified DNA was then cut with XbaI and BamHI and cloned between the XbaI and BamHI sites in vector pAN004 (FIG. 5) to yield plasmid pAN396 (FIG. 6; SEQ ID NO:24). The pAN004 vector contains the phage SP01 $P_{26}$ promoter immediately upstream of the XbaI cloning site to drive expression of the cloned glyA gene. Just downstream of the expression cassette, pAN396 contains a cat gene that functions in *B. subtilis*. To transform *B. subtilis*, the NotI DNA fragment containing the $P_{26}$glyA cassette and cat gene was isolated from pAN396, self-ligated, and transformed into competent cells of *B. subtilis* PY79. Several chloramphenicol resistant transformants were selected and named PA1007 and PA1008. Chromosomal DNA was isolated from each of these strains and used to transform competent cells of PA721B-39 and PA824 to yield strains PA1011 and PA1014, respectively. SDS polyacrylamide gel electrophoresis of cell extracts of selected isolates of PA1011 and PA1014 confirmed that these strains contained increased amounts of the glyA gene product as compared to their parent strains PA721B-39 (described in Example I) and PA824 (described in International Public. No. WO 01/21772). To test the effect of increasing glyA expression on pantothenate production, PA1011 and PA1014 were grown in test tube cultures of SVY glucose plus 5 g/L β-alanine at 43° C. for 48 hours. As shown by the data presented in Table 6, PA 014 produced more pantothenate (4.5 g/L) than its parent strain PA824 (3.2 g/L). Similarly, PA1011 produced on average more pantothenate (4.35 g/L) than its parent strain PA721B-39 (4.05 g/L).

TABLE 6

Production of pantothenate and HMBPA by PA1011 and PA1014 compared to PA721B-39 and PA824.

| Strain | $OD_{600}$ | Pantothenate g/L | HMBPA g/L |
|---|---|---|---|
| PA1014 #1 | 14 | 4.5 | 0.27 |
| PA1014 #2 | 15 | 4.5 | 0.31 |
| PA824 | 16 | 3.1 | 0.31 |
| PA824 | 15 | 3.3 | 0.28 |
| PA1011 #1 | 17 | 4.5 | 0.24 |
| PA1011 #2 | 12 | 4.2 | 0.27 |
| PA721B-39 | 18 | 4.0 | 0.22 |
| PA721B-39 | 16 | 4.1 | 0.25 |

Example IV

Figure 7:
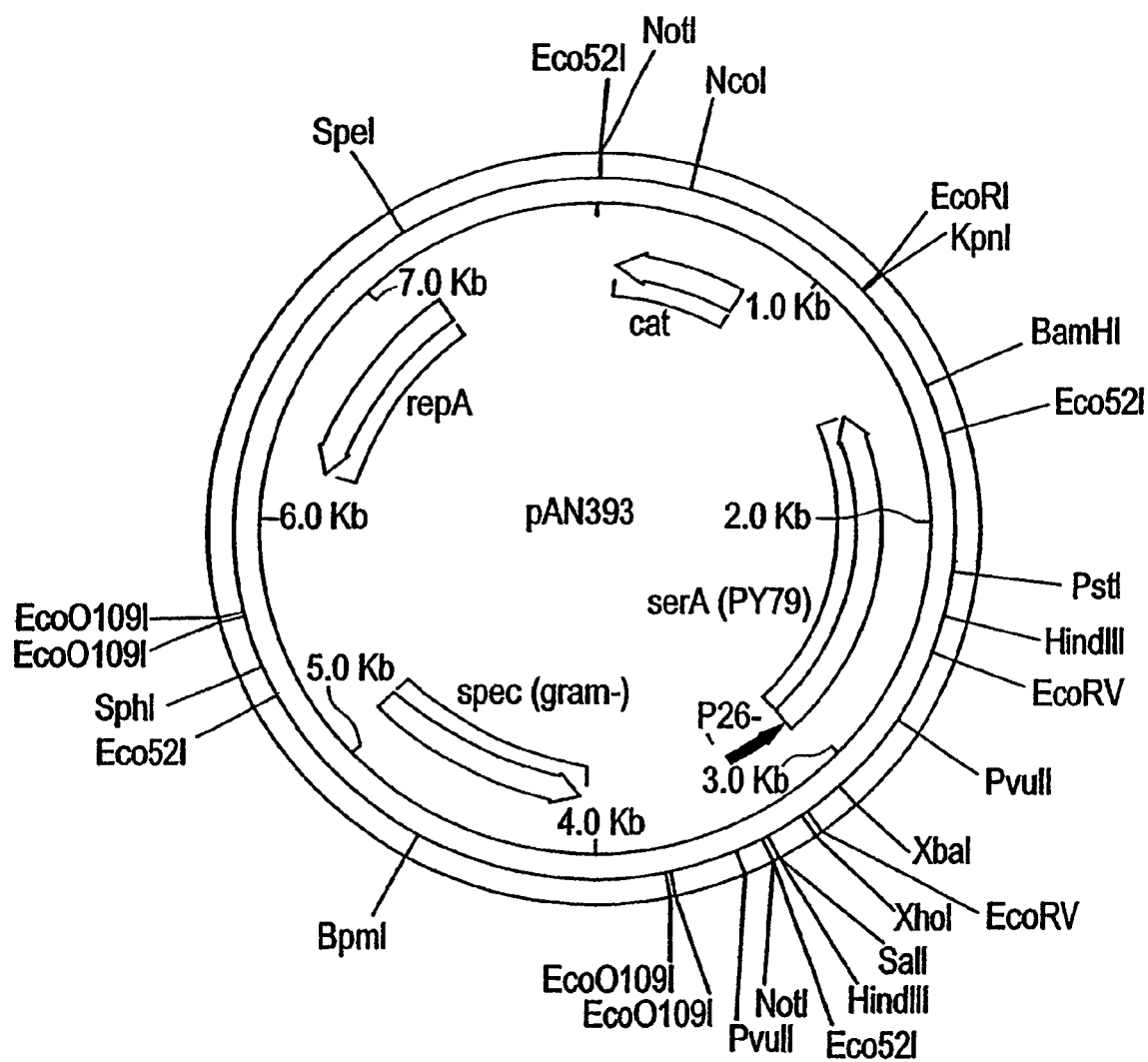
FIG. 7 is a schematic representation of the plasmid pAN393.

Engineering Bacterial Cells with Increased Amounts of 3-Phosphoglycerate Dehydrogenase, the serA Gene Product The product of the sera gene, 3-phosphoglycerate dehydrogenase, is the first committed enzyme in the pathway to serine biosynthesis (see FIG. 2). Since serine is one of the substrates for the synthesis of MTF, we engineered the overexpression of the sera gene to increase serine levels in the cell. In a manner similar to that described above for the glyA gene in Example III, expression of the serA gene was increased by transforming *B. subtilis* cells with an expression cassette containing the *B. subtilis* sera gene cloned downstream of a strong, constitutive promoter. To construct the expression cassette the primers RY405 and RY406 depicted in Table 5 were used to amplify the sera gene by PCR from chromosomal DNA isolated from *B. subtilis* PY79. The amplified DNA was then cut with XbaI and BamHI and cloned between the XbaI and BamHI sites in vector pAN004 (FIG. 5) to yield plasmid pAN393 (FIG. 7; SEQ ID NO:25). To transform *B. subtilis*, the NotI DNA fragment containing the P26 sera cassette and cat gene was isolated from pAN393, self-ligated, and transformed into competent cells of *B. subtilis* PY79. Several chloramphenicol resistant transformants were selected and named PA1004 and PA1005. Chromosomal DNA was isolated from each of these strains and used to transform competent cells of PA721B-39 and PA824 to yield strains PA1010 and PA1013, respectively. SDS polyacrylamide gel electrophoresis of cell extracts of selected isolates of PA1010 and PA1013 confirmed that these strains contained increased amounts of the sera gene product as compared to their parent strains PA721B-39 and PA824.

To test the effect of increasing sera expression on pantothenate production, PA1010 and PA1013 were grown in test tube cultures of SVY glucose plus 5 g/L β-alanine at 43° C. for 48 hours. As shown by the data presented in Table 7, PA1010 produced on average more pantothenate (4.7 g/L) than its parent strain PA721B-39 (4.1 g/L). Similarly, PA1013 produced on average more pantothenate (4.1 g/L) than its parent strain PA824 (3.1 g/L).

TABLE 7

Production of pantothenate and HMBPA by PA1010 and PA1013 compared to PA721B-39 and PA824.

| Strain | $OD_{600}$ | Pantothenate g/L | HMBPA g/L |
|---|---|---|---|
| PA1010 #3 | 16 | 4.8 | 0.23 |
| PA1010 #5 | 15 | 4.5 | 0.26 |
| PA1010 #6 | 22 | 4.7 | 0.24 |

TABLE 7-continued

Production of pantothenate and HMBPA by PA1010 and PA1013 compared to PA721B-39 and PA824.

| Strain | OD$_{600}$ | Pantothenate g/L | HMBPA g/L |
|---|---|---|---|
| PA721B-39 | 18 | 4.0 | 0.22 |
| PA721B-39 | 16 | 4.1 | 0.25 |
| PA1013 #2 | 14 | 3.3 | 0.25 |
| PA1013 #4 | 14 | 4.2 | 0.28 |
| PA1013 #5 | 16 | 5.5 | 0.37 |
| PA1013 #8 | 13 | 3.6 | 0.24 |
| PA824 | 17 | 3.0 | 0.27 |
| PA824 | 16 | 3.1 | 0.29 |

Example V

Shake Flask and Fermentor Experiments with Strains with Increased Expression of serA and glyA Based on performance in test tubes, two strains with an amplifiable serA cassette and two strains with an amplifiable glyA cassette were selected, one each from two parents, PA824 and PA721B-39. The four strains were grown beside the parents in shake flasks (Table 8). In Soy flour MOPS Glucose (SMG) medium, all of the 4 strains produced more pantothenate than their parent strains. In Soy flour MOPS Maltose (SMM) medium one out of the four strains appeared superior to the parent strain.

The sera overexpressing strain and the glyA overexpressing strain from each parent were run simultaneously in 10-liter Chemap bench fermentors. The glyA overexpressing strain derived from PA824, PA1014-3, that had given the highest pantothenate titer in SMM, also performed the best in fermentors (Table 9). Strain PA1014-3 produced 71 g/l pantothenate in 36 hours in the culture supernatant and 86 g/l pantothenate in 48 hours in the culture supernatant compared to the parent PA824 which produced 41 g/l and 46 g/l pantothenate, respectively. The sera strain, PA1012-4, also produced significantly more pantothenate than the PA824 control in the culture supernatant, 52 g/l and 60 g/l at 36 and 48 hours, respectively. These results clearly demonstrate the effectiveness of increasing both glyA and sera.

The sera overexpressing and glyA overexpressing derivatives of PA721B-39 were clearly improved over their parent strain as well. Both produced about 80 g/l pantothenate (82 g/l and 79 g/l, respectively) in the culture supernatants in 48 hours. The effect of the increased PanB levels in the PA721B-39 derivatives versus the PA824 derivatives manifests itself in the reduction of HMBPA. PA721B-39 and its derivatives produce less HMBPA after 48 hours than PA824 or even PA668-24. Increasing GlyA also appears to lower the flow of carbon to HMBPA.

TABLE 8

Shake flask evaluation of pantothenate production strains overexpressing serA or glyA.

| Carbon source | Strain | Added cassette | HMBPA (g/l) | Pantothenate (g/l) |
|---|---|---|---|---|
| Glucose | PA824 | | 3.5 | 4.0 |
| | PA1012-4 | serA | 3.0 | 4.6 |
| | PA1014-3 | gly A | 2.5 | 4.7 |
| | PA721B-39 | | 0.9 | 5.0 |
| | PA1010-6 | serA | 1.9 | 9.6 |
| | PA1011-2 | gly A | 1.7 | 10.0 |
| Maltose | PA824 | | 1.2 | 10.4 |
| | PA1012-4 | serA | 0.8 | 9.8 |
| | PA1014-3 | gly A | 1.1 | 16.1 |
| | PA721B-39 | | 0.6 | 11.6 |
| | PA1010-6 | serA | 0.5 | 10.2 |
| | PA1011-2 | gly A | 0 | 10.3 |

All data are the average of duplicate shake flasks after 48 hours.
Conditions: 40 ml medium/200 ml baffled shake flask, 4X Bioshield covers, 300 rpm, 2.5% inoculum and 43° C.
Medium: 20 g/l Cargill 200/20 soy flour, 1 × PSTE, 8 g/l (NH4)2SO4 and 5 g/l glutamate.
Buffer: 0.1M phosphate pH 7.2 and 0.3M MOPS pH 7.2.
Carbon Source (Sterilized separately as 20 × stock): 60 g/l glucose or maltose w/10 mM Mg and 1.4 mM Ca.

TABLE 9

10 liter fermentor evaluations of pantothenate production strains overexpressing serA or glyA.

| run | Strain | Parent | Added cassette | HMBPA (g/l) 36 hrs | HMBPA (g/l) 48 hrs | Pantothenate (g/l) 36 hrs | Pantothenate (g/l) 48 hrs |
|---|---|---|---|---|---|---|---|
| P285 | PA824 | | | 18 | 25 | 41 | 46 |
| P284 | PA1012-4 | PA824 | serA | 20 | 21 | 52 | 60 |
| P286 | PA1014-3 | PA824 | glyA | 14 | 16 | 71 | 86 |
| P259 | PA721B-39 | | | 4 | 5 | 34 | 42 |
| P287 | PA1010-6 | PA721B-39 | serA | 4 | 5 | 65 | 82 |
| P289 | PA1011-2 | PA721B-39 | glyA | 2 | 3 | 56 | 79 |
| P275 | PA668-24 | PA824 | | 3 | 9 | 55 | 72 |

The medium used is PFM-222. It is the same as medium PFM-155 described in U.S. Ser. No. 60/262,995 (filed Jan. 19, 2001) except for the following changes: (1) In the Batch Material: There is no Amberex 1003. Cargill 200/20 (soy flour) 40 g/L has been changed to Cargill 20–80 (soy grits) 50 g/L, MgSO$_4$.7H$_2$O is replaced with MgCl$_2$.7H$_2$0, 1 g/L, and SM-1000X is replaced with PSTE-1000X (PSTE-1000X = MnCl$_2$.4H$_2$O, 2.0 g/L; ZnSO$_4$.7H$_2$O, 1.5 g/L; CoCl$_2$.6H$_2$O, 2.0 g/L; CuSO$_4$.5H$_2$O, 0.25 g/L; Na$_2$MoO$_4$.2H$_2$O, 0.75 g/L). In the Feed Material: SM-1000X is replaced with PSTE-1000X Increasing pantothenate production can also be achieved by combining overexpression of serA and glyA in a single stain, and/or by introducing a mutation that leads to feedback resistant serA or glyA, or both.

Example VI

Increasing the Expression of the GlyA Gene by Mutating the Purr Gene

As described in Examples III and V, expression of the glyA gene can be increased by adding one or more copies of a cassette in which the glyA gene is driven by a strong, constitutive promoter. An alternative method to increase glyA expression is to alter its regulation. Literature describing a glyA::lacZ fusion suggests that the glyA promoter is of moderate strength under normal conditions (about 400 Miller Units), but that this promoter is capable of being induced to relatively high levels (1,800 Miller units) if its negative regulator, the purR gene, is deleted (Saxild et al. (2001) *J. Bacteriol.* 183:6175-6183). Therefore, experiments were preformed to determine if glyA expression, and consequently pantothenate production, could be increased by deleting purR from a pantothenate production strain.

Figure 8:
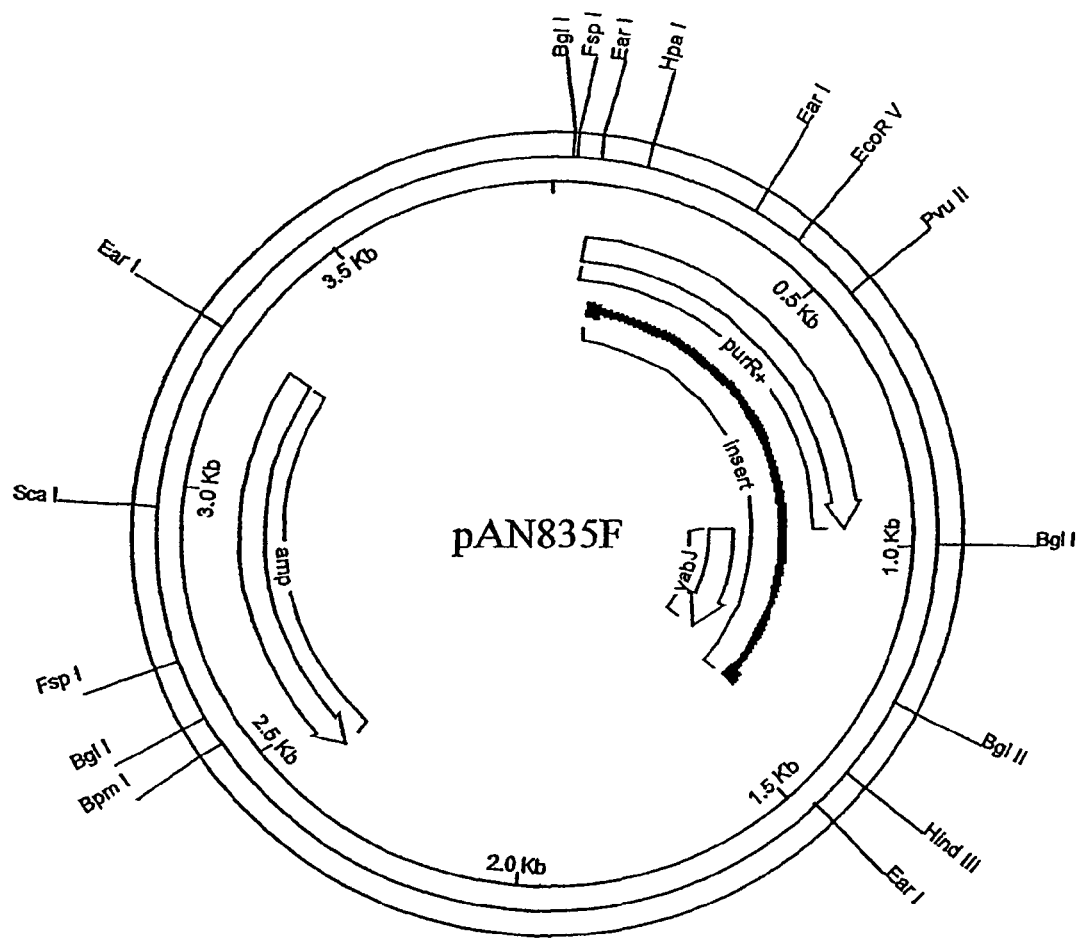
FIG. 8 is a schematic representation of the structure of pAN835F, a clone of the *B. subtilis* purR gene.
Figure 9:
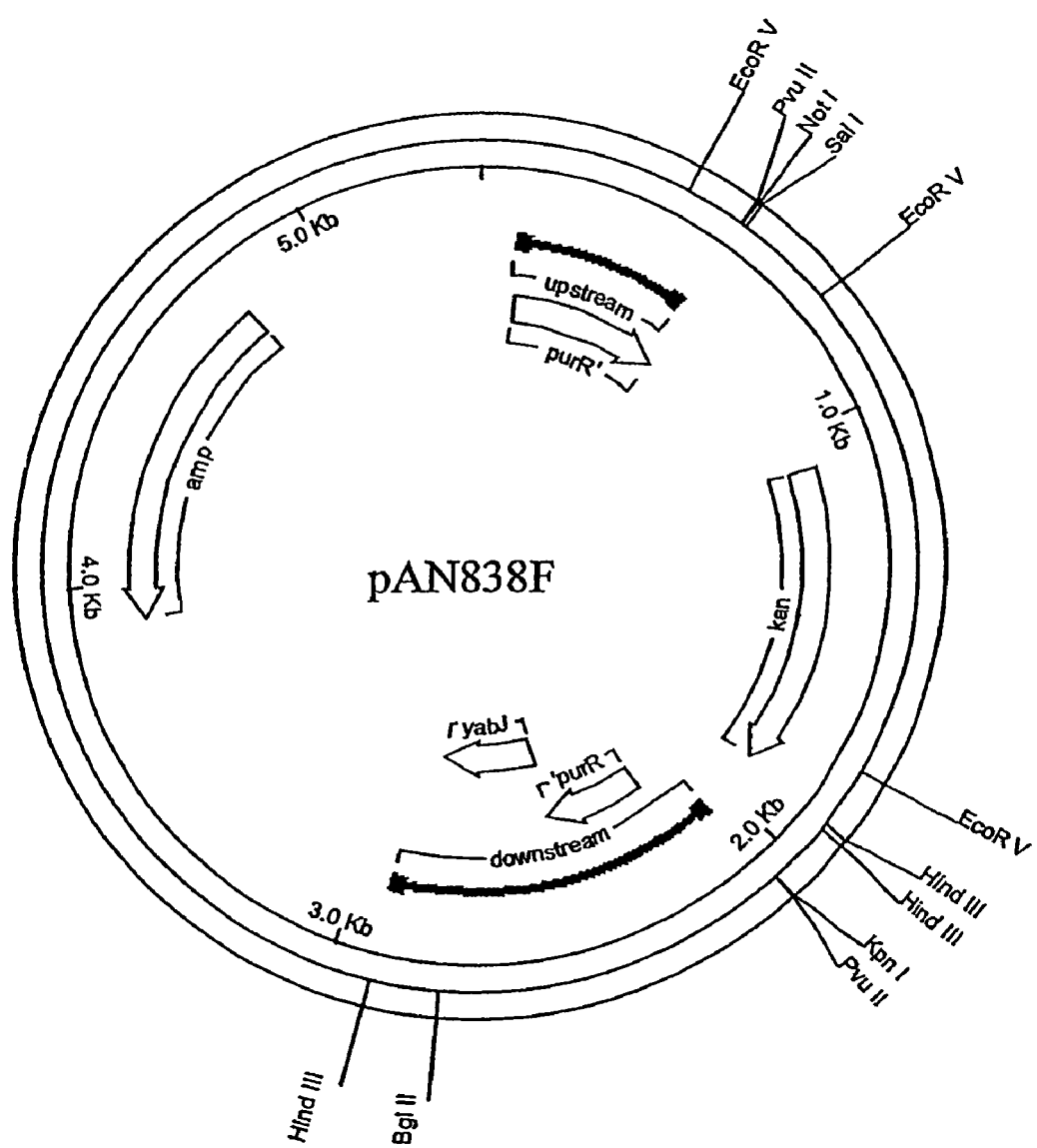
FIG. 9 is a schematic representation of the structure of pAN838F, a plasmid designed to install a disruption of the *B. subtilis* purR gene.

The *B. subtilis* purR gene was amplified from PY79 chromosomal DNA by PCR, and the resulting fragment was cloned into PvuII cleaved pGEM-5-Zf(+) vector DNA to give plasmid pAN835F (SEQ ID NO:26, FIG. 8). This step eliminated the PvuII sites at both ends of the insert, leaving a unique PvuII site in the middle of the purR open reading frame. Next, a blunt PCR DNA fragment containing the Gram positive kanamycin resistance gene from pAN363F (SEQ ID NO:27) was ligated into this unique PvuII site of pAN835F to give pAN838F (SEQ ID NO:28, FIG. 9).

pAN838F was then transformed into PY79, PA668-24, and PA824, selecting for kanamycin resistance at 10 mg/l to give new sets of strains named PA1059, PA1060, and PA1061, respectively. It was shown by PCR that all new isolates contained the disrupted purR::kan allele that was expected from a double crossover event. Several isolates of PA1060 and PA1061 were tested for pantothenate production in test tube cultures grown in SVY glucose plus β-alanine (Table 10). The best isolates derived from PA668-24, PA1060-2 and PA1060-4, gave an improvement from 3.0 g/l pantothenate to 5.3 to 5.1 g/l, respectively, which is an increase of 75%. Likewise, the best isolates derived from PA824, PA1061-1 and PA1061-2 gave an increase from about 3.1 g/l to 5.4 g/l, also a 75% gain. These results suggest that the glyA gene is substantially induced in these new strains by disruption of the purR gene. Alternatively, the improvements in pantothenate production in PA1060 and PA1061 may be due to more complex pleiotropic effects. In either case, deregulation of the purR regulon has a positive effect on pantothenate production.

In other embodiments, the purR disruption can be installed in other pantothenate production strains, for example those that have an integrated $P_{26}$serA allele or more than one copy of the $P_{26}$panBCD operon. The purR gene can also be used as a site for addition of desired expression cassettes, such as P26panB. One can also use resistance to the guanine analogs, such as 8-azaguanine, as a selection for a purR mutation.

TABLE 10

Production of pantothenate and fantothenate by derivatives of PA824 and PA668-24 containing disrupted purR, in test tube cultures grown in SVY glucose plus 5 g/l β-alanine.

Figure 10:
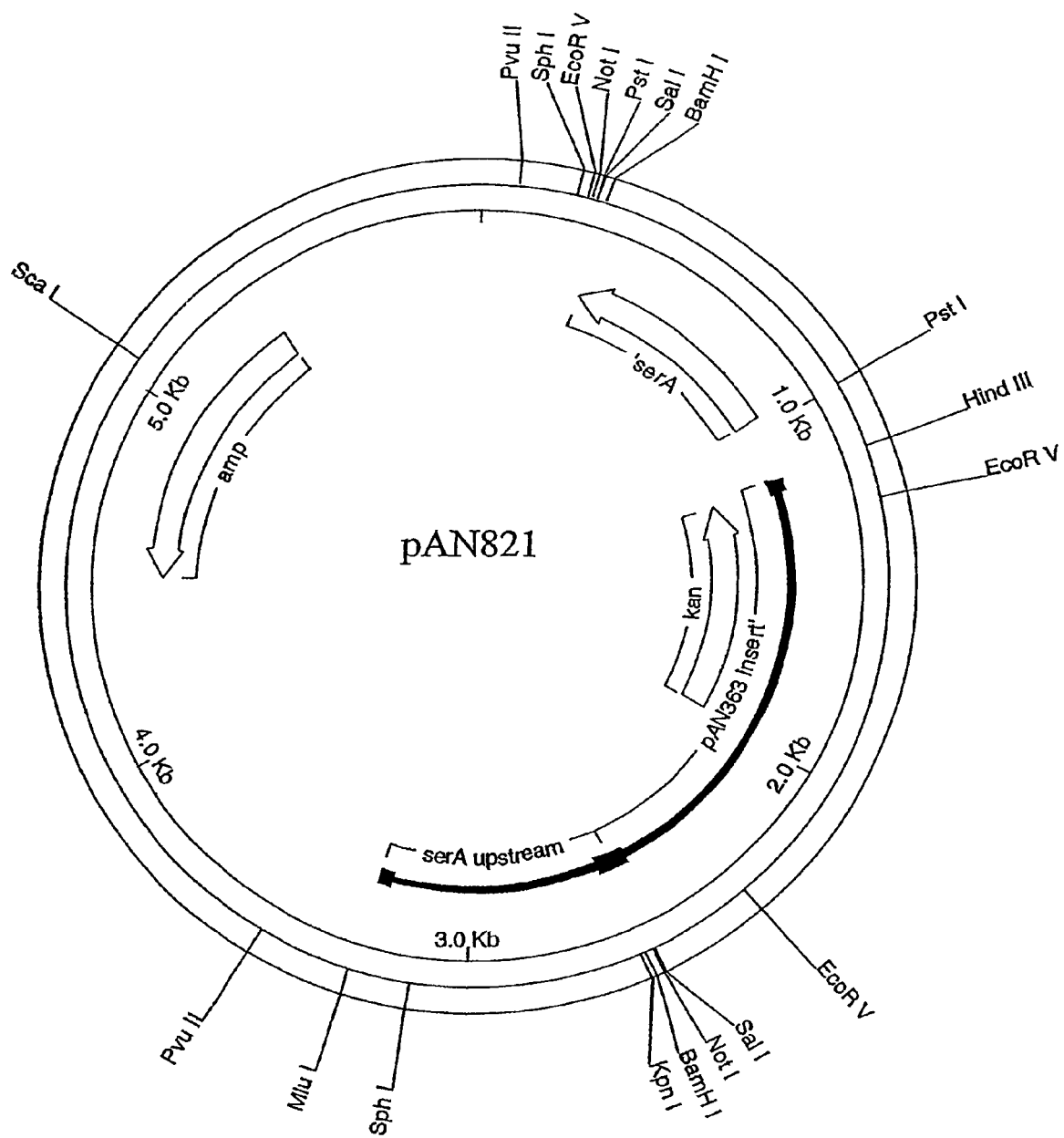
FIG. 10 is a schematic representation of the structure of pAN821, a plasmid designed to delete a portion of the serA gene, selecting for kanamycin resistance.

| Strain | inoculum* | parent | new feature | $OD_{600}$ | [fan] g/l | [pan] g/l |
|---|---|---|---|---|---|---|
| PA668-24 | cam 5, tet 7.5 | PA824 | — | 9 | b.d. | 3.0 |
| " | cam 5, tet 7.5 | " | — | 12 | b.d. | 3.0 |
| PA1060-1 | cam 5, tet 7.5 | PA668-24 | purR::kan | 14 | 0.14 | 4.5 |
| PA1060-2 | cam 5, tet 7.5 | " | " | 12 | b.d. | 5.3 |
| PA1060-3 | cam 5, tet 7.5 | " | " | 12 | b.d. | 4.5 |
| PA1060-4 | cam 5, tet 7.5 | " | " | 16 | 0.11 | 5.1 |
| PA824 | tet 30 | PA377 | — | 9 | 0.25 | 3.2 |
| " | " | " | — | 11 | 0.22 | 3.0 |
| PA1061-1 | tet 15 | PA824 | purR::kan | 13 | 0.45 | 5.4 |
| PA1061-3 | " | " | " | 14 | 0.39 | 5.4 |
| PA1061-4 | " | " | " | 11 | 0.40 | 4.7 | b.d. = below detection
*concentration of antibiotics in the petri plate from which the inoculum colony was taken Example VII Overexpression of the serA Gene from a Non-Amplifiable Cassette This Example describes another method to increase serine production, in which a two step procedure deposits a strong, constitutive promoter ($P_{26}$) in front of the chromosomal serA gene. Two plasmids were constructed, each containing about 700 base pairs of DNA sequence from the region immediately upstream of the native sera gene. The first plasmid, pAN821, also contains the 3' half of the sera coding region, and in between the two aforementioned sequences, a kanamycin resistance gene (SEQ ID NO:30, FIG. 10). When transformed into B. subtilis, selecting for kanamycin resistance, pAN821 will give a disruption of the sera gene, leading to serine auxotrophy. This creates a genetic sequence termed the ΔserA::kan allele.

Figure 11:
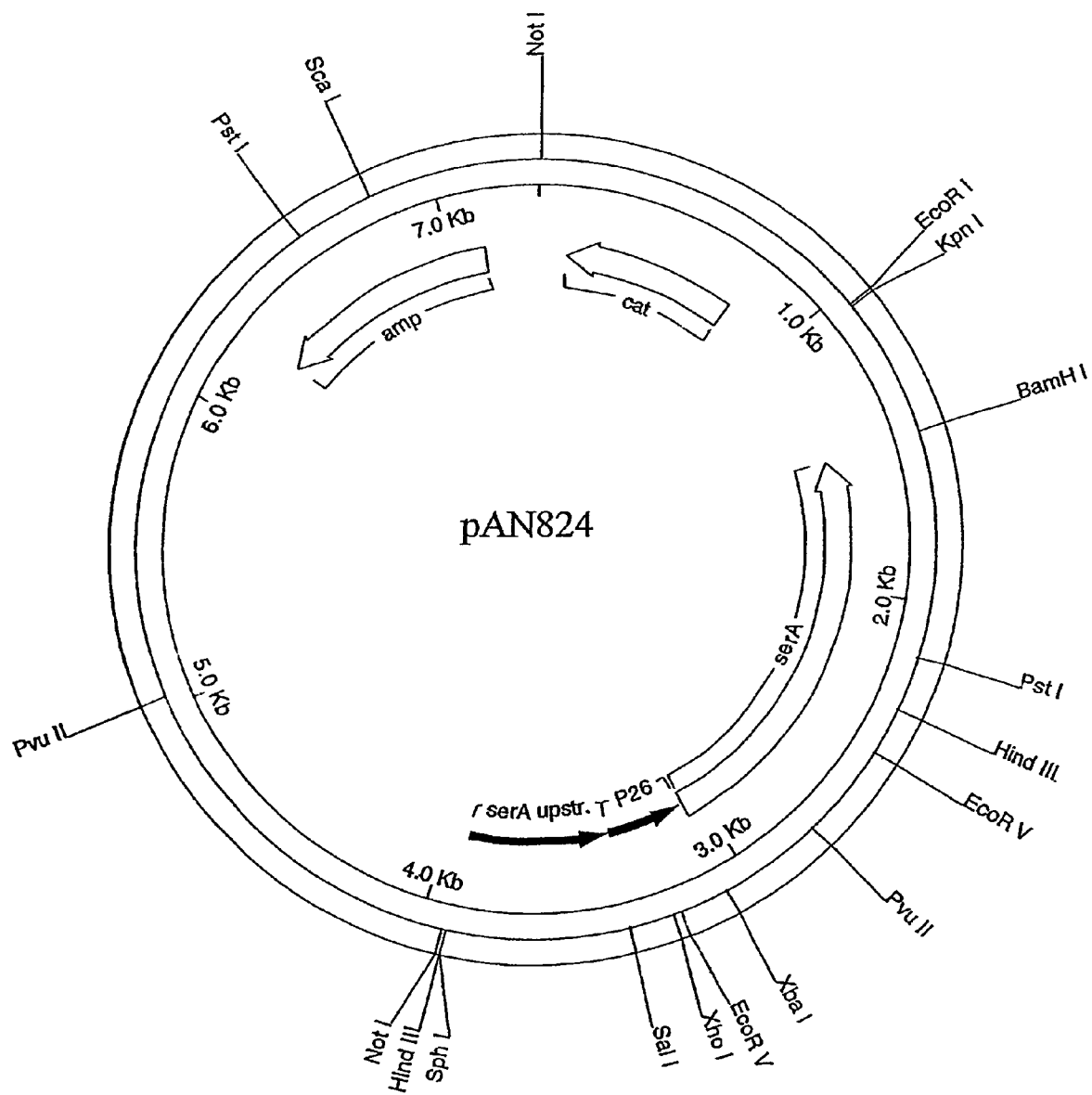
FIG. 11 is a schematic representation of the structure of pAN824, a plasmid designed to integrate a non-amplifiable $P_{26}$serA cassette at the sera locus, selecting for Ser⁺.
Figure 12:
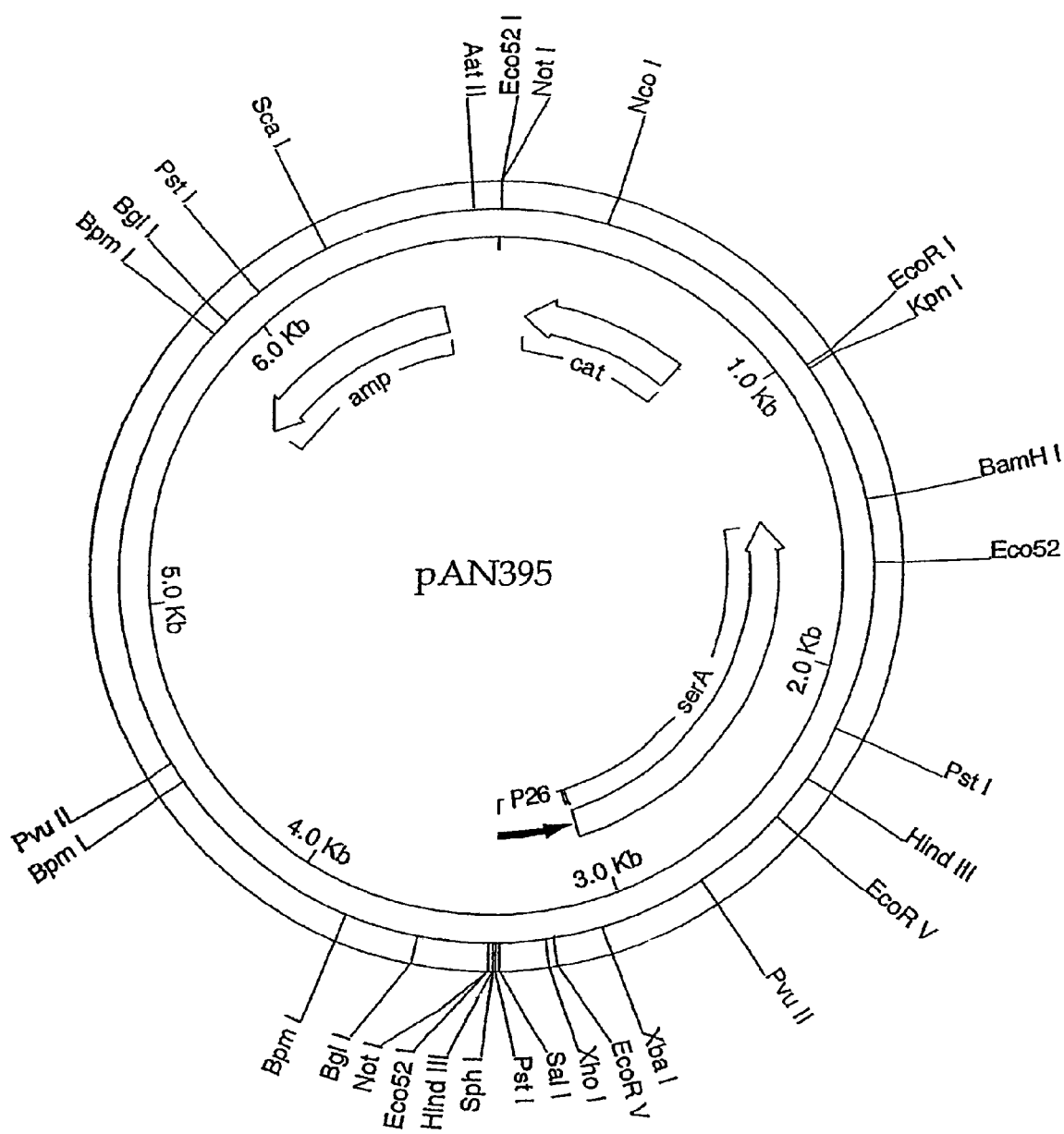
FIG. 12 is a schematic representation of the structure of pAN395, a medium copy plasmid designed to integrate and amplify a P26 serA expression cassette at the serA locus.

The second plasmid, designed to introduce the $P_{26}$ sera structure, was constructed by inserting the serA upstream sequence at the 5' end of the $P_{26}$ promoter in pAN395. The resulting plasmid, pAN824, is shown in FIG. 11 (SEQ ID NO:31). The plasmid pAN395 is similar to pAN393 described in Example IV. The open reading frame of the sera gene was synthesized by PCR using B. subtilis PY79 DNA as the template. The upstream primer contains an XbaI site and a moderately strong synthetic ribosome binding site, RBS2. The downstream primer contains a BamHI site. This serA open reading frame was used to replace the panBCD genes in the medium copy plasmid, pAN006, to give pAN395 (SEQ ID NO:29, FIG. 12). This plasmid contains the sera gene expressed from the $P_{26}$ promoter and the RBS2 ribosome binding site.

The ΔserA::kan allele from pAN821 was introduced into strain PA824 to give PA1026. As expected, PA1026 did not grow on minimal medium. In the second step, the $P_{26}$ serA cassette from plasmid pAN824 was introduced into PA1026, selecting for serine prototrophy, to give strain PA1028. Several PA1028 isolates were confirmed to have the expected chromosomal structure ($P_{26}$ serA) by diagnostic PCR. These isolates were then tested for pantothenate production in test tube cultures grown for 48 hours in SVY plus 5 g/l β-alanine (Table 11). The PA1028 isolates (derived from PA824) gave increases from 10% to 25% in pantothenate production. As shown in Table 12, in shake flask experiments, PA824 produced about 7 g/l pantothenate, whereas: PA 1028 produced 11 g/l.

Example VIII

Construction of Pantothenate Producing Strains that Contain Both an Integrated Non-Amplifiable $P_{26}$ serA Cassette and an Amplifiable $P_{26}$glyA Cassette Since a non-amplifiable $P_{26}$ serA cassette integrated at serA led to higher pantothenate synthesis (see, e.g., Table 12), and since a chloramphenicol amplifiable $P_{26}$ glyA cassette at glyA led to much higher pantothenate synthesis (see, e.g., PA1014-3, Table 8), it was, proposed that a combination of the two might be synergistic. Strain PA1028-4, which is the derivative of PA824 that contains the non-amplifiable $P_{26}$ serA cassette integrated at serA, was transformed to chloramphenicol resistance at 5 mg/l using chromosomal DNA from PA1014-3, to give a set of strains named PA1038, which now contain the chloramphenicol amplifiable $P_{26}$glyA cassette.

PA1038 isolates were tested for pantothenate production using standard test tube cultures grown in SVY plus β-alanine (Table 13). As expected, PA1038 showed a dramatic increase in pantothenate production from about 4.2 g/l by PA824 to 6.6 to 7.5 g/l by the PA1038 set. Isolates PA1038-3 and PA1038-12 were further tested in shake flasks as shown in Table 12. Both produced an average of 13.6 g/l pantothenate, as compared to the 7.4 g/l pantothenate produced by PA824.

TABLE 11

Production of pantothenate and fantothenate by derivatives of PA824 that contain a single copy of $P_{26}$ serA at the serA locus, in 48 hour test tube cultures grown in SVY plus 5 g/l β-alanine.

| Strain | parent | $OD_{600}$ | [fan] g/l | [pan] g/l |
|---|---|---|---|---|
| PA824 | | 17 | 0.44 | 4.0 |
| PA824 | | 15 | 0.45 | 4.0 |
| PA1028-1 | PA824 | 13 | 0.46 | 4.4 |
| PA1028-2 | " | 18 | 0.49 | 4.9 |
| PA1O28-3 | " | 15 | 0.44 | 4.4 |
| PA1028-4 | " | 13 | 0.43 | 4.5 |
| PA1028-5 | " | 14 | 0.45 | 4.4 |
| PA1028-6 | " | 11 | 0.43 | 4.8 |
| PA1028-8 | " | 15 | 0.51 | 5.0 | b.d. = below detection

TABLE 12

Shake flask evaluation of pantothenate production strains overexpressing serA and/or glyA.

| Strain | Parent | glyA cassette | serA cassette | Fantothenate (g/l) | Pantothenate (g/l) |
|---|---|---|---|---|---|
| PA824 | | | | 0.6 | 7.4 |
| PA1014-3 | PA824 | N × $P_{26}$glyA | | 0.7 | 12.0 |
| PA1028-4 | PA824 | | $P_{26}$serA @ serA | 0.8 | 11.1 |
| PA1038-3 | PA1028-4 | N × $P_{26}$glyA | $P_{26}$serA @ serA | 0.5 | 13.6 |
| PA1038-12 | PA1028-4 | N × $P_{26}$glyA | $P_{26}$serA @ serA | 0.6 | 13.6 |

All data are the average of duplicate shake flasks after 48 hours.
Conditions: 40 ml medium / 200 ml baffled shake flask, 4 × Bioshield covers, 300 rpm, 2.5% inoculum and 43° C.
Inoculum: SVY base w/maltose 24 hours at 43° C.
Medium: 20 g/l Cargill 200/20 soy flour, 8 g/l $(NH_4)_2SO_4$, 5g/l glutamate and 1 × PSTE.
Buffer: 0.1 M phosphate pH 7.2 and 0.3 M MOPS pH 7.2.
Carbon Source (Sterilized separately as 20 × stock): 30 g/l maltose, 5 mM $MgCl_2$ and 0.7 mM $CaCl_2$.

TABLE 13

Pantothenate production by PA1038, a derivative of PA824 that contains a non-amplifiable $P_{26}$ serA cassette at serA and an amplifiabie $P_{26}$ glyA cassette at glyA.

| Strain | Inoculum Medium | $OD_{600}$ | [Fan] g/L | [Pan] g/L |
|---|---|---|---|---|
| PA824 | tet 15 | 16 | 0.56 | 4.4 |
| PA824 | " | 14 | 0.59 | 4.3 |
| PA824 | tet 30 | 12 | 0.57 | 4.3 |
| PA824 | " | 14 | 0.58 | 4.2 |
| PA1038-3 | cam 5, tet 15 | 16 | 0.47 | 7.2 |
| PA1038-4 | " | 14 | 0.49 | 7.0 |
| PA1038-5 | " | 15 | 0.52 | 7.0 |
| PA1038-6 | " | 15 | 0.51 | 7.2 |
| PA1038-9 | " | 14 | 0.56 | 7.2 |
| PA1038-11 | " | 13 | 0.49 | 6.6 |
| PA1038-12 | " | 16 | 0.58 | 7.5 |

Test tube cultures were grown with SVY glucose plus 5 g/l β-alanine at 43° C. for 48 hours.

Example IX

Increasing the Production of MTF by Altering the Glycine Cleavage Pathway

As demonstrated with the above examples, increasing MTF production in bacteria increases the production of pantothenate in stains that have been engineered to produce more pantothenate by manipulation of the panBCD and/or panE genes. It has been demonstrated that pantothenate production can be increased by increasing the expression of the glyA or the serA gene. Stronger promoters or ribosome binding sites can be used to increase glyA or sera expression as demonstrated in Examples III through V and VII through VIII. Alternatively, the expression of the glyA gene can be deregulated in *Bacillus* by disrupting the purR repressor gene as illustrated in Example VI.

Another method to increase MTF production is to enhance the expression of enzymes of the glycine cleavage pathway. For example, enzymes encoded by the gcvT, gcvPA, gcvPB, gcvH, and pdhD genes catalyze the breakdown of glycine to MTF, $CO_2$, and $NH_3$. A strong, constitutive promoter, such as the SP01 phage $P_{26}$ promoter described previously, can be cloned in front of the gcvT-gcvPA-gcvPB operon or in front of the gcvH or pdhD gene to enhance their expression. In addition to the above mentioned approaches, additional glycine, which is inexpensive, can be added to the medium to further enhance MTF production by any strain engineered as described herein.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A process for the enhanced production of pantothenate, comprising culturing a recombinant microorganism selected from the group consisting of *Bacillus, Corynebacterium, Lactobacillus, Streptomyces, Salmonella, Escherichia, Klebsiella, Serratia, Proteus,* and *Saccharomyces* having
   (i) a deregulated pantothenate biosynthetic pathway, and
   (ii) a deregulated methylenetetrahydrofolate (MTF) biosynthetic pathway, under conditions such that pantothenate production is enhanced as compared to a wild-type microorganism, wherein the deregulated pantothenate biosynthetic pathway is achieved by overexpressing at least one gene selected from the group consisting of panB, panC, panD, and panE1, and wherein the deregulated MTF biosynthetic pathway is achieved by overexpressing at least one gene selected from the group consisting of gcv, serA, serC, serB, glyA, sul, fol, mtrA, pab, panB and purR derived from a microorganism of the genus *Bacillus, Corynebacterium, Lactobacillus, Lactococci,* or *Streptomyces*.

2. The process of claim 1, wherein said microorganism has at least two pantothenate biosynthetic enzymes deregulated.

3. The process of claim 1, wherein said microorganism has at least three pantothenate biosynthetic enzymes deregulated.

4. The process of claim 1, wherein said microorganism has at least four pantothenate biosynthetic enzymes deregulated.

5. The process of claim 4, wherein said microorganism has a deregulated ketopantoate hydroxymethyltransferase, a deregualted ketopantoate reductase, a deregulated pantothenate synthetase and a deregulated aspartate-α-decarboxylase.

6. The process of claim 1, wherein said microorganism further has a deregulated isoleucine-valine (ilv) biosynthetic pathway.

7. The process of claim 6, wherein said microorganism has at least two isoleucine-valine (ilv) biosynthetic enzymes deregulated.

8. The process of claim 6, wherein said microorganism has at least three isoleucine-valine (ilv) biosynthetic enzymes deregulated.

9. The process of claim 8, wherein said microorganism has a deregulated acetohydroxyacid acid synthetase, a deregulated acetohydroxyacid isomeroreductase, and a deregulated dihydroxyacid dehydratase.

10. The process of claim 1, wherein the microorganism has at least one MTF biosynthetic enzyme deregulated.

11. The process of claim 10, wherein the microorganism has a deregulated glyA gene.

12. The process of claim 10, wherein the microorganism has a deregulated serA gene.

13. The process of claim 10, wherein the microorganism has a deregulated glyA gene and a deregulated serA gene.

14. The process of claim 11 or 13, wherein the microorganism has a mutated, deleted or disrupted purR gene.

15. The process of claim 1, wherein said microorganism is cultured under conditions of excess serine.

16. The process of claim 1, wherein the microorganism is a Gram positive microorganism.

17. The process of claim 1, wherein the microorganism belongs to the genus *Bacillus*.

18. The process of claim 1, wherein the microorganism is *Bacillus subtilis*.

19. The process of claim 1, wherein the microorganism overexpresses relative to a wild-type cell at least one methylenetetrahydrofolate (MTF) biosynthetic enzyme encoded by glyA, serA, serC, serB, gcvT, gcvPA, gcvPB, or gcvH.

20. The process of claim 14, wherein the microorganism overexpresses the glyA gene as a result of a mutation in the purR repressor gene.

21. The process of claim 14, wherein the microorganism further has a deregulated methylenetetrahydrofolate (MTF) biosynthetic enzyme encoded by glyA, serA, serC, serB, gcvT, gcvPA, gcvPB, or gcvH.

22. The process of claim 14, wherein the microorganism further has a deregulated pantothenate biosynthetic pathway.

23. The process of claim 22, wherein said microorganism has at least two pantothenate biosynthetic enzymes deregulated.

24. The process of claim 22, wherein said microorganism has at least three pantothenate biosynthetic enzymes deregulated.

25. The process of claim 22, wherein said microorganism has at least four pantothenate biosynthetic enzymes deregulated.

26. The process of claim 25, wherein said microorganism has a deregulated ketopantoate hydroxymethyltransferase, a deregualted ketopantoate reductase, a deregulated pantothenate synthetase and a deregulated aspartate-α-decarboxylase.

27. The process of claim 14, wherein said microorganism further has a deregulated isoleucine-valine (ilv) biosynthetic pathway.

28. The process of claim 27, wherein said microorganism has at least two isoleucine-valine (ilv) biosynthetic enzymes deregulated.

29. The process of claim 27, wherein said microorganism has at least three isoleucine-valine (ilv) biosynthetic enzymes deregulated.

30. The process of claim 29, wherein said microorganism has a deregulated acetohydroxyacid acid synthetase, a deregulated acetohydroxyacid isomeroreductase, and a deregulated dihydroxyacid dehydratase.

31. The process of claim 14, wherein said microorganism is cultured under conditions of excess serine.

32. The process of claim 14, wherein the microorganism is a Gram positive microorganism.

33. The process of claim 14, wherein the microorganism belongs to the genus *Bacillus*.

34. The process of claim 14, wherein the microorganism is *Bacillus subtilis*.

* * * * *